United States Patent [19]

Aristoff

[11] Patent Number: 4,588,823
[45] Date of Patent: May 13, 1986

[54] 9-SUBSTITUTED CARBACYCLIN ANALOGS

[75] Inventor: Paul A. Aristoff, Portage, Mich.

[73] Assignee: The Upjohn Company, Kalamazoo, Mich.

[21] Appl. No.: 655,403

[22] Filed: Sep. 27, 1984

Related U.S. Application Data

[62] Division of Ser. No. 349,145, Feb. 16, 1982, Pat. No. 4,487,961.

[51] Int. Cl.[4] .......................................... C07C 177/00
[52] U.S. Cl. .................................. 549/422; 549/79;
549/501; 556/441; 260/404; 260/404.5;
260/408; 260/410; 260/410.5; 260/410.9 R;
260/413; 560/12; 560/39; 560/45; 560/56;
560/119; 562/455; 562/466; 562/427; 562/444;
562/501; 564/152; 564/158; 564/159; 564/172;
564/91; 564/97; 564/188; 564/96; 564/98;
564/428; 564/454; 568/819; 564/455; 564/466;
564/87; 564/501; 568/374; 564/88; 568/633;
568/734; 564/89; 558/426; 564/427; 558/432
[58] Field of Search ............... 560/119, 12, 39, 45,
560/56; 562/427, 444, 455, 460, 501; 568/374,
819, 633, 734; 260/404, 404.5, 408, 410, 410.9
R, 413, 464, 465 D, 465 F; 564/152, 158, 159,
172, 188, 88, 89, 91, 96, 97, 98, 99, 427, 428,
454, 455, 466, 501; 556/441; 549/79, 422, 501

[56] References Cited

U.S. PATENT DOCUMENTS

| 4,180,657 | 12/1979 | Sih ........................... 542/426 |
| 4,192,891 | 3/1980 | Haslanger ........................ 424/305 |
| 4,225,508 | 9/1980 | Sih ........................... 260/346.22 |
| 4,238,414 | 12/1980 | Morton, Jr. ......................... 564/453 |
| 4,306,075 | 12/1981 | Aristoff ............................. 560/56 |
| 4,306,076 | 12/1981 | Nelson .............................. 560/56 |

FOREIGN PATENT DOCUMENTS

| 2900352 | 7/1979 | Fed. Rep. of Germany . |
| 4024865 | 2/1979 | Japan . |
| 4063059 | 5/1979 | Japan . |
| 4063060 | 5/1979 | Japan . |
| 2012265 | 7/1979 | United Kingdom . |
| 2013661 | 8/1979 | United Kingdom . |
| 2017699 | 10/1979 | United Kingdom . |

OTHER PUBLICATIONS

Aristoff, P. A., J. Org. Chem. 46 (No. 9), 1981, pp. 1954–1957, "Practical Synthesis of 6a-Carbaprostaglandin I₂.
Barco, A., et al., J. Org. Chem. 45 (No. 23), 1980, pp. 4776–4778, "A New, Elegant Route to a Key Intermediate for the Synthesis of 9(O)-Methanoprostacyclin".
Hayashi, M., et al., Chem. Lett. 1979, pp. 1437–1440, "A Synthesis of 9(O)-Methanoprostacyclin".
Kojima, K., et al., Tetrahedron Lett. 39, 1978, pp. 3743–3746, "Total Synthesis of 9(O)-Methanoprostacyclin and its Isomers".
Morton, D. R., Jr., et al., Org. Chem. 44 (No. 16), 1979, pp. 2880–2887, "Total Synthesis of 6a-Carbaprostaglandin I₂ and Related Isomers".
Nicolaou, K. C., et al., J.C.S. Chem. Comm., 1978, pp. 1067–1068, "Total Synthesis of Carboprostacyclin, a Stable and Biologically Active Analogue of Prostacyclin (PGI₂)".
Shibasaki, M., et al., Chem. Lett. 1979, pp. 1299–1300, "A Stereo and Regiospecific Route to the Synthetic Intermediate for the Synthesis of 9(O)-Methanoprostacyclin".
Skuballa, W., et al., Angew. Chem. 93 (No. 12), 1981, pp. 1080–1081, "Ein neuer Weg zu 6a-Carbacyclinen—Synthese eines stabilen, biologisch potenten Prostacyclin-Analogons".
Shibasaki, M. et al., Tetrahedron Lett. 5, 1979, pp. 433–436, "New Synthetic Routes to 9(O)-Methanoprostacyclin, A Highly Stable and Biologically Potent Analog of Prostacyclin".
Sugie, A., et al., Tetrahedron Lett. 28, 1979, pp. 2607–2610, "Stereocontrolled Approaches to 9(O)-Methanoprostacyclin".
Yamazaki, M., et al., Chem. Lett. 1981, pp. 1245–1248, "1,2-Carbonyl Transposition of cis-Bicyclo[3.3.0]octan-2-one to its 3-one Skeleton: Application to Syntheses of dl-Hirsutic Acid and dl-9-(O)-Methanoprostacyclin".

Primary Examiner—Robert Gerstl
Attorney, Agent, or Firm—L. Ruth Hattan

[57] ABSTRACT

Novel compounds of the following general formula:

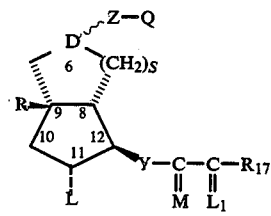

3 Claims, No Drawings

9-SUBSTITUTED CARBACYCLIN ANALOGS

This is a division of U.S. application Ser. No. 349,145, filed Feb. 16, 1982, now U.S. Pat. No. 4,487,961.

BACKGROUND OF THE INVENTION

The present invention relates to novel compounds which are 9-substituted carbacyclin analogs, to processes for the preparation of said carbacyclin analogs and the use of said analogs as pharmacological agents or as intermediates for the preparation of compounds useful as pharmacological agents. This invention also relates to chemical intermediates for preparing the novel 9-substituted carbacyclin compounds described and claimed herein.

Prostacyclin is an endogeneously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "PGI$_2$". Carbacyclin, 6a-carba-PGI$_2$, exhibits the structure and carbon atom numbering indicated in formula II when the C-5,6 positions are unsaturated. Likewise, for convenience, carbacyclin is referred to simply as "CBA$_2$".

A stable partially saturated derivative of PGI$_2$ is PGI$_1$ or 5,6-dihydro-PGI$_2$ when the C-5,6 positions are saturated, depicted with carbon atom numbering in formula I when the C-5,6 positions are saturated. The corresponding 5,6-dihydro-CBA$_2$ is CBA$_1$, depicted in formula II when the C-5,6 positions are saturated.

As is apparent from inspection of formulas I and II, prostacyclin and carbacyclin may be trivially named as derivatives of PGF-type compounds, e.g., PGF$_{2\alpha}$ of formula III. Accordingly, prostacyclin is trivially named 9-deoxy-6,9$\alpha$-epoxy-(5Z)-5,6-didehydro-PGF$_1$ and carbacyclin is named 9-deoxy-6,9$\alpha$-methano-(5Z)-5,6-didehydro-PGF$_1$. For description of prostacyclin and its structural identification, see Johnson, et al, Prostaglandins 12:915 (1976).

In naming the novel compounds of the present invention in general the art-recognized system of nomenclature described by N. A. Nelson, J. Med. Chem. 17:911 (1974) for prostaglandins is followed. As a matter of convenience, however, the novel carbacyclin derivatives herein are named as 6a-carba-prostaglandin I$_2$ compounds, or as CBA$_1$ or CBA$_2$ derivatives.

In the formulas herein, broken line attachments to a ring indicate substituents in the "alpha" ($\alpha$) configuration, i.e., below the plane of said ring. Heavy solid line attachments to a ring indicate substituents in the "beta" ($\beta$) configuration, i.e., above the plane of said ring. The use of wavy lines ($\sim$) herein will represent attachment of substituents in the alpha or beta configuration or attached in a mixture of alpha and beta configurations. Alternatively wavy lines will represent either an E or Z geometric isomeric configuration or the mixture thereof. Also, solid and dotted lines used together, as for example, in formulas I and II at C-5,6 positions indicates the presence of either a double bond or alternatively a single bond.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel carbacyclin analogs herein. Molecules of carbacyclin have several centers of asymmetry and therefore can exist in optically inactive form or in either of two enantiomeric (optically active) forms, i.e., the dextrorotatory and laveorotatory forms. The racemic form of carbacyclin contains equal numbers of both enantiomeric molecules. For convenience, reference to carbacyclin or CBA$_2$ or CBA$_1$ will refer to the optically active form thereof.

A formula as drawn herein which depicts a prostacyclin-type product or an intermediate useful in the preparation thereof, represents that particular stereoisomer of the prostacyclin-type product which is of the same relative sterochemical configuration as prostacyclin obtained from mammalian tissues or the particular stereoisomer of the intermediate which is useful in preparing the above stereoisomer of the prostacyclin type product. As drawn, formula I corresponds to that of PGI$_2$ endogenously produced in the mammalian species. In particular, refer to the stereochemical configuration at C-8 ($\alpha$), C-9 ($\alpha$), C-11 ($\alpha$) and C-12 ($\beta$) of endogenously produced prostacyclin. The mirror image of the above formula for prostacyclin represents the other enantiomer.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia Nos. 63,059 and 63,060, also abstracted respectively as Derwent Farmdoc CPI Numbers 48154B/26 and 48155B/26. See also British published specifications Nos. 2,012,265 and German Offenlungsschrift No. 2,900,352, abstracted as Derwent Farmdoc CPI Number 54825B/30. See also British pulished applications 2,017,699 and 2,013,661 and U.S. Pat. No. 4,238,414. The synthesis of carbacyclin and related compounds is also reported in the chemical literature, as follows: Morton, D. R., et al, J. Org. Chem., 44:2880 (1979); Shibasaki, M., et al, Tetrahedron Lett., 433–436 (1979); Kojima, K., et al, Tetrahedron Lett., 3743–3746 (1978); Nicolaou, K. C., et al, J. Chem. Soc., Chemical Communications, 1067–1068 (1978); Sugie, A., et al, Tetrahedron Lett., 2607–2610 (1979); Shibasaki, M., Chem. Lett., 1299–1300 (1979), and Hayashi, M., Chem. Lett., 1437–40 (1979); Aristoff, P. A., J. Org. Chem. 46, 1954–1957(1981); Yamazaki, M., et al, Chem. Lett., 1245-1248(1981); and Barco, A., et al, J. Org. Chem. 45, 4776-4778 (1980); and Skuballa, W., et al, Angew. Chem., 93, 1080-1081 (1981). 7-Oxo and 7-hydroxy-CBA$_2$ compounds are apparently disclosed in U.S. Pat. No. 4,192,891. 19-Hydroxy-CBA$_2$ compounds are disclosed in U.S. Ser. No. 054,811, filed July 5, 1979. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai No. 77/24,865, published Feb. 24, 1979. Related 9$\beta$-substituted compounds are disclosed in U.S. Pat. Nos. 4,306,075 and 4,306,076.

SUMMARY OF THE INVENTION

The present invention consists of compounds of formula IV wherein R is —CN; —CH$_2$X wherein X is chloro or bromo; —CH=CH$_2$; —CHO; —CH$_2$OH; —C≡CH; —C≡C—CF$_3$; —C≡C—C$_n$H$_{2n}$CH$_3$ wherein n is zero, one, 2 or 3; cis-CH=CHC$_n$H$_{2n}$CH$_3$ or trans —CH=CHC$_n$H$_{2n}$CH$_3$ wherein n is zero, one, 2 or 3; —CH=C(X')$_2$ wherein X' is fluoro, chloro, or bromo; cis-CH=CHX' or trans-CH=CHX' wherein X' is fluoro, chloro or bromo; —C≡C—C≡CR$_1$ wherein R$_1$ is hydrogen, methyl, or ethyl; —C≡COR$_2$ wherein R$_2$ is methyl or ethyl; wherein D is cis-C=C(R$_3$)—, trans-C=C(R$_3$) or —CH$_2$CH$_2$, wherein R$_3$ is hydrogen or fluoro; wherein Z is:

(1) —CH$_2$—(CH$_2$)$_f$—C(R$_4$)$_2$— wherein each R$_4$ is the same and is hydrogen or fluoro, and f is zero, one, 2 or 3;

(2) trans-CH$_2$—CH=CH—; or (3) —(Ph)—(CH$_2$)$_g$— wherein Ph is 1,2-, 1,3-, or 1,4-phenylene and g is zero, one, 2 or 3; with the proviso that when Z is —(Ph)—(CH$_2$)$_g$—, R$_3$ is hydrogen; wherein Q is (1) —COOR$_5$, wherein R$_5$ is
  (a) hydrogen,
  (b) (C$_1$-C$_{12}$)alkyl,
  (c) (C$_3$-C$_{10}$)cycloalkyl,
  (d) (C$_7$-C$_{12}$)aralkyl,
  (e) phenyl optionally substituted with one, 2 or 3 chloro or (C$_1$-C$_4$)alkyl,
  (f) phenyl substituted in the para-position with —NHCOR$_6$, —COR$_7$, —OC(O)R$_8$ or —CH=N—NHCONH$_2$, wherein R$_6$ is methyl, phenyl, acetamidophenyl, benzamidophenyl or —NH$_2$; R$_7$ is methyl, phenyl, —NH$_2$, or methoxy; and R$_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2-yl)-2-oxopropan-1-yl P-oxide, or
  (j) a pharmacologically acceptable cation;

(2) —CH$_2$OH;

(3) —COL$_2$, wherein L$_2$ is
  (a) amino group of the formula —NR$_9$R$_{10}$ wherein R$_9$ is hydrogen or (C$_1$-C$_{12}$)alkyl and R$_{10}$ is
    (i) hydrogen
    (ii) (C$_1$-C$_{12}$)alkyl
    (iii) (C$_3$-C$_{10}$)cycloalkyl,
    (iv) (C$_7$-C$_{12}$)aralkyl
    (v) phenyl optionally substituted with one, 2 or 3 chloro, (C$_1$-C$_3$)alkyl, hydroxy, carboxy, (C$_2$-C$_5$-)alkoxycarbonyl, or nitro,
    (vi) (C$_2$-C$_5$)carboxyalkyl,
    (vii) (C$_2$-C$_5$)carbamoylalkyl,
    (viii) (C$_2$-C$_5$)cyanoalkyl,
    (ix) (C$_3$-C$_6$)acetylalkyl,
    (x) (C$_7$-C$_{12}$)benzoalkyl, optionally substituted by one, 2, or 3 chloro, (C$_1$-C$_3$)alkyl, hydroxy, (C$_1$-C$_3$)alkoxy, carboxy, (C$_2$-C$_5$)-alkoxycarbonyl, or nitro,
    (ix) pyridyl, optionally substituted by one, 2, or 3 chloro, (C$_1$-C$_3$)alkyl, or (C$_1$-C$_3$)alkoxy,
    (xii) (C$_6$-C$_9$)pyridylalkyl optionally substituted by one, 2, or 3 chloro, (C$_1$-C$_3$)alkyl, hydroxy, or (C$_1$-C$_3$)alkyl,
    (xiii) (C$_1$-C$_4$)hydroxyalkyl,
    (xiv) (C$_1$-C$_4$)dihydroxyalkyl,
    (xv) (C$_1$-C$_4$)trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 (C$_1$-C$_{12}$)alkyl;
  (c) carbonylamino of the formula —NR$_{11}$COR$_{10}$, wherein R$_{11}$ is hydrogen or (C$_1$-C$_4$)alkyl and R$_{10}$ is other than hydrogen, but otherwise defined as above;
  (d) sulfonylamino of the formula —NR$_{11}$SO$_2$R$_{10}$, wherein R$_{11}$ and R$_{10}$ are defined in (c);

(4) —CH$_2$NL$_3$L$_4$, wherein L$_3$ and L$_4$ are hydrogen or (C$_1$-C$_4$)alkyl, being the same or different, or the pharmacologically acceptable acid addition salts thereof when Q is —CH$_2$NL$_3$L$_4$; or (5) —CN;

wherein s is the integer one or 2;

wherein L is H,H; $\alpha$-OR$_{12}$,$\beta$-H; $\alpha$-H,$\beta$-OR$_{12}$; $\alpha$-CH$_2$OR$_{12}$,$\beta$-H; $\alpha$-H,$\beta$-CH$_2$OR$_{12}$ wherein R$_{12}$ is hydrogen or a hydroxyl protective group;

wherein Y is trans —CH=CH—, cis-CH=CH—, —CH$_2$CH$_2$—, or —C≡C—;

wherein M is $\alpha$-OR$_{12}$,$\beta$-R$_{14}$; or $\alpha$-R$_{14}$,$\beta$-OR$_{12}$, wherein R$_{12}$ is as defined above, and R$_{14}$ is hydrogen or methyl;

wherein L$_1$ is $\alpha$-R$_{15}$,$\beta$-R$_{16}$; $\alpha$-R$_{16}$,$\beta$-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;

wherein R$_{17}$ is (1) —C$_m$H$_{2m}$CH$_3$ wherein m is an integer of from one to 5, (2) phenoxy optionally substituted by one, 2, or 3 chloro, fluoro, trifluoromethyl, (C$_1$-C$_3$)alkyl, or (C$_1$-C$_3$)alkoxy, with the proviso that not more than two substituents are other than alkyl and with the proviso that R$_{17}$ is phenoxy or substituted phenoxy, only when R$_{15}$ and R$_{16}$ are hydrogen or methyl, being the same or different;

(3) phenyl, benzyl, phenylethyl, or phenylpropyl optionally substituted on the aromatic ring by one, 2, or 3 chloro, fluoro, trifluoromethyl (C$_1$-C$_3$)alkyl, or (C$_1$-C$_3$)alkoxy, with the proviso that not more than two substituents are other than alkyl, (4) cis-CH=CH—CH$_2$CH$_3$, (5) —(CH$_2$)$_2$—CH(OH)—CH$_3$, (6) —(CH$_2$)$_3$—CH=C(CH$_3$)$_2$, (7) 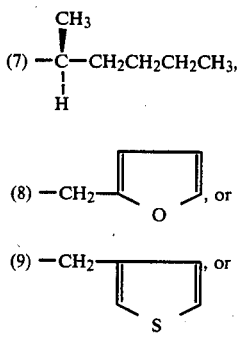

(8) , or (9) 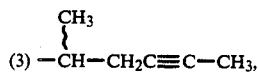, or wherein $$-\underset{L_1}{\overset{\parallel}{C}}-R_{17}$$

taken together is
(1) $(C_4-C_7)$cycloalkyl optionally substituted by one to 3 $(C_1-C_5)$-alkyl,
(2) 3-thienyloxymethyl, (3) $-CH-CH_2C\equiv C-CH_3$,
        $\mid$
        $CH_3$ (4) $-C\equiv C-C_qH_{2q}CH_3$ wherein q is an integer of from 2 to 6, or
(5) $-C_pH_{2p}CH=CH_2$ wherein p is an integer of from 3 to 7; and individual optical isomers thereof.

The compounds of Formulas V, VI and VII, which are useful as intermediates in the preparation of the compounds of Formula IV, are also a part of the present invention. In Formulas V, VI VII the substituent groups L, Y, M, $L_1$, $R_{17}$, s, Z, Q and R have the same meanings as defined in Formula IV. The group $L_{50}$ is the same as L only $R_{12}$ is other than hydrogen. The Group $R_{23}$ is the same as $R_{12}$ only $R_{23}$ is not hydrogen. The group $R_{54}$ is $-CN$, $-CH=CH_2$, $-CH_2OH$, $-C\equiv CH$, $-C\equiv CCF_3$, $-C\equiv CC_nH_{2n}CH_3$ wherein n is zero, one, 2 or 3, cis-$CH=CHC_nH_{2n}CH_3$, trans-$CH=CHC_nH_{2n}CH_3$ wherein n is zero, one, 2 or 3, $-C\equiv C-C\equiv C-R_1$ wherein $R_1$ is hydrogen, methyl, or ethyl, $-C\equiv C-OR_2$ wherein $R_2$ is methyl or ethyl or $-CH_2X$ wherein X is chloro or bromo. The group $R_{55}$ is the same as $R_{54}$ or is cis-$CH=CHX'$ wherein $X'$ is chloro, bromo or fluoro.

In the compounds of the present invention, and as used herein, (-----) denotes the α-configuration, (———) denotes the β-configuration, (~) denotes α- and/or β-configuration or the E and/or Z isomer.

With regard to the divalent groups described above, i.e., $M_n$, L and $L_1$ said divalent groups are defined in terms of an α-substituent and a β-substituent which means that the α-substituent of the divalent group is in the alpha configuration with respect to the plane of the C-8 to C-12 cyclopentane ring and the β-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety $L_2$ in the $-COL_2$ substituent group the definition $(C_1-C_{12})$alkyl means that $L_2$ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when $L_2$ represents, for example, $(C_2-C_5)$carboxyalkyl, the alkyl moiety thereof contains from 1 to 4 carbon atoms and is a straight chain or a branched chain alkyl group.

The compounds of the present invention exhibiting the olefinic double bond at C-5,6 positions are $CBA_2$ compounds, while compounds which are saturated at the C-5,6 positions are $CBA_1$ compounds.

Novel compounds wherein Z is $-(Ph)-(CH_2)_g-$ are designated inter-o-, inter-m-, or inter-p-phenylene depending on whether the attachment between C-5 and the $-(CH_2)_g-$ moiety is ortho, meta, or para, respectively. For those compounds wherein g is zero, one or 2, the carbacyclin analogs so described are further characterized as 2,3,4-trinor-, 3,4-dinor-, or 4-nor, since in this event the Q-terminated side chain contains (not including the phenylene) 2, 3, or 4 carbon atoms, respectively, in place of the five carbon atoms contained in $PGI_2$. The missing carbon atom or atoms are considered to be at the C-4 to C-2 positions such that the phenylene is connected to the C-5 and C-1 to C-3 positions. Accordingly these compounds are named as 1,5-, 2,5-, and 3,5-inter-phenylene-CBA compounds when g is zero, one, or 2, respectively and when g is 3 the compounds are named as 4,5-inter-phenylene-CBA compounds.

Those CBA analogs wherein Z is $-CH_2-(CH_2-)_f-C(R_4)_2-$ wherein $R_4$ is fluoro are characterized as "2,2-difluoro-" compounds. For those compounds wherein f is zero, 2, or 3, the carbacyclin analogs so described are further characterized as 2-nor, 2a-homo, or 2a,2b-dihomo, since in this event the Q-terminated side chain contains 4, 6, or 7 carbon atoms, respectively, in place of the five carbon atoms contained in $PGI_2$. The missing carbon atom is considered to be at the C-2 position such that the C-1 carbon atom is connected to the C-3 position. The additional carbon atom or atoms are considered as though they were inserted between the C-2 and C-3 positions. Accordingly these additional carbon atoms are referred to as C-2a and C-2b, counting from the C-2 to the C-3 position.

Those CBA analogs wherein Z is trans-$CH_2-CH=CH-$ are described as "trans-2,3-didehydro-CBA" compounds.

Those novel compounds where s is 2 are further characterized as 7a-homo-CBA compounds by virtue of the cyclohexyl ring replacing the heterocyclic ring of prostacyclin.

Further, all of the novel compounds of the present invention contain a substituent at the 9β-position and are named as 9β-substituted compounds.

When $R_3$ is fluoro, "5-fluoro-" compounds are described.

When R$_{14}$ is methyl, the carbacyclin analogs are all named as "15-methyl-" compounds. Further, except for compounds wherein Y is cis-CH=CH—, compounds wherein the M moiety contains an hydroxyl in the beta configuration are additionally named as "15-epi-" compounds.

For the compounds wherein Y is cis-CH=CH—, then compounds wherein the M moiety contains an hydroxyl in the alpha configuration are named as "15-epi-CBA" compounds. For a description of this convention of nomenclature for identifying C-15 epimers, see U.S. Pat. No. 4,016,184, issued Apr. 5, 1977, particularly columns 24–27 thereof.

The novel carbacyclin analogs herein which contain —(CH$_2$)$_2$—, cis-CH=CH—, or —C≡C— as the Y moiety, are accordingly referred to as "13,14-dihydro", "cis-13", or "13,14-didehydro" compounds, respectively.

When R$_{17}$ is straight chained —C$_m$H$_{2m}$—CH$_3$, wherein m is an integer of from one to 5, the compounds so described are named as "19,20-dinor", "20-nor", "20-methyl" or "20-ethyl" compounds when m is one, 2, 4 or 5, respectively. When R$_{17}$ is branched chain —C$_m$H$_{2m}$—CH$_3$, then the compounds so described are "17-, 18-, 19-, or 20-alkyl" or "17,17-, 17,18-, -17,19-, 17,20-, 18,18-, 18,19-, 18,20-, 19,19-, or 19,20-dialkyl" compounds when m is 4 or 5 and the unbranched portion of the chain is at least n-butyl, e.g., "17,20-dimethyl" compounds are described when m is 5 (1-methylpentyl).

When R$_{17}$ is phenyl and neither R$_{15}$ nor R$_{16}$ is methyl, the compounds so described are named as "16-phenyl-17,18,19,20-tetranor" compounds. When R$_{17}$ is substituted phenyl, the corresponding compounds are named as "16-(substituted phenyl)-17,18,19,20-tetranor" compounds. When one and only one of R$_{15}$ and R$_{16}$ is methyl or both R$_{15}$ and R$_{16}$ are methyl, then the corresponding compounds wherein R$_{17}$ is as defined in this paragraph are named as "16-phenyl or 16-(substituted phenyl)-18,19,20-trinor" compounds or "16-methyl-16-phenyl- or 16-(substituted phenyl)-18,19,20-trinor" compounds respectively.

When R$_{17}$ is benzyl, the compounds so described are named as "17-phenyl-18,19,20-trinor" compounds. When R$_{17}$ is substituted benzyl, the corresponding compounds are named as "17-(substituted phenyl)-18,19,20-trinor" compounds.

When R$_{17}$ is phenylethyl, the compounds so described are named as "18-phenyl-19,20-dinor" compounds. When R$_{17}$ is substituted phenylethyl, the corresponding compounds are named as "18-(substituted phenyl)-19,20-dinor" compounds.

When R$_{17}$ is phenylpropyl, the compounds as described are named as "19-phenyl-20-nor" compounds. When R$_{17}$ is substituted phenylpropyl the corresponding compounds are named as "19-(substituted phenyl)-20-nor" compounds.

When R$_{17}$ is phenoxy and neither R$_{15}$ nor R$_{16}$ is methyl, the compounds so described are named as "16-phenoxy-17,18,19,20-tetranor" compounds. When R$_{17}$ is substituted phenoxy, the corresponding compounds are named as "16-(substituted phenoxy)-17,18,19,20-tetranor" compounds. When one and only one of R$_{15}$ and R$_{16}$ is methyl or both R$_{15}$ and R$_{16}$ are methyl, then the corresponding compounds wherein R$_{17}$ is as defined in this paragraph are named as "16-phenoxy or 16-(substituted phenoxy)-18,19,20-trinor" compounds or "16-methyl-16-phenoxy- or 16-(substituted phenoxy)18,19,20-trinor" compounds, respectively.

When R$_{17}$ is cis-CH=CH—CH$_2$CH$_3$, the compounds so described are named as "cis-17,18-didehydro" compounds.

When R$_{17}$ is —(CH$_2$)$_2$—CH(OH)—CH$_3$, the compounds so described are named as "19-hydroxy" compounds.

When R$_{17}$ is —(CH$_2$)$_3$—CH=C(CH$_3$)$_2$, the compounds so described are named as "20-isopropylidene" compounds.

When R$_{17}$ is

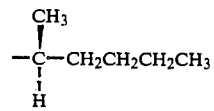

the compounds so described are named as 17(S),20-dimethyl compounds.

When R$_{17}$ is 2-furylmethyl or 3-thienylmethyl, i.e.,

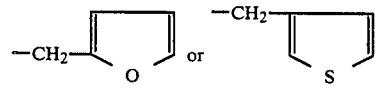

respectively the compounds so described are named as "17-(2-furyl)-18,19,20-trinor" compounds and "17-(3-thienyl)-18,19,20-trinor" compounds respectively.

When —C(L$_1$)—R$_{17}$ is

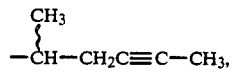

the compounds are named as "16-(R,S)methyl-18,19-tetradehydro" compounds.

When —C(L$_1$)—R$_{17}$ is optionally substituted cycloalkyl or 3-thienyloxymethyl, the compounds so described are named respectively 15-cycloalkyl-16,17,18,19,20-pentanor compounds and 16-(3-thienyl)oxy-17,18,19,20-tetranor compounds. The term 3-thienyloxymethyl means the moiety having the structure:

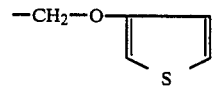

When —C(L$_1$)R$_{17}$ is —C≡C—C$_q$H$_{2q}$CH$_3$ wherein q is an integer of from 2 to 6 the compounds so described are named as "16,17-tetradehydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When —C(L$_1$)R$_{17}$ is —C$_p$H$_{2p}$CH=CH$_2$ wherein p is an integer of from 3 to 7 the compounds so described are named as "19,20-didehydro", "19,20-didehydro-18a,18b-dihomo", "19,20-didehydro-18a,18b,18c-trihomo", "19,20-didehydro-18a,18b,18c,18d-tetrahomo" compounds as the integer represented by p varies from 3 to 7 respectively.

When —C(L₁)R₁₇ is

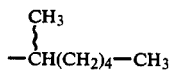

the compounds so described are named as "16(R,S),20-dimethyl" compounds.

When at least one of R₁₅ and R₁₆ is not hydrogen then (except for the 16-phenoxy or 16-phenyl compounds discussed above) there are described the "16-methyl" (one and only one of R₁₅ and R₁₆ is methyl), "16,16-dimethyl" (R₁₅ and R₁₆ are both methyl), "16-fluoro" (one and only one of R₁₅ and R₁₆ is fluoro), "16,16-difluoro" (R₁₅ and R₁₆ are both fluoro) compounds. For those compounds wherein R₁₅ and R₁₆ are different, the carbacyclin analogs as represented contain an asymmetric carbon atom at C-16. Accordingly, two epimeric configurations are possible: "(16S)" and "(16R)". Further, there is described by this invention the C-16 epimeric mixture: "(16RS)".

When Q is —CH₂OH, the compounds so described are named as "2-decarboxy-2-hydroxymethyl" compounds.

When Q is —CH₂NL₃L₄, the compounds so described are named as "2-decarboxy-2-aminomethyl" or "2-(substituted amino)methyl" compounds.

When Q is —COL₂, the novel compounds herein are named as amides. Further, when Q is —COOR₅ and R₅ is other than hydrogen the novel compounds herein are named as esters and salts.

When Q is CN the novel compounds herein are named as 2-decarboxy-2-cyano compounds.

The "C$_n$H$_{2n}$CH₃" moiety of 9β-substituent groups —C≡CC$_n$H$_{2n}$CH₃ and cis-CH=CHC$_n$H$_{2n}$CH₃ or trans-CH=CHC$_n$H$_{2n}$CH₃ wherein m is zero, one, 2 or 3 represents not only a straight chain alkyl group of from one to 4 carbon atoms but also, when n is 2 or 3, represents a branched alkyl group of 3 or 4 carbon atoms, i.e., isopropyl, isobutyl or tert-butyl.

Examples of phenyl esters substituted in the para position (i.e., Q is —COOR₅, R₅ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is —COL₂) include the following:

(1) Amides within the scope of alkylamino groups of the formula -NR₉R₁₀ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tertbutylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylproylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula $-NR_{11}COR_{10}$ are methylcarbonylamide, ethylcarbonylamide, phenylcarbonylamide, and benzylcarbonylamide.

(4) Amides within the scope of sulfonylamino of the formula $-NR_{11}COR_{10}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tertbutyl, isopentyl, neopentyl, butyl, pentyl, hexyl, heptyl, octyl, nonyl, decyl, undecyl, dodecyl, isomeric forms thereof.

Examples of $(C_3-C_{10})$cycloalkyl which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tertbutylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of $(C_7-C_{12})$aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

Examples of $(C_4-C_7)$cycloalkyl optionally substituted by one to 3 $(C_1-C_5)$alkyl are cyclobutyl, 1-propylcyclobutyl, 1-butylcyclobutyl, 1-pentylcyclobutyl, 2-methylcyclobutyl, 2-propylcyclobutyl, 3-ethylcyclobutyl, 3-propylcyclobutyl, 2,3,4-triethylcyclobutyl, cyclopentyl, 2,2-dimethylcyclopentyl, 3-ethylcyclopentyl, 3-propylcyclopentyl, 3-butylcyclopentyl, 3-tert-butylcyclopentyl, 1-methyl-3-propylcyclopentyl, 2-methyl-3-propylcyclopentyl, 2-methyl-4-propylcyclopentyl, cyclohexyl, 3-ethylcyclohexyl, 3-isopropylcyclohexyl, 4-methylcyclohexyl, 4-ethylcyclohexyl, 4-propylcyclohexyl, 4-butylcyclohexyl, 4-tert-butylcyclohexyl, 2,6-dimethylcyclohexyl, 2,2-dimethylcyclohexyl, 2,6-dimethyl-4-propylcyclohexyl, and cycloheptyl.

Examples of substituted phenoxy, phenyl, phenylmethyl, i.e., benzyl, phenylethyl, or phenylpropyl of the $R_{17}$ moiety are (o-, m-, or p-)tolyl, (o-, m-, or p-)ethylphenyl, 4-ethyl-o-tolyl, 5-ethyl-m-tolyl, (o-, m-, p-)propylphenyl, 2-propyl-(m- or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(m- or p-)tolyl, 4-fluoro-2,5-xylyl, (2,4-, 2,5-, 2,6-, 3,4-, or 3,5-)difluorophenyl, (o-, m-, or p-

)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6)methylphenyl, (o-, m-, or p-)tolyloxy, (o-, m-, or p-)ethylphenyloxy, 4-ethyl-o-tolyloxy, 5-ethyl-m-tolyloxy, (o-, m-, or p-)propylphenoxy, 2-propyl-(m- or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(m- or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3, 4, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenyl methyl, 4-ethyl-o-tolylmethyl, 5-ethyl-m-tolylmethyl, (o-, m-, or p-)propylphenylmethyl, 2-propyl-(m- or p-)tolylmethyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(m- or p-)tolylmethyl, 4-fluoro-2,5-xylylmethyl, (2,4-, 2,5-, 2,6-, 3,4-, or 3,5-)difluorophenylmethyl, (o-, m-, or p-)tolylethyl, (o-, m-, or p-)ethylphenylethyl, 4-ethyl-o-tolylethyl, 5-ethyl-m-tolylethyl, (o-, m-, or p-)propylphenylethyl, 2-propyl-(m- or p-)tolylethyl, 4-isopropyl-2,6-xylylethyl, 3-propyl-4-ethylphenylethyl, (2,3,4-, 2,3,5-, 2,3,6-, or 2,4,5-)trimethylphenylethyl, (o-, m-, or p-)fluorophenylethyl, 2-fluoro-(m- or p-)tolylethyl, 4-fluoro-2,5-xylylethyl, (2,4-, 2,5-, 2,6-, 3,4-, or 3,5-)difluorophenylethyl, (o-, m-, or p-)chlorophenylmethyl, 2-chloro-p-tolylmethyl, (3, 4, 5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl, (o-, m-, or p-)chlorophenylpropyl, 2-chloro-p-tolylpropyl, (3, 4, 5, or 6-)chloro-o-tolylpropyl, 4-chloro-2-propylphenylpropyl, 2-isopropyl-4-chlorophenylpropyl, 4-chloro-3,5-xylylpropyl, (2,3-, 2,4-, 2,5-, 2,6-, 3,4-, or 3,5-)dichlorophenylpropyl, 4-chloro-3-fluorophenylpropyl, (3- or 4-)chloro-2-fluorophenylpropyl, (o-, m-, or p-)trifluoromethylphenylpropyl, (o-, m-, or p-)methoxyphenylpropyl, (o-, m-, or p-)ethoxyphenylpropyl, (4- or 5-)chloro-2-methoxyphenylpropyl, and 2,4-dichloro-(4- or 6-)methoxyphenylpropyl.

The group —$C_mH_{2m}CH_3$ wherein m is an integer of from one to 5 which $R_{17}$ may be represents straight or branched alkyl$C_1$–$C_5$ groups such as named hereinabove.

The terms phthalidyl; 3-(5,5-dimethyl-1,3,2-dioxaphosphorinan-2-yl)-2-oxopropan-1-yl P-oxide; and 3-(5,5-di(hydroxymethyl)-1,3,2-dioxaphosphorinan-2-yl)-2-oxopropan-1-yl P-oxide; which $R_5$ may represent in the —COOR$_5$ group mean the following respective moieties (a), (b) and (c):

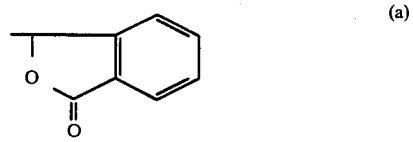
(a)

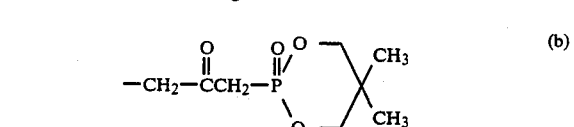
(b)

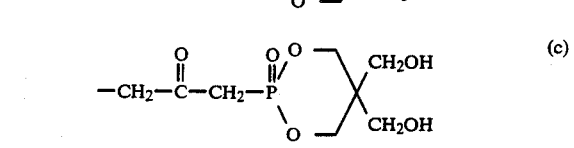
(c)

As indicated hereinabove $R_{12}$ is hydrogen or a protecting group. Those protective groups within the scope of $R_{12}$ are any group which replaces a hydroxy hydrogen and is neither attacked by nor is reactive to the reagents used in the transformations used herein as a hydroxy is and which is subsequently replaceable by hydrolysis with hydrogen in the preparation of the carbacyclin-type compounds. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pp. 51–79 (1969). Those blocking groups which have been found useful include:

(a) tetrahydropyranyl;
(b) tetrahydrofuranyl;
(c) a group of the formula —$C(OR_{24})(R_{1-8})$—$CH(R_{19})(R_{20})$, wherein $R_{24}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{18}$ and $R_{19}$ are alkyl of one to 4 carbon atoms, inclusive, phenyl, phenyl substituted with one, 2 or 3 alkyl of one to 4 carbon atoms, inclusive, or when $R_{18}$ and $R_{19}$ are taken together —$(CH_2)_a$— or when $R_{18}$ and $R_{19}$ are taken together to form —$(CH_2)_b$—O—$(CH_2)_c$, wherein a is 3, 4, or 5 and b is one, 2, or 3, and c is one, 2, or 3, with the proviso that b plus c is 2, 3, or 4, with the further proviso that $R_{18}$ and $R_{19}$ may be the same or different, and wherein $R_{20}$ is hydrogen or phenyl; and (d) silyl groups according to $R_{21}$, as qualified hereinafter.

When the protective group $R_{12}$ is tetrahydropyranyl, and tetrahydropyranyl ether derivative of any hydroxy moieties of the CBA-type intermediates herein is obtained by reaction of the hydrogen-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the $R_{12}$ protective group is tetrahydrofuranyl, 2,3-dihydrofuran is used, as described in the preceding paragraph, in place of the 2,3-dihydropyran.

When the $R_{12}$ protective group is of the formula —C(OR$_{24}$)(R$_{18}$)—CH(R$_{19}$)(R$_{20}$), wherein $R_{24}$, $R_{18}$, $R_{19}$, and $R_{20}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

$R_{21}$ is a silyl protective group of the formula —Si(G$_1$)$_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of —Si(G$_1$)$_3$ include trimethylsilyl, dimethylphenylsilyl, triphenylsilyl, t-butyldimethylsilyl, or methylphenylbenzylsilyl. With regard to G$_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to $R_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by $R_{12}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

$R_{13}$ is a hydroxyl protective group, as indicated above. As such, $R_{13}$ may be an acyl protective group according to $R_{22}$ as defined below, an acid hydrolyzable protective group according to $R_{12}$ as defined above, or a silyl protective group according to $R_{21}$ as defined above.

Acyl protective groups according to $R_{22}$ include:

(a) benzoyl;

(b) benzoyl substituted with one to 5 alkyl of one to 4 carbon atoms, inclusive, or phenylalkyl of 7 to 12 carbon atoms, inclusive, or nitro, with the proviso that not more than two substituents are other than alkyl, and that the total number of carbon atoms in the substituents does not exceed 10 carbon atoms, with the further proviso that the substituents are the same or different;

(c) benzoyl substituted with alkoxycarbonyl of 2 to 5 carbon atoms, inclusive;

(d) naphthoyl;

(e) naphthoyl substituted with one to 9, inclusive, alkyl of one to 4 carbon atoms, inclusive, phenylalkyl of 7 to 10 carbon atoms, inclusive, or nitro, with the proviso that not more than two substituents on either of the fused aromatic rings are other than alkyl and that the total number of carbon atoms in the substituents on either of the fused aromatic rings does not exceed 10 carbon atoms, with the further proviso that the various substitutents are the same or different; or (f) alkanoyl of 2 to 12 carbon atoms, inclusive.

In preparing these acyl derivatives of a hydroxy-containing compound herein, methods generally known in the art are employed. Thus, for example, an aromatic acid of the formula R$_{22}$OH, wherein $R_{22}$ is as defined above (e.g., R$_{22}$OH is benzoic acid), is reacted with the hydroxy-containing compound in the presence of a dehydrating agent, e.g. p-toluensulfonyl chloride or dicyclohexylcarbodiimide; or alternatively an anhydride of the aromatic acid of the formula (R$_{22}$)OH, e.g., benzoic anhydride, is used.

Preferably, however, the process described in the above paragraph proceeds by use of the appropriate acyl halide, e.g., R$_{22}$Hal, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_{22}$, the following compounds are available as acids (R$_{22}$OH), (R$_{22}$)$_2$O, or acyl chlorides (R$_{22}$Cl): benzoyl; substituted benzoyl, e.g., (2-, 3-, or 4-)methylbenzoyl, (2-, 3-, or 4-)ethylbenzoyl, (2-, 3-, or 4-)isopropylbenzoyl, (2-, 3-, or 4-)tertbutylbenzoyl, 2,4- dimethylbenzoyl, 3,5-dimethylbenzoyl, 2-isopropyltoluyl, 2,4,6-trimethylbenzoyl, pentamethylbenzoyl, phenyl(2-, 3-, or 4-)toluyl, (2-, 3-, or 4-)phenethylbenzoyl, (2-, 3-, 4-)nitrobenzoyl, (2,4, 2,5-, or 2,3-)dinitrobenzoyl, 2,3-dimethyl-2-nitrobenzoyl, 4,5-dimethyl-2-nitrobenzoyl, 2-nitro-6-phenylethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7-, or 8-)-methyl-1-naphthoyl, 4-ethyl-2-naphthoyl, and (5- or 8-)nitro-2-naphthoyl and acetyl.

There may be employed, therefore, benzoyl chloride, 4-nitrobenzoyl chloride, 3,5-dinitrobenzoyl chloride, or the like, i.e. $R_{22}Cl$ compounds corresponding to the above $R_{22}$ groups. If the acyl chloride is not available, it is prepared from the corresponding acid and phosphorus pentachloride as is known in the art. It is preferred that the $R_{22}OH$, $(R_{22})_2O$, or $R_{22}Cl$ reactant does not have bulky hindering substituents, e.g. tert-butyl on both of the ring carbon atoms adjacent to the carbonyl attaching site.

The acyl protective groups, according to $R_{22}$, are removed by deacylation. Alkali metal carbonate or hydroxide are employed effectively at ambient temperature for this purpose. For example, potassium carbonate or hydroxide in aqueous methanol at about 25° C. is advantageously employed.

The novel CBA analogs disclosed herein wherein $R_{12}$ is hydrogen produce certain prostacyclin-like pharmacological responses.

Accordingly, the novel formula IV compounds wherein $R_{12}$ is hydrogen CBA analogs are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and additionally the compounds wherein s is one and R is other than —CH$_2$OH are useful as antithrombotic agents as indicated below.

(a) Platelet Aggregation Inhibition

The compounds of formula IV wherein R is other than —CH$_2$OH, $R_{12}$ is hydrogen, and s is one are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, ateriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2-4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg per ml of whole blood. These compounds, i.e., the compounds of formula IV wherein R is other than —CH$_2$OH, $R_{12}$ is hydrogen, and s is one are useful in the treatment of peripheral vascular diseases, in the same manner as described in U.S. Pat. No. 4,103,026.

(b) Gastric Secretion Reduction

Compounds of Formula IV wherein $R_{12}$ is hydrogen are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 μg to about 20 μg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula IV wherein $R_{12}$ is hydrogen are also useful in reducing the undesirable gastrointestinal effects resulting from systemic administration of anti-inflammatory prostaglandin synthetase inhibitors, and are useful for that purpose by concomitant administration of said compounds of Formula IV and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula IV compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula IV wherein $R_{12}$ is hydrogen are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formula IV compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula IV compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Suitable means to employ the aerosol inhalation therapy technique are described fully in U.S. Pat. No. 3,868,691, for example.

When Q is —COOR$_5$, the novel Formula IV compounds so described are used for the purposes described above in the free acid form, in ester form, or in pharmacologically acceptable salt form. When the ester form is used, the ester is any of those within the above definition of $R_5$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula IV for the purposes described above are those with pharmacologically acceptable metal cations, ammonia, amine cations, or quaternary ammonium cations. Illustrative pharmacological acceptable cations which $R_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicylohexylamine, benzylamine, dibenzylamine, α-phenylethylamine, β-phenylethylamine, ethylenediamine, diethylenetriamine, adamantylamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is —$CH_2NL_3L_4$, the Formula IV compounds so described are used for the purposes described in either free base or pharmacologically acceptable acid addition salt form.

The acid addition salts of the 2-decarboxy-2-aminomethyl- or 2-(substituted aminomethyl)-Formula IV compounds provided by this invention are, for example, the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the appropriate compound of Formula IV with the stoichiometric amount of the acid corresponding to the pharmacologically acceptable acid addition salt.

The compounds of Formula IV wherein R is —$CH_2OH$ are also useful as intermediates in the preparation of the corresponding compounds wherein R is —CHO as will be apparent from the chemical preparations described hereinbelow. Also, the compounds of Formula IV wherein $R_{12}$ is a hydroxyl protecting group are useful as intermediates to the compounds of Formula IV wherein $R_{12}$ is hydrogen.

To obtain the optimum combination of biological response specificity, potency, and duration of activity, certain compounds within the scope of this invention are preferred. Preferred compounds of the present invention are the $CBA_2$ analogs, i.e., the compounds of Formula IV wherein the C-5,6 position is unsaturated, and of these compounds those wherein Y is —$CH_2CH_2$—, —C≡C— or trans-CH=CH— and/or Q is —$COOR_5$ or —$COL_2$ are preferred especially when $R_5$ is hydrogen, methyl, ethyl, or a pharmacologically acceptable cation such as sodium, and when each of $R_9$ and $R_{10}$ of the $L_2$ substituent moiety is hydrogen. Of these preferred compounds those wherein $R_3$ is hydrogen are more preferred. To further characterize the preferred embodiments of the present invention, compounds of Formula IV wherein $R_{17}$ is —$C_mH_{2m}CH_3$, benzyl, phenoxy, 3-thienylmethyl, or phenyl or wherein —C($L_1$)$R_{17}$ taken together is cyclohexyl, 3-thienyloxymethyl or 3-ethylcyclobutyl, or —CH(~$CH_3$)CH$_2$C≡$CCH_3$ are especially preferred. Also compounds wherein $R_{17}$ is $C_mH_{2m}CH_3$ and each of $R_{15}$ and $R_{16}$, which make up the $L_1$ substituent, are fluoro are especially preferred. Of all the preferred compounds described herein those compounds wherein R represents —C≡CH, —CH=$CH_2$, —CN, —CHO, or —C≡C—$CnH_{2n}CH_3$ are more particularly preferred with those compounds wherein R is —C≡CH, —CH=$CH_2$, —CN or —C≡C—CnHhd 2nCH$_3$ wherein n is zero, one or 2 being the most particularly preferred. The Formula IV compounds of the specific examples, of course, represent preferred compounds of the present invention and in particular the following are preferred: (5Z)-9β-cyano-6a-carba-prostaglandin $I_2$; (5Z)-9β-formyl-6a-carba-prostaglandin $I_2$; (5Z)-9β-vinyl-6a-carba-prostaglandin $I_2$; (5Z)-9β-(1-pentynyl)-6a-carba-prostaglandin $I_2$; and (5Z)-9β-ethynyl-6a-carba-prostaglandin $I_2$ and (5Z)-9β-ethynyl-16-methyl-18,19-tetradehydro-6a-carba-prostaglandin $I_2$.

Preferred for biological potency are formula IV $CBA_2$ analogs exhibiting the same C-5 isomeric configuraton as $CBA_2$ itself. As is apparent from the foregoing as compounds satisfy more of the above preferences, said compounds are more preferred.

The carbacyclin analogs of the present invention as represented by Formula IV are prepared by various procedures which are all generally known in the art. The various charts provided herein are useful in illustrating the preparation of the compounds.

In each of the charts the substituent groups s, L, M, Y, $L_1$, $R_{17}$, Q, X and X' have the meanings defined in Formula IV and $R_{21}$ is a silyl protecting group as defined hereinabove. The group $R_{50}$ (Chart A and Chart F) is —CN; —CH=$CH_2$; —$CH_2OH$; —C≡CH; —C≡$CCF_3$; —C≡$CC_nH_{2n}CH_3$ wherein n is zero, one, 2 or 3; cis-CH=$CHC_nH_{2n}CH_3$ of trans-CH=$CHC_nH_{2n}CH_3$ wherein n is zero, one, 2 or 3; —C≡C—C≡C—$R_1$ wherein $R_1$ is hydrogen, methyl or ethyl; or —C≡$COR_2$ wherein $R_2$ is methyl or ethyl. The group $R'_{50}$ (Chart B) is —$CH_2X$ or has the same meaning as $R_{50}$ only $R'_{50}$ is not —CN. The group $R_{51}$ (Chart F and Chart G) is —$CH_2X$ or has the same meaning as $R_{50}$. The group $Z_1$ has the same meaning as Z except $Z_1$ other than —(Ph)—($CH_2$)$_g$—. The group Q' has the same meaning as Q except Q' is not —COOH. The group $Q_2$ is the same as the group Q except $Q_2$ is other than —$CH_2OH$.

As indicated hereinabove the hydroxyl groups at positions C-11 and C-15 of the compounds of the present invention may be protected by various groups generally employed in the art and protection of the hydroxyl functions and is generally desirable or necessary during the preparation of the compounds. Although any of the various protecting groups described herein may be employed those preferred are tetrahydropyranyl (THP) and tert-butyldimethylsilyl. Particularly, THP is a preferred protecting group during the various reactions required to add the side chains and t-butyldimethylsilyl is a preferred group to employ during separation of the isomers. Of course it may be useful or desirable to utilize protecting groups which may be selectively hydrolyzed. Also, when $R_{17}$ is —($CH_2$)$_2$CH(OH)—$CH_3$ the hydroxyl group at C-19 generally is protected by the same type of groups utilizd to protect the C-11 and C-15 hydroxyl groups during the preparation of said compounds and subsequently deprotected by hydrolysis as described herein.

Also, it will be apparent that in the preparation of the compounds the 5(E) and 5(Z) isomers generally may be separated when the C-11 and C-15 hydroxyl groups are either protected or are unprotected. However, it has been found that protection of these hydroxyl groups with, e.g., tert-butyldimethyl silyl often facilitates clean separation of the isomers in high yield. Separation of the 5(E) and 5(Z) isomers is achieved by conventional means, typically column chromatography is employed.

Referring to Chart A wherein there is represented schematically the preparation of certain 9β-substituted compounds (Formula A-2) which are novel intermediates useful in preparing the Formula IV compounds and which are regarded as part of the present invention. The enones of Formula A-1 are known in the art or are prepared by procedures known in the art as generally described hereinbelow.

Introduction of the $R_{50}$ group at the 9β-position is achieved by various means. When $R_{50}$ is —CN the enone of Formula A-1 is subjected to hydrocyanation using, for example, potassium cyanide, 18-crown-6, and acetone cyanohydrin as generally described by C. L. Liotta, et al, Tetrahedron Lett. 1117 (1977). Molar equivalents of the enone (A-1) and acetone cyanohydrin are employed and the potassium cyanide and 18-crown-6 serve as catalysts for the very gradual decomposition of the acetone cyanohydrin to HCN and acetone. When $R_{50}$ is —CH$_2$OH the enone (A-1) is subjected to photochemical addition of methanol by the procedure generally described by G. L. Bundy, Tetrahedron Lett. 1957 (1975) to give compounds of Formula A-2 wherein $R_{50}$ is —CH$_2$OH. The thus obtained 9β—CH$_2$OH substituted compound of Formula A-2 can be converted to the corresponding 9β—CH$_2$X substituted derivative of Formula A-3 by the general method described by J. B. Lee and T. J. Nolan, Can. J. Chem., 44, 1331 (1966) whereby the hydroxymethyl group is treated with an excess of triphenylphosphine in carbontetrachloride when X is Cl or carbontetrabromide when X is Br. The intermediates of Formula A-3 also are a part of the present invention. To obtain compounds of Formula A-2 wherein $R_{50}$ is —C≡CH a variation of the procedure of J. Schwartz (R. T. Hanson, et al, J. Am. Chem. Soc., 100, 12244 (1978)) is employed. Lithiotrimethylsilylacetylide is prepared by the general method of A. B. Holmes, et al, J.C.S. Chem. Commun., 840 (1978) using bis(trimethylsilyl)acetylene (BTMSA) and methyllithium in tetrahydrofuran (THF). The THF is evaporated, diethyl ether is added, then the acetylide is treated with diethylaluminum chloride to give trimethylsilyl diethylaluminumacetylide, which is added to a solution of 10% nickel-1,4-pentanedionate and diisobutylaluminum hydride (1:1). The enone (A-1) is then added to the resulting mixture to give the 9β-substituted trimethylsilylacetylene derivative from which the trimethyl silyl protecting group is removed by, for example, potassium fluoride hydrolysis in dimethylformamide (DMF) as generally described by E. J. Corey, et al, Tetrahedron Lett., 3963 (1973). The intermediates of Formula A-2 wherein $R_{50}$ is —C≡CC$_n$H$_{2n}$CH$_3$, —C≡C—C≡CR$_1$, —C≡C—OR$_2$ or —C≡CCF$_3$ are prepared in a similar manner using the appropriate lithioacetylide, for example, when $R_{50}$ is —C≡CC$_n$H$_{2n}$CH$_3$ and n is 2 using the lithio anion of 1-pentyne formed by treating 1-pentyne with n-butyllithium followed by treatment with diethylaluminum chloride. Or when R is —C≡CCF$_3$ the anion prepared from trifluoromethylacetylene (prepared as described by Finnegan and Morris, J. Org. Chem. 28, 1139 (1963)) is used. The reagents employed to prepare compounds wherein $R_{50}$ is —C≡CC$_n$H$_{2n}$CH$_3$, —C≡C—OR$_2$, —C≡C—C≡CR$_1$, or —C≡CCF$_3$ are commercially available or are prepared by procedures known in the art.

Intermediates of Formula A-2 wherein $R_{50}$ is —CH═CH$_2$ are prepared by the addition of lithium divinyl cuprate or a copper catalyzed vinyl Grignard to the enone (A-1) by procedures known in the art. Formula A-2 intermediates wherein $R_{50}$ is cis-CH═CHC$_n$H$_{2n}$CH$_3$ or trans-CH═CHC$_n$H$_{2n}$CH$_3$ are prepared by adding the appropriate cis- or trans-alkenyl cuprate to the enone (A-1) by well known procedures. The appropriate alkenyl cuprate is prepared for example by the general procedure described by F. Naso, et al., J.C.S. Chem. Commun. 523 (1981).

The compounds of Formula A-2 and A-3 are utilized to prepare novel compounds of Formula IV wherein D is —C═C(~R$_3$)— and R$_3$ is hydrogen as represented in Chart B. The compounds of Formula A-2 wherein $R_{50}$ is other than CN and compounds of Formula A-3 are subjected to a Wittig reaction using an appropriate triphenylphosphorane of Formula B-1 by procedures known in the art, then if desired the hydroxyl protecting groups which are present at C-11, C-15 or C-19 are removed by hydrolysis as generally described hereinabove to give compounds of Formula B-2. The compounds of Formula B-2 are used to prepare the Formula B-3 compounds wherein Q' is the same as Q except it is other than —COOH. The acids of Formula B-2 can be esterified or converted to an amide derivative by conventional means. The Formula B-2 acids or an ester thereof can be reduced to the corresponding alcohol, i.e., Formula B-3 wherein Q' is —CH$_2$OH by standard procedures, e.g., by refluxing with lithium aluminum hydride in an ether solvent. The alcohol thus obtained can be oxidized to the corresponding carboxaldehyde which upon treatment with a salt of hydroxylamine gives the oxime which is dehydrated to give the nitrile, i.e., the compounds of Formula B-3 wherein Q' is CN. These conversions are all carried out by procedures generally known in the art. See, for example, the aforementioned British specifications which describe the synthesis of various carbacyclin compounds, and in particular G.B. No. 2,013,661. The amide thus obtained can be reduced to the corresponding amines, i.e., compounds of Formula B-3 wherein Q' is —CH$_2$L$_3$L$_4$ by using, e.g., lithium aluminum hydride. See U.S. Pat. No. 4,073,808. Of course during the conversion of the Formula B-2 acids to the various other C-1 position derivatives as represented by Formula B-3, the C-11 and C-15 hydroxyl groups and when present the C-19 hydroxyl groups and if $R_{50}$ is CH$_2$OH are protected as described herein which groups can ultimately be deprotected by hydrolysis.

The 5(E) and 5(Z) isomers can be separated using either the compound of Formula B-2 or Formula B-3. However, to obtain the individual 5(E) and 5(Z) isomers of the compounds of Formula B-3 wherein R'$_{50}$ is —CH$_2$OH it is preferred that the Formula B-2 compound wherein R'$_{50}$ is —CH$_2$OH is esterified to a C$_1$-carboxylic acid ester.

The compounds of Formula A-2 wherein $R_{50}$ is —CN are used to prepare the 9β—CN substituted compounds of Formula IV wherein D is —C≡C($\sim R_3$) and $R_3$ is hydrogen as illustrated in Chart C. The Formula A-2 ($R_{50}$=CN) compound is treated with the dianion of the formula LiOC(=O)CH(Li)—$Z_1$—CH$_2$O$R_{21}$ (Formula C-1) by methods known in the art. See, for example, G. W. Moersch, J. Org. Chem. 36, 1149 (1979) and J. Mulzer, et al., Tetrahedron Lett. 2949 (1978). The dianion compounds are known in the art or are prepared by procedures known in the art. For example, see the illustrative procedure set forth in Example 2 hereof. The 6-hydroxy substituted compound of Formula C-2 is subjected to decarboxylative dehydration using dimethylformamide dineopentyl acetal by generally known procedures, e.g., see A. Eschenmoser, et al., Helv. Chim. Acta. 58 1450 (1975); S. Hara, et al., Tetrahedron Lett. 1545 (1975) and J. Mulzer, et al., Tetrahedron Lett. 2953 (1978) and 1909 (1979). Selective hydrolysis of Formula C-3 compounds to remove the silyl ether protecting group $R_{21}$ gives compounds of Formula C-4 which if desired are further hydrolyzed to remove any protecting groups which may be present at positions C-11, C-15 or C-19. Also, the alcohol of Formula C-4 is used to prepare the compounds of Formula C-5 wherein $Q_2$ is the same as Q except it is other than —CH$_2$OH. The Formula C-4 compounds can be oxidized, e.g., using Jones reagent, to the corresponding carboxylic acid which in turn can be converted to the esters and amides of Formula C-5. The amides can be reduced to the amines of Formula C-5, i.e., where $Q_2$ is —CH$_2$L$_3$L$_4$, and the alcohol can be oxidized to the carboxaldehyde then converted to the nitrile via the oxime. The general procedures are the same as those described hereinabove in connection with Formula B-3.

The compounds of Formula B-2 wherein $R'_{50}$ is —CH$_2$OH or the individual 5(E) and 5(Z) isomers are useful in preparing the compounds of Formula IV wherein R is —CH$_2$X or —CHO. In preparing the Formula IV compounds wherein R is —CH$_2$X wherein X is chloro or bromo the 9 methanol compound of Formula B-2 is converted to a C-1 position carboxylic acid ester then treated with a large excess of triphenylphosphine in refluxing carbon tetrachloride (X=Cl) or carbon tetrabromide (X=Br) according to the procedures generally described by J. B. Lee and T. J. Nolan, Can. J. Chem. 44, 1331 (1966). It is preferred that somewhat more vigorous conditions are employed than those generally described by Lee and Nolan. Also, see J. M. Dowie, et al., Chem. Ind. 900 (1966) for general methods to prepare the X=Cl compounds. To prepare a Formula IV compound wherein R is —CH$_2$X and the C-11 and C-15 and when appropriate the C-19 hydroxyl groups are ultimately deprotected it is preferable to utilize a Formula B-2 compound wherein hydroxy protecting groups can be removed by means other than acid hydrolysis. Typically use of tert-butyldimethylsilyl protecting groups and subsequent removal thereof by fluoride mediated hydrolysis using, e.g., tetra-n-butylammonium fluoride is an efficient method to be employed. Hydrolysis of the ester to the free C-1 position carboxylic acid is achieved by treatment with potassium hydroxide in methanol.

Reference is made to Chart D hereof to illustrate the preparation of compounds of Formula IV wherein R is formyl, i.e., —CHO, and D is —C≡C($\sim R_3$) wherein $R_3$ is hydrogen. A compound of Formula B-2 wherein $R'_{50}$ is —CH$_2$OH or the 5(E) or 5(Z) isomer thereof is esterified to a C-1 position carboxylic acid ester, e.g., the methyl ester, by standard procedures, for example, by using methyl iodide and an amine base, such as, diisopropyl ethyl amine in acetonitrile to give the methyl ester. The 9-hydroxymethyl-C-1 position carboxylic acid ester is then oxidized to the C-9 aldehyde of Formula D-1. Various standard oxidation procedures may be employed, e.g., a Collins oxidation using a chromium trioxide-pyridine complex in methylene chloride is a suitably useful method.

Ester hydrolysis using, e.g., potassium hydroxide, and if desired deprotection of the C-11 and C-15 and when appropriate the C-19 hydroxyl groups via fluoride mediated hydrolysis, gives the compounds of Formula D-2 wherein Q is COOH. The compounds of Formula D-1 may be converted to compounds of Formula D-2 wherein Q is other than COOH by the general procedures described hereinabove in reference to compounds of Formula B-3 by first protecting the C-9 aldehyde, e.g., as an ethylene ketal, then deprotection by acidic hydrolysis after the desired Q group is obtained and of course the C-1 position carboxylic acids of Formula D-2 can be converted to the various ester derivatives embraced by the present invention by generally known procedures.

The compounds of Formula D-2 wherein Q is —COOH are useful in preparing the compounds of Formula IV wherein R is —CH=C(X')$_2$ wherein X' is fluoro, chloro or bromo as illustrated in Chart E. When X' is fluoro the acid of Formula D-2(a) is subjected to a Wittig-type reaction using dibromodifluoromethane and triphenylphosphine as generally described by N. Ishikawa, et al., Chem. Lett. 983 (1979) to give compounds of Formula E-1. When X' is chloro the Formula D-2(a) compound is reacted with the anion of diethyldichloromethylphosphonate in a Wittig-type reaction according to the general procedures of J. Villieras, et al., Synthesis 458 (1975) and F. Karrenbrock, et al., Tetrahedron Lett. 2915 (1979) to give compounds of Formula E-1 wherein X' is chloro. When X' is bromo the Formula D-2(a) compound is reacted with carbontetrabromide-triphenylphosphine as generally described by E. J. Corey and P. L. Fuchs, Tetrahedron Lett. 3769 (1972) to give compounds of Formula E-2 wherein X' is bromo. The Formula E-1 compounds can be separated into the 5(Z) and 5(E) isomers and hydrolyzed to remove the C-11 and C-15 and if appropriate C-19 hydroxyl protecting groups. Also, the difluoroolefin compounds of Formula E-1 are useful in preparing compounds of Formula IV wherein R is —CH=CH$_2$F by hydride reduction of gem-difluoroolefin to monofluoroolefin by the general procedure of Ishikawa, et al., Chem. Lett. 983 (1979) to give compounds of Formula E-2. Of course, as indicated hereinabove, during such conversion from the difluoro to the monofluoroolefin any hydroxyl groups present in the compounds are protected. The compounds of Formulas E-1 and E-2 can be converted to the C-1 position ester, amide, amine, alcohol and nitrile derivatives of the present invention by procedures described hereinabove in reference to Formula B-3 compounds.

The compounds of Formula IV wherein D is —CH=C(~R$_3$) wherein R$_3$ is hydrogen and wherein Z is —(Ph)—(CH$_2$)$_q$— are prepared as follows reference being made to Chart F. The ketones of Formula A-2 are reduced by conventional means using, for example, a borohydride reducing agent such as sodium, potassium or lithium borohydride, to the corresponding alcohol. The alcohol is converted to a sulfonate derivative, typically a methanesulfonate or toluenesulfonate by treatment with methanesulfonyl chloride or toluenesulfonyl chloride in the presence of a tertiary amine such as triethylamine. The sulfonate derivative is treated with sodium, lithium or potassium thiophenoxide to give the compounds of Formula F-1. The thiophenoxide is preferably prepared by reacting equal molar amounts of thiophenol and a base such as potassium tertiary butoxide just prior to reaction with the sulfonate. The compounds of Formula F-1 are oxidized to the corresponding phenylsulfonate using, e.g., m-chloroperbenzoic acid then treated with a strong base such as n-butyllithium to generate the corresponding anion. The anion is treated with an aldehyde of Formula F-2 and the resulting adduct is treated with acetic anhydride to give compounds of Formula F-3. The compounds of Formula F-3 are treated with sodium amalgam by procedures analogous to those described by P. J. Kocienski, et al., "Scope and Stereochemistry of an Olefin Synthesis from β-Hydroxysulphones", JCS Perkin I, 829-834 (1978) to give the olefins of Formula F-4. The F-4 compounds wherein R$_{50}$ is —CH$_2$OH can be used to prepare the corresponding 9β—CH$_2$X substituted derivatives, referred to herein as Formula F-4(a) compounds, by the procedure of J. B. Lee and T. J. Nolan, Can. J. Chem. 44, 1331 (1966) as generally described hereinabove in reference to compounds of Formula A-3. The compounds of Formula F-4 and F-4(a) are used to prepare the products of Formula F-5. The various hydroxyl groups are protected in such a manner to permit selective hydrolysis to give ultimately the deprotected products of Formula F-5. When R$_{50}$ is —CH$_2$OH said group may be protected with, e.g., ethoxyethyl thus differentiating the primary alcohols. The R$_{21}$ silyl protecting group is conveniently removed via fluoride mediated hydrolysis using, e.g., tetrabutyl ammonium fluoride to give the C-1 position alcohol of Formula F-5 which is utilized to prepare the corresponding carboxylic acids, esters, amides, amines and nitriles of Formula F-5 by the same general procedures as described hereinabove in reference to the preparation of compounds of Formula C-5. The 5(E) and 5(Z) isomers can be separated conveniently using the alcohol corresponding to Formula F-4 and the various C-9, C-11, C-15 and C-19 hydroxyl protecting groups which may be present are removed by mild acid hydrolysis using, e.g., mixtures of water, tetrahydrofuran and acetic acid.

The compounds of Formula F-2 are prepared using known bis-acids of the formula

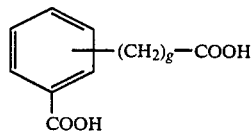

wherein g is zero, one, 2 or 3, which are reduced to the corresponding diol by conventional procedures, e.g., by using lithium aluminum hydride. About equal molar amounts of the diol and a silylating reagent of R$_{21}$ are combined thereby preferentially silylating the alkanol hydroxyl although some di-silylated compound is produced. The mono-silylated compounds of the formula

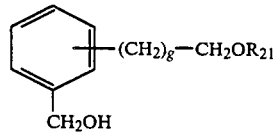

are oxidized to the aldehydes of Formula F-2 by conventional means, e.g., using manganese dioxide. See U.S. Pat. No. 4,306,075.

When the compounds of Formula F-5 wherein R$_{51}$ is —CH$_2$OH, Q is a carboxylic acid ester such as the methyl ester, and the various C-11, C-15 and C-19 hydroxyl groups which may be present are protected, is substituted for compounds of Formula B-2(a) and treated by procedures analogous to those described in connection with the formation of compounds of Formula D-2 from Formula B-2(a) compounds, one obtains compounds of Formula F-6 depicted in Chart F.

When the compounds of Formula F-6 wherein Q is —COOH are substituted for the compounds of Formula D-2(a) in Chart E and the general procedures described in reference to Chart E are followed including the conversion of the C-1 position carboxyl group to the various other C-position groups represented by Q, compounds of Formulas F-7 and F-8 set forth in Chart F are obtained.

The compounds of Formulas D-2 and F-6 wherein Q is —CH$_2$OH can be used to prepare the compounds of Formulas D-3 and F-9, respectively, depicted in Charts D and F, by initially protecting any free hydroxyl groups, and typically the primary alcohol is protected with an R$_{21}$ silyl group defined herein, then treating the protected alcohol with LiCBr$_2$H followed by treatment with zinc in acetic acid according to the general procedure of D. R. Williams, et al., Tetrahedron Lett. 3745 (1981). Hydrolysis to remove the hydroxyl protecting groups gives compounds of Formulas D-3 and F-9 wherein Q is —CH$_2$OH. The thus obtained alcohol can be oxidized to the corresponding C-1 position carboxylic acid by standard oxidation procedures, e.g., using Jones reagent or via Collins oxidation and the acid can be utilized in the preparation of the esters, amides, amines, and nitriles of Formulas D-3 and F-9 by means analogous to that described for the preparation of Formula B-3 compounds herein.

The compounds of Formula IV wherein D is —CH=C(~R$_3$) and R$_3$ is fluoro are prepared by reacting compounds of Formula A-2 and A-3 from Chart A hereof with a sulfoxime of the formula G-1 as depicted in Chart G by the general procedures described in U.S. Pat. No. 4,238,414 at column 30, lines 36 to 62. The compounds of Formula G-2 are then selectively hydrolyzed to the primary alcohol using, e.g., tetra-n-butylammonium fluoride. The alcohols thus obtained can be oxidized to the corresponding C-1 position carboxylic acids, esters, amides, amines and nitriles of Formula G-3 by the same general procedures described hereinabove in reference to the preparation of compounds of Formula C-5 in Chart C. The 5(E) and 5(Z) isomers can be separated conveniently using the primary alcohol corresponding to Formula G-2, and the C-11 and C-15 hydroxyl protecting groups as well as the C-19 hydroxyl protecting group when R$_{17}$ is protected —(CH$_2$)$_2$—CH(OH)CH$_3$ are removed by mild acid hydrolysis.

The sulfoxime of Formula G-1 are prepared by treating a compound of the formula

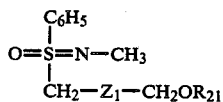

wherein Z$_1$ and R$_{21}$ have the meanings defined hereinabove, which compounds are known in the art (See U.S. Pat. No. 4,238,414) or are prepared by procedures generally known in the art with a strong base such as n-butyllithium in hexane to generate the anion which is treated with a fluorine source a preferred fluorine source being perchloryl fluoride, i.e., FClO$_3$.

When the compounds of Formula G-3 wherein R$_{51}$ is —CH$_2$OH and Q is COOH are substituted for compounds of Formula B-2(a) in Chart D and treated by procedures analogous to those described in connection with the formation of compounds of Formula D-1 and D-2 from Formula B-2(a) compounds, one obtains compounds of Formula G-4 depicted in Chart G.

When the compounds of Formula G-4 are substituted for the compounds of Formula D-2(a) in Chart E and the general procedures described in reference to Chart E are followed compounds of Formula G-5 and G-6 depicted in Chart G are obtained.

The compounds of Formula G-4 wherein Q is —CH$_2$OH can be used to prepare the compounds of Formula G-7 in a manner analogous to that described aaaaaahereinabove in connection with the preparation of compounds of Formulas D-3 and F-9.

The aldehydes of Formulas D-1 and D-2(a) (depicted in Charts D and E, respectively) and of Formulas F-6 and G-4 can also be used to prepare the corresponding 9$\beta$-vinyl substituted compounds of Formula IV by treating the aldehyde with methylene triphenylphosphorane under the conditions of a Wittig-type reaction by procedures well known in the art. It is preferred that separation of the 5(E) and 5(Z) isomers be carried out using the C-1 position carboxylic acid ester and as indicated hereinbefore compounds wherein the C-11 and C-15 hydroxyl groups are protected. Hydrolysis to the free acid and free hydroxyl compounds is achieved as described hereinabove.

The compounds of Formula B-2 wherein R'$_{50}$ is —C≡CH, and of Formulas F-5 and G-3 wherein Q is —COOH and R$_{51}$ is —C≡CH can be used to prepare the corresponding compounds wherein R$_{50}$ or R$_{51}$ is —CH=CH$_2$ by selective reduction of the ethynyl compound by procedures known in the art.

The compounds of Formula B-2 wherein R'$_{50}$ is —C≡CC$_n$H$_{2n}$CH$_3$ and of Formulas F-5 and G-3 wherein Q is —COOH or —CH$_2$OH and R$_{51}$ is —C≡CC$_n$H$_{2n}$CH$_3$ may also be prepared from the corresponding compounds wherein R'$_{50}$ or R$_{51}$ is —C≡CH by treatment of the ethynyl compound with excess base, e.g., lithium diisopropylamide, followed by quenching with an alkylating agent of the formula —A—C$_n$H$_{2n}$—CH$_3$ wherein n is zero, one, 2 or 3 and A is a leaving group such as bromide or iodide or a mesylate or tosylate leaving group. This general procedure is well known in the art.

The compounds of Formula B-2 wherein R'$_{50}$ is cis-CH=CHC$_n$H$_{2n}$CH$_3$ and of Formulas F-5 and G-3 and wherein Q is —COOH and R$_{51}$ is cis-CH=CHC$_n$H$_{2n}$CH$_3$ can also be prepared from the corresponding compound wherein R'$_{50}$ or R$_{51}$ is —C≡CC$_n$H$_{2n}$CH$_3$ by controlled hydrogenation of the alkynyl compound using, e.g., a Lindlar catalyst or quinoline or by a dissolving metal reduction of the alkynyl compound by art known procedures.

The compounds of Formula IV wherein R is CH=CHCl are prepared utilizing an enone of the following formula PX which compounds are all known in the art or are prepared by well known procedures.

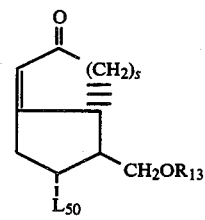

Formula PX

In Formula PX, L$_{50}$ has the same meaning as L only R$_{12}$ is other than hydrogen; s is the integer one or 2; and R$_{13}$ is a protecting group as defined hereinabove. Additionally, the compounds of Formula PX can be used to prepare the compounds of Formula IV wherein R is —CN; —CH$_2$OH; —C≡CH; —C≡CC$_n$H$_{2n}$CH$_3$; —C≡C—C≡CR$_1$; —C≡C—OR$_2$; —C≡CCF$_3$; —CH=CH$_2$; cis-CH=CHC$_n$H$_{2n}$CH$_3$; or trans-CH=CHC$_n$H$_{2n}$CH$_3$.

In referring to Chart A when the compounds of Formula PX are substituted for and reacted in the manner analogous to that described for compounds of Formula A-1 one obtains compounds of the following Formula PX(a) wherein R$_{50}$ has the meaning defined in Formula A-2, and s, $R_{13}$ and $L_{50}$ have the meanings defined in Formula PX.

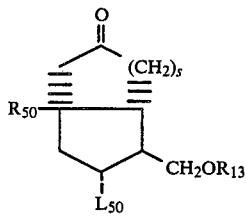

Formula PX(a)

When the compounds of Formula PX(a) wherein $R_{50}$ is —$CH_2OH$ are substituted for and treated in a manner analogous to that described for Formula A-2 compounds wherein $R_{50}$ is —$CH_2OH$ in preparing the Formula A-3 compounds, the compounds of Formula PX(b) are obtained wherein X is chloro or bromo

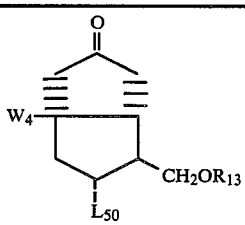

Formulas PX(b)–PX(e)

| W4 | Formula |
|---|---|
| —$CH_2X$ | PX(b) |
| —C≡$CSi(CH_3)_3$ | PX(c) |
| trans-CH=CHX' | PX(d) |
| cis-CH=CHX' | PX(e) |

In preparing compounds of Formula PX(a) wherein $R_{50}$ is —C≡CH an intermediate product of the Formula PX(c) above is obtained. This trimethylsilylacetylene intermediate is used to prepare intermediates which are useful in preparing the compounds of Formula IV wherein R is cis-CH=CHX' or trans-CH=CHX' wherein X' is chloro or bromo. The PX(c) compound is reduced to trans-vinylsilane, e.g., by hydrosilylation by the general procedure described by R. B. Miller and G. McGarvey, J. Org. Chem. 43, 4424 (1978) then halogenated with bromine or chlorine with subsequent elimination of trimethylsilyl halide by the procedure of Miller and McGarvey, ibid., to give the trans-halovinyl intermediate of Formula PX(d) wherein X' is bromo or chloro.

Similarly following the general procedure of Miller and McGarvey, ibid., the Formula PX(c) compounds are reduced to cis-vinylsilane by hydralumination-protonolysis followed by halogenation and subsequent elimination of trimethylsilylhalide to give the cis-halovinyl intermediate of Formula PX(e) wherein X' is chloro or bromo.

Also, hydroboration of the compounds of Formula PX(a) wherein $R_{50}$ is —C≡CH using catecholborane followed by treatment with an appropriate halogen, i.e., chlorine or bromine at 0° C. then treatment with a base such as sodium methoxide at 0° C. according to the general procedure of H. C. Brown, et al., J. Am. Chem. Soc. 95, 6456 (1973) one obtains the compounds of Formula PX(e) wherein X' is chloro or bromo.

When the compounds of Formulas PX(a) wherein $R_{50}$ is other than CN, PX(b), PX(d) and PX(e) are substituted for and treated in a manner analogous to that described for the compounds of Formulas A-2 and A-3 as set forth in Chart B compounds of the following formula PX(f) are obtained:

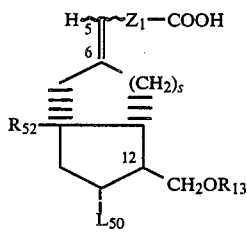

Formula PX(f)

wherein s, $R_{13}$, $Z_1$ and $L_{50}$ have the meanings defined hereinbefore and $R_{52}$ is —C≡CH; —C≡$CC_nH_{2n}CH_3$; —C≡C—C≡$CR_1$; —C≡C—$OR_2$; —C≡$CCF_3$; —CH=$CH_2$; cis-CH=$CHC_nH_{2n}CH_3$; trans-CH=$CHC_nH_{2n}CH_3$; —$CH_2X$, —$CH_2OH$, cis-CH=CHX', or trans-CH=CHX' wherein X' is chloro, bromo or fluoro. The compounds of Formula PX(f) can be converted to compounds of Formula PX(g) when treated in manners analogous to those described for the compounds of Formula B-2 in Chart B.

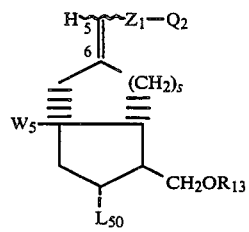

Formulas PX(g)–PX(k)

In Formulas PX(g)–PX(k) s, $R_{13}$, $L_{50}$, and $Z_1$ have the meanings defined hereinbefore and $Q_2$ and $W_5$ have the meanings defined below:

| $W_5$ | $Q_2$ | Formula |
|---|---|---|
| Same as $R_{52}$ | Same as Q' | PX(g) |
| —CN | Same as Q | PX(h) |
| —CHO | Same as Q | PX(i) |
| —CH=C(X')$_2$ | Same as Q | PX(j) |
| —CH=C(H)(F) | Same as Q | PX(k) |

When compounds of Formula PX(a) wherein $R_{50}$ is —CN are substituted for compounds of Formula A-2 and the general procedures set forth in Chart C are followed the compounds of the above Formula PX(h) are obtained.

When the compounds of Formula PX(f) wherein $R_{52}$ is —$CH_2OH$ are substituted for the compounds of Formula B-2(a) and the general procedures set forth in Chart D are followed compounds of the above Formula PX(i) are obtained.

The compounds of Formula PX(i) wherein $Q^2$ is COOH can be substituted for the compounds of Formula D-2(a) in Chart E and when the general procedures set forth in Chart E are followed including the subsequent conversion of the C-1 position carboxyl group to the other C-1 position groups represented by Q, the compounds of the above Formulas PX(j) and PX(k) are obtained.

When the compounds of Formulas PX(a), PX(d) and PX(e) are substituted for the compounds of Formulas A-2 in Chart F and the general procedures described with respect to Chart F are followed or when the compounds of Formulas PX(a), PX(b), PX(d) and PX(e) are substituted for the compounds of Formulas A-2 and A-3 in Chart G and the general procedures described in Chart G are followed intermediates of the following respective Formulas PX(l) and PX(m) are obtained wherein $R_{53}$ is —CN or $R_{52}$ only $R_{53}$ is not —CH$_2$X, and $R_{52}$, g, Q, s, $R_{13}$ and $L_{50}$ have the meanings defined hereinbefore.

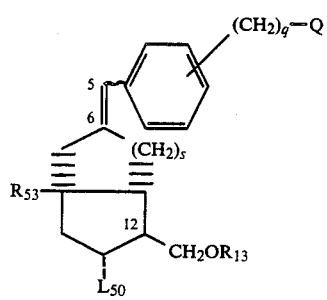

Formula PX(l)

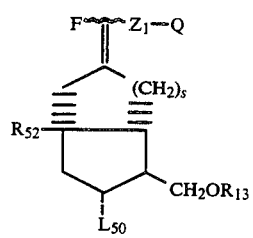

Formula PX(m)

When the compounds of Formulas PX(l) or PX(m) wherein $R_{53}$ is —CH$_2$OH and Q is COOH are substituted for the compounds of Formula B-2(a) and the general procedures set forth in Chart D are followed compounds of the following respective formulas PX(n) and PX(o) are obtained:

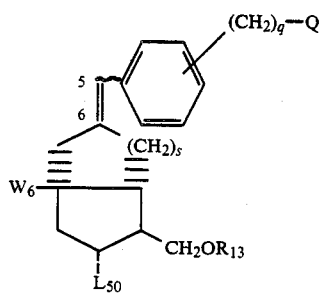

Formula PX(n) and (p)

| $W_6$ | Formula |
|---|---|
| —CHO | PX(n) |
| (X)$_2$C=CH— | PX(p) |

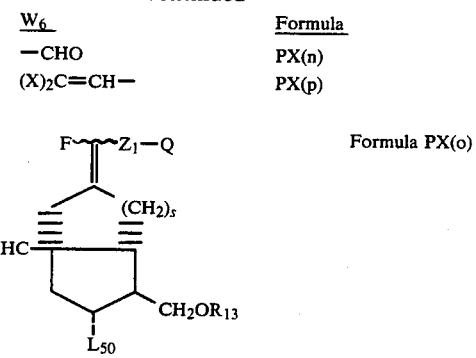

Formula PX(o)

When the compounds of Formulas PX(n) or PX(o) wherein Q is —COOH are substituted for the compounds of Formula D-2(a) and the general procedures described with respect to Chart E are followed including the subsequent conversion of the C-1 position carboxyl group to the other C-1 position groups represented by Q, the respective intermediates of Formulas PX(p) (see above) and PX(q) are obtained:

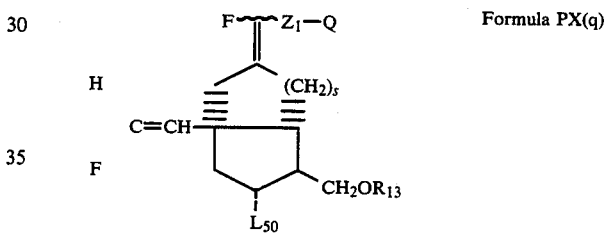

Formula PX(q)

The compounds of Formula PX(l) wherein $R_{53}$ is —CH$_2$OH can also be used to prepare the corresponding compounds subsituted at the 9-position with —CH$_2$X by the general procedures of J. B. Lee and T. J. Nolan, Can. J. Chem. 44, 1331 (1966) described hereinabove, which compounds are referred to herein as Formula PX(r).

The intermediates of Formulas PX(f)–PX(r) are utilized in preparing the CBA$_2$ compounds of Formula IV by procedures which are also useful in preparing compounds of Formula A-1 (Chart A). Initially the intermediates of Formulas PX(f) to PX(r) are hydrolyzed to remove the $R_{13}$ protecting group thus giving the primary alcohol derivatives which are oxidized to the corresponding aldehyde by conventional procedures, e.g., under the conditions of a Collins reaction. To prepare compounds of Formula A-1 one utilizes aldehydes of the following general Formula MX which are obtained by oxidation of the corresponding C-12 position substituted alcohol by conventional procedures. The alcohols are known in the art or are readily prepared by procedures known in the art.

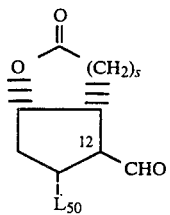

Formula MX

In the above Formula MX s is the integer one or 2 and $L_{50}$ has the meaning defined in Formula PX above.

The "C-12 aldehydes" corresponding to the intermediates of Formulas PX(f) to PX(r) and the aldehydes of Formula MX are then treated as described hereinbelow, wherein for purposes of convenience only the chemical transformations which occur at the "C-12 position" of said compounds are depicted.

The "C-12" aldehydes are subject to a Wittig reaction with an alkyl phosphonate derivative of the formula

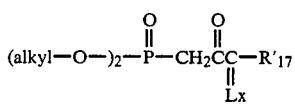

which is obtained by addition of the anion of dialkylmethylphosphonate, i.e.,

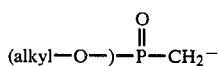

with an ester of the formula

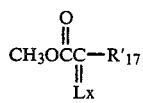

by procedures known in the art. $R'_{17}$ and Lx have the same meanings as $R_{17}$ and $L_1$ except

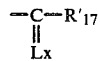

is other than $-C\equiv CC_qH_{2q}CH_3$ or $-C_pH_{2p}CH=CH_2$. There results compounds wherein the "C-12 position" is substituted with

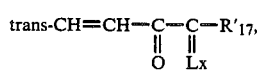

the ketone of which is reduced to the various M groups defined hereinabove to give the corresponding compounds wherein the "C-12 position" is substituted with

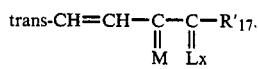

These trans-vinyl derivatives can be hydrogenated to give the corresponding compounds wherein the "C-12 position" is substituted with

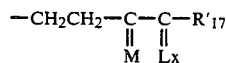

or can be halogenated followed by tetradehydrohalogenation to give the corresponding compounds wheren the "C-12 position" is substituted with

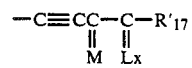

which upon hydrogenation with a Lindlar catalyst gives the cis-vinyl derivatives, i.e., compounds wherein the "C-12 position" is substituted with

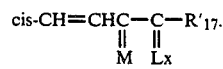

Compounds corresponding to those of Formulas MX or PX(f) to PX(r) wherein the "C-12 position" is substituted with

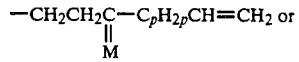

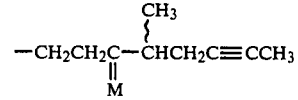

can also be prepared by treating the appropriate "C-12" aldehyde compound with an alkylphosphonate depicted above only wherein

is $-C_pH_{2p}CH=CH_2$ or

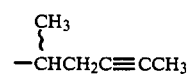

to give the corresponding compounds wherein the "C-12 position" is substituted with

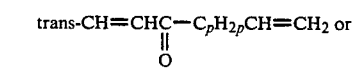

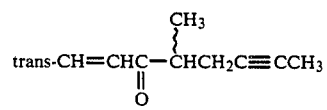

the trans-vinyl group of which is reduced, e.g., by dissolving metal reduction followed by reduction of the ketone to the various M groups defined hereinabove.

Additionally, treatment of the "C-12" aldehydes with a phosphine of the formula(alkyl)$_3$P=CHCHO under the conditions of a Wittig reaction gives the corresponding compounds wherein the "C-12 position is substituted with trans-CH=CHCHO which can be reduced to give the corresponding compound wherein the "C-12 position" is substituted with —CH$_2$CH$_2$CHO. Also the compounds corresponding to the Formula MX or Formulas PX(f) to PX(r) only wherein the "C-12 position" is substituted with trans-CH=CHCHO can be reduced to the corresponding alcohol, i.e, trans-CH=CHCH$_2$OH then hydrogenated to give compounds wherein the "C-12 position" is substituted with —CH$_2$CH$_2$CH$_2$OH. Or, the trans-vinyl alcohol can be halogenated then tetradehydrohalogenated to give the corresponding ethynyl, i.e., compounds wherein the "C-12 position" is substituted with —C≡CCH$_2$OH, which upon hydrogenation with a Lindlar catalyst gives the cis-vinyl alcohol compounds. The thus obtained alcohols, i.e., the compounds corresponding to those of Formulas MX or PX(f) to PX(r) only wherein the "C-12 position" is substituted with trans-CH=CHCH$_2$OH, —CH$_2$CH$_2$CH$_2$OH, —C≡CCH$_2$OH or cis-CH=CHCH$_2$OH can then be oxidized to the aldehyde to give the corresponding compounds wherein the terminal primary alcohol contained in the "C-12" substituent is replaced by —CHO. The aldehydes are then treated with a Grignard reagent of the formula haloMgC$_p$H$_{2p}$CH=CH$_2$ or an alkyllithium of the formula LiC$_p$H$_{2p}$CH=CH$_2$, or an acetylide anion of the formula —C≡CC$_p$H$_{2p}$CH$_3$ to give compounds corresponding to those of Formulas MX or PX(f) to PX(r) only wherein the "C-12 position" is substituted with

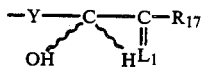

wherein Y, L$_1$ and R$_{17}$ have the meanings defined hereinabove. These thus obtained alcohol derivatives can be oxidized to the ketone and treated with methyl lithium or a methyl Grignard to give the corresponding compounds wherein the "C-12 position" is substituted with

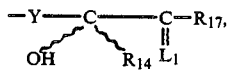

wherein R$_{14}$ is methyl.

Upon completion of the above-described "C-12 position" transformations with respect to the compounds of Formula MX the resulting lactone derivatives are converted to the compounds of Formula A-1 via lactol and diketone phosphonate derivatives in a manner analogous to that described in U.S. Pat. No. 4,306,075 in reference to Chart A thereof.

The CBA$_1$ compounds of Formula IV, i.e., compounds of Formula IV wherein D is —CH$_2$CH$_2$— and wherein R is other than —C≡CH and —C≡C—C$_n$H$_{2n}$—CH$_3$ are prepared by reducing the compounds of Formulas PX(f) to PX(l) and of Formulas PX(n), PX(p) and PX(r) to the corresponding derivatives wherein the carbon atoms at positions C-5 and C-6 are saturated. This reduction is carried out by procedures generally known in the art, such as the general methods described in British Published Application No. 2,017,699. For example, the reduction may be achieved by a standard hydrogenation in the presence of a catalyst such as palladium on charcoal or platinum dioxide in a lower alcohol such as ethanol or methanol. The resulting 5,6-dihydro intermediates are then utilized to prepare the CBA$_1$ compounds of Formula IV by the same general procedures described hereinabove in connection with the conversion of compounds of Formulas PX(f)–PX(r) to CBA$_2$ compounds of Formula IV.

The CBA$_1$ compounds of Formula IV wherein R is —C≡CH and —C≡C—C$_n$H$_{2n}$—CH$_3$ are prepared from the compound of Formula IV wherein D is —C=C(~R$_3$)— and R$_3$ is hydrogen and wherein R is —CH=CH$_2$ or —CH=CH—C$_n$H$_{2n}$—CH$_3$ by treating one equivalent of the 9β-vinyl compound with one equivalent bromine followed by treatment with a strong base as generally described in U.S. Pat. No. 4,147,873.

A preferred method of preparing the CBA$_1$ compounds of Formula IV wherein R is other than —C≡CH and Z is trans-CH$_2$CH=CH— is to utilize the appropriate intermediates of Formulas PX(g) to PX(k) wherein R$_{52}$ is other than —C≡CH, Z is —CH$_2$—(CH$_2$)$_f$—C(R$_4$)$_2$— wherein f is one and R$_4$ is hydrogen and wherein Q is a carboxylic acid ester, preferably the methyl ester which derivatives are referred to herein as the butanoic acid esters. The butanoic acid ester derivatives are treated with lithium amide base and phenylselenyl chloride to give the corresponding α-phenylselenyl derivatives which are reduced by, e.g., general procedures described in U.K. Application No. GB2,017,699 to give the 5,6-dihydro intermediates. The 5,6-dihydro intermediates are dehydrophenylselenized by treatment with hydrogen peroxide to give intermediates corresponding to Formulas PX(g) to PX(k) wherein Z$_1$ is —CH$_2$CH=CH$_2$, Q$^2$ is a carboxylic acid ester and the carbon atoms at positions 5 and 6 are saturated, which intermediates can be converted to the corresponding derivatives wherein the terminal C-1 position corresponds to Q as defined herein by the general procedures described hereinabove in connection with the preparation of compounds of Formula B-3 in Chart B. These 5,6-dihydro intermediates are then converted to the CBA$_1$ compounds of Formula IV wherein Z is —CH$_2$CH=CH— by treatment in a manner analogous to that described hereinabove in connection with the conversion of Formulas PX(f)–PX(r) to CBA$_2$ compounds of Formula IV.

When the alkyl ester has been obtained and an acid is desired, saponification procedures, as known in the art for PGF-type compounds are employed.

When an acid has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acd reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for alkyl, cycloalkyl or aralkyl esterification of the carboxy moiety of the acid compounds comprises transformation of the free acid to the corresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., Q is —COOR$_5$ and R$_5$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift No. 2,535,693, and Derwent Farmdoc No. 16828X.

The phthalidyl esters are obtained by treating the corresponding acid with a phthalidyl halide such as the bromide in, e.g., dimethylformamide in the presence of an amine base. The phosphoranyl esters are obtained by treating the corresponding acid with a 1-halo derivative, e.g., the 1-chloro derivative of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is —COL$_2$) are prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741 describing the preparation of carbonylamido and sulfonylamido derivatives of prostaglandin-type free acids.

The preferred method by which the present amido and cycloamido derivatives of the acids are prepared is, first, by transformation of such free acids to corresponding mixed acid anhydrides. By this procedure, the carbacyclin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at −10° C. to 20° C.

Thereafter, the mixed anhydride is converted to the corresponding amido or cycloamido derivatives by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about −10° to +10° C., until the reaction is shown to be complete.

Thereafter, the novel amido or cycloamido derivative is recovered from the reaction mixture by conventional techniques.

The carbonylamido and sulfonylamido derivative of the presently disclosed carbacyclin compounds are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure carbacyclin sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about 0° C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation if inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(3′S)-1β-Cyano-7α-tetrahydropyran-2-yloxy-6β[3′-tetrahydropyran-2-yloxy-trans-1′-octenyl]-bicyclo-[3.3.0]-octan-3-one A solution of 1.43 g (3.31 mmol) of (3′S)-7α-tetrahydropyran-2-yloxy-6β[3′-tetrahydropyran-2-yloxy-trans-1′-octenyl]-bicyclo-[3.3.0]-octen-3-one, 0.51 g (3.9 mmol) of 18-crown-6, 0.43 g (6.6 mmol) of potassium cyanide, and 0.36 ml (3.94 mmol) of acetone cyanohydrin in 20 ml of toluene is stirred at ambient temperature under argon for 18 hr, then added to 100 ml of water, and extracted with three 200 ml portions of ether. The combined ether extracts are washed with brine and dried over anhydrous magnesium sulfate. The solvents are removed under reduced pressure, and the residue chromatographed on silica gel eluting with 2:1 hexane-ethyl acetate to give 0.86 g (57%) of the title compound as a pale yellow oil ($R_f$ 0.31 in 2:1 hexane-ethyl acetate).

NMR (CDCl$_3$; TMS): δ0.89 (t, J=5 Hz, 3H), 1.08—3.24 (m, 28H), 3.24–4.47 (m, 6H), 4.67 (bs, 2H), 5.3–5.9 (m, 2H).

Infrared: νmax (film): 2230, 1750, 1665, 1200, 1155, 1125, 1075, 1035, 1020, 975, 905, 870, 815 cm$^{-1}$.

EXAMPLE 2

5-Carboxypentanol, t-butyldimethylsilyl ether

A solution of 4 g (100 mmol) of sodium hydroxide in 100 ml of methanol and water (4:1) is treated with 10 ml (90 mmol) of ε-caprolactone and stirred at ambient temperature under a nitrogen atmosphere. After 20 hr, the solvent is evaporated using a toluene azeotrope, yielding 15 g of solid, crude 5-carboxypentanol, sodium salt.

The above solid is suspended in 300 ml of dimethylformamide under a nitrogen atmosphere, cooled to 0° C., treated with 35 g (510 mmol) of imidazole, stirred for 15 min at 0° C. and 15 min at ambient temperature, coold to 0° C. and treated with 39 g (260 mmol) of t-butyldimethylsilylchloride. The resulting solution is then allowed to warm to ambient temperature under a nitrogen atmosphere. After 26 hr, the resulting solution is treated with 8 g of sodium hydroxide in 40 ml of water and 40 ml of methanol, with stirring maintained under a nitrogen atmosphere. After 13 hr the suspension is acidified to pH 4 with 500 ml of 1N aqueous hydrogen chloride, then saturated with sodium chloride and extracted with four 300 ml portions of ethyl acetate. The combined ethyl acetate extracts are then washed with four 250 ml portions of 1N aqueous sodium hydroxide. The combined basic extracts are then acidified to pH 4 l with concentrated hydrochloric acid, saturated with brine, and extracted with four 300 ml portions of ethyl acetate. The combined extracts are then washed with brine, dried over sodium sulfate, and concentrated under reduced pressure to yield 22.6 g of a yellow liquid, 5-carboxypentanol, t-butyldimethylsilyl ether. Chromatography on 800 g of silica gel eluting with ethyl acetate and hexane (1:9) to 1:1) yields 14.8 g (67%) of 5-carboxypentanol, t-butyldimethylsilyl ether, which can be distilled (152° at 0.02 torr) to give a 99% yield of acid as a colorless oil (solidifies in the freezer).

NMR (CDCl$_3$, TMS): δ0.05 (s, 6H), 0.90 (s, 9H), 1.2–2.0 (m, 6H), 2.17–2.55 (m, 2H), 3.42–3.83 (s, 2H), 11.72 (s, 1H).

Infrared: νmax (film): 3040, 2740, 2660, 1715, 1255, 1100, 835, 775 cm$^{-1}$.

EXAMPLE 3

2-Decarboxy-2-(t-butyldimethylsilyloxy)methyl-9β-cyano-6a-carba-prostaglandin I$_2$, 11,15-Bis(tetrahydropyranyl ether)

A solution of 1.20 ml (8.56 mmol) of diisopropylamine in 40 ml of dry tetrahydrofuran (THF) at 0° under argon is treated dropwise with 5.2 ml (8.32 mmol) 1.6M n-butyllithium in hexane, then stirred at 0° for 5 min, treated with 1.03 g (4.18 mmol) of 5-carboxypentanol, t-butyldimethylsilyl ether in 10 ml of THF (tetrahydrofuran), stirred at 0° for 15 min and room temperature for one hr, cooled to 0° and treated with 1.7 g (3.7 mmol) of (3'S)-1β-cyano-7α-tetrahydropyran-2-yloxy-6β[3'-tetrahydropyran-2-yloxy-trans-1'-octenyl]-bicyclo-[3.3.0]octan-3-one in 10 ml of THF, and allowed to warm to ambient temperature. After 20 hr the solution is added to a solution of 10 ml of 1N aqueous hydrochloric acid in 300 ml of cold brine, and extracted with three 300 ml portions of ether. The combined ether extracts are washed with a solution of 4 ml of 1N aqueous HCl in 300 ml brine, and with 300 ml brine, and dried briefly over anhydrous magnesium sulfate. The solvents are removed in vacuo to give 2.5 g of a yellow oil.

A degassed solution of 2.46 g of the above crude β-hydroxy acid in 30 ml of methylene chloride is treated with 5.0 ml (18 mmol) dimethylformamide dineopentyl acetal, stirred under nitrogen at ambient temperature for 117 hr, added to 500 ml of 4:1 ice water-brine and extracted with 500 ml of ether and then with two 250 ml portions of ether. The combined ether extracts are washed with 500 ml bicarb and 400 ml brine and dried over anhydrous magnesium sulfate. The solvents are removed under reduced pressure to give 3 g of an orange oil which is chromatographed on silica gel eluting with 20% ethyl acetate in hexane to give 0.93 g (39%) of the title compounds as a very pale yellow oil.

NMR: (CDCl$_3$, TMS): δ0.05 (s, 6H), 0.91 (s, 12H), 1.08–2.9 (m, 34H), 3.25–4.40 (m, 8H), 4.68 (bs, 2H), 5.02–5.8 (m, 3H).

Infrared: νmax (film): 2230, 1670, 1255, 1200, 1125, 1100, 1080, 1035, 1020, 975, 835, 775 cm$^{-1}$.

EXAMPLE 4

(5Z)-2-Decarboxy-2-hydroxymethyl-9β-cyano-6a-carba-prostaglandin I$_2$, 11,15-bis(tetrahydropyranyl ether) and (5E)-2-Decarboxy-2-hydroxymethyl-9β-cyano-6a-carba-prostaglandin I$_2$, 11,15-bis(tetrahydropyranyl ether)

A degassed solution of 1.1 g (1.7 mmol) of 2-decarboxy-2-(t-butyldimethylsilyloxy)methyl-9β-cyano-6a-carba-PGI$_2$, 11,15-bis(tetrahydropryanyl ether) in 20 ml of THF at 0° under nitrogen is treated with 4.8 ml (3.6 mmol) of tetra-n-butylamminoium fluoride, stirred for 18 hr at ambient temperature, added to 150 ml of brine, and extracted with two 150 ml portions of ethyl acetate. The combined ethyl acetate extracts are washed with 100 ml of 0.5M aqueous potassium bisulfate, 100 ml bicarb, and 100 ml brine, and are dried over anhydrous sodium sulfate. The solvents are removed under reduced pressure to give 1.26 g of a yellow oil which is filtered through 30 g silica gel eluting with 300 ml of 2:1 ethyl acetate-hexane to give 1.2 g of yellow oil. Chromatography on silica gel eluting with 45% ethyl acetate in hexane yielded 0.52 g (57%) of the (5E) title compound isomer and 0.32 g (35%) of the (5Z) title compound isomer, both as colorless oils.

For the (5Z) isomer: R$_f$ 0.25 in 45% ethylacetate in hexane.

NMR (CDCl$_3$, TMS): δ0.89 (t,J=5 Hz, 3H), 1.05–3.0 (m, 35H), 3.2–4.4 (m, 8H), 4.69 (bs, 2H), 5.1–5.9 (m, 3H).

Infrared: νmax (film): 3480, 2240, 1670, 1200, 1130, 1075, 1035, 1020, 975, 905, 870 cm$^{-1}$.

For the (5E) isomer: R$_f$ 0.29 in 45% ethylacetate in hexane.

NMR (CDCl$_3$, TMS): δ0.89 (t,J=5 Hz, 3H), 1.07–3.2 (m, 35H), 3.2–4.4 (m, 8H), 4.67 (bs, 2H), 5.0–5.8 (m, 3H).

Infrared: νmax (film): 3480, 2240, 1670, 1200, 1130, 1075, 1035, 1020, 975, 905, 870 cm$^{-1}$.

EXAMPLE 5

(5Z)-9β-Cyano-6a-carba-prostaglandin I$_2$, methyl ester

A solution of 307 mg (0.58 mmol) of (5Z)-2-decarboxy-2-hydroxymethyl-9β-cyano-6a-carba-prostaglandin I$_2$, 11,15-bis(tetrahydropyranyl ether) in 11 ml of acetone at −20° under argon is treated with 0.55 ml of Jones reagent over 5 min and the resulting brown solution stirred at −20° for 2 hr, quenched with 0.6 ml of 2-propanol, stirred for 35 min at −20°, added to 80 ml of brine, and extracted with two 80 ml portions of ethyl acetate. The combined ethyl acetate extracts are washed with three 80 ml portions of brine and dried over anhydrous sodium sulfate. The solvents are removed in vacuo to give 0.3 g of an oil which is dissolved in 4 ml of acetonitrile, cooled to 15° under nitrogen, treated with 1.2 ml of diisopropylethyl amine and 0.43 ml of methyl iodide, stirred for 18 hr while warming to room temperature, treated with 0.09 ml of methyl iodide, stirred at room temperature for 3 hr, added to 50 ml of brine, and extracted with two 50 ml portions of ethyl acetate. The combined ethyl acetate extracts are washed with 50 ml of 0.5M aqueous potassium bisulfate, 50 ml of bicarb, and 50 ml of brine, and dried over anhydrous sodium sulfate.

The solvents are removed in vacuo to give 0.3 g of an oil which is dissolved in 14 ml of 1:2:4 THF-water-acetic acid, stirred for 3 hr at 45° under nitrogen, cooled, added to 75 ml of brine and extracted with two 75 ml portions of ethyl acetate. The combined ethyl acetate extracts are washed with three 75 ml portions of bicarb and two 150 ml portions of brine, and are dried over anhydrous sodium sulfate. The solvents are removed in vacuo to give 0.28 g of an oil which is chromatographed on silica gel eluting with 20% ethyl acetate in hexane to give 0.17 g (75%) of the title compound as a colorless oil (R$_f$ 0.25 in 20% hexane in ethyl acetate).

NMR: (CDCl$_3$, TMS): δ0.90 (t,J=5 Hz, 3H), 1.05–3.0 (m, 22H), 3.2–3.5 (m including 3H singlet at 3.68δ, 7H), 5.15–5.85 (m, 3H).

Infrared: νmax (film): 3400, 2230, 1740, 1675, 1435, 1315, 1250, 1230, 1200, 1170, 1135, 1100, 1075, 1020, 970 cm$^{-1}$.

EXAMPLE 6

(5E)-9β-Cyano-6a-carba-prostaglandin I₂, methyl ester

A solution of 0.50 g (0.94 mmol) of (5E)-2-decarboxy-2-hydroxymethyl-9β-cyano-6a-carba-prostaglandin I₂, 11,15-bis(tetrahydropyranyl ether) in 18 ml of acetone at −20° under nitrogen is treated over 5 min with 0.90 ml of Jones reagent, stirred at −20° for 2 hr, quenched with 1.0 ml of 2-propanol, stirred at −20° for 25 min, added to 150 ml of brine, and extracted with two 150 ml portions of ethyl acetate. The combined ethyl acetate extracts are washed with three 150 ml portions of brine and dried over anhydrous sodium sulfate. The solvents are removed in vacuo to give 0.5 g of an oil which is dissolved in 6 m of acetonitrile, treated with 1.9 ml (10.9 mmol) of diisopropylethyl amine, cooled to 15°, treated with 0.70 ml (11.2 mmol) of methyl iodide, and allowed to slowly warm to room temperature. After 16 hr the resulting suspension is reated with another 0.15 ml (2.4 mmol) of methyl iodide, stirred for 2 hr, added to 50 ml of brine, and extracted with two 50 ml portions of ethyl acetate. The combined ethyl acetate extracts are washed with 50 ml of 0.5M aqueous potassium bisulfate, 50 ml bicarb, and 50 ml brine, and dried over anhydrous sodium sulfate.

The solvents are removed in vacuo to give 0.5 g of yellow oil which is dissolved in 28 ml of 1:2:4 of THF-water-acetic acid and heated for 2½ hr at 45° under nitrogen, cooled, added to 150 ml of brine, and extracted with two 150 ml portions of ethyl acetate. The combined ethyl acetate extracts are washed with three 150 ml bicarb portions and two 150 ml portions of brine, and are dried over anhydrous sodium sulfate. The solvents are removed under reduced pressure to give a yellow oil which is chromatographed on silica gel eluting with 20% hexane in ethyl acetate to give 0.26 g (71%) of the title compound as a colorless oil ($R_f$ 0.25 in 20% hexane in ethyl acetate).

NMR (CDCl₃, TMS): δ0.90 (t, J=5 Hz, 3H), 1.08–3.15 (m, 22H), 3.25–4.6 (m including 3H singlet at 3.67δ, 7H), 5.1–5.8 (m, 3H).

Infrared: νmax (film): 3400, 2230, 1740, 1675, 1435, 1315, 1250, 1230, 1200, 1170, 1135, 1095, 1020, 970, 915, 890 cm⁻¹.

EXAMPLE 7

(5Z)-9β-Cyano-6a-carba-prostaglandin I₂

A solution of 0.14 g (0.36 mmol) of (5Z)-9β-cyano-6a-carba-prostaglandin I₂, methyl ester, 2.7 ml of 10% potassium hydroxide in 9:1 methanol-water, and 2.7 ml of 9:1 methanol-water is allowed to warm slowly from 0° to room temperature. After 17 hr the resulting solution is added to 60 ml of cold brine, acidified with 5 ml of 1N aqueous hydrochloric acid, and extracted with three 60 ml portions of ethyl acetate. The combined ethyl acetate extracts are washed with 60 ml of brine and dried over anhydrous sodium sulfate. The solvents are removed under reduced pressure and the residue chromatographed on 25 g of acid-washed silica gel eluting with 250 ml of 1:1 ethyl acetatehexane, then with 70% ethyl acetate in hexane to give 0.12 g (89%) of the title compound as a colorless oil ($R_f$ 0.29 in the organic phase of 9:2:5:10 ethyl acetate-acetic acid-cyclohexane-water).

NMR (CDCl₃, TMS): δ0.9 (t, J=5 Hz, 3H), 1.05–3.1 (m, 22H), 3.65–4.39 (m, 2H), 5.1–5.68 (m, 3H), 6.05 (bs, 3H).

Infrared: νmax (film): 3380, 2660, 2230, 1710, 1455, 1435, 1410, 1315, 1300, 1245, 1130, 1095, 1075, 1020, 970 cm⁻¹.

EXAMPLE 8

(5E)-9β-Cyano-6a-carba-prostaglandin I₂

A solution of 235 mg (0.60 mmol) of (5E)-9β-cyano-6a-carba-prostaglandin I₂, methyl ester, 4.5 ml of 10% potassium hydroxide in 9:1 methanol-water, and 4.5 ml of 9:1 methanol-water is stirred at 0° for 35 min and then at room temperature for 18 hr, added to 100 ml of cold brine, acidified with 8 ml of 1N aqueous hydrochloric acid, and extracted with three 100 ml portions of ethyl acetate. The combined ethyl acetate extracts are washed with 100 ml of brine and dried over anhydrous sodium sulfate. The solvents are removed under reduced pressure and the residue chromatographed on 30 g of acid-washed silica gel eluting with 300 ml of 1:1 ethyl acetate-hexane and then with 70% ethyl acetate in hexane to give 217 mg (96%) of the title compound as a colorless oil ($R_f$ 0.31 in the organic phase of 9:2:5:10 ethyl acetate-acetic acid-cyclohexane-water).

NMR (CDCl₃, TMS): δ0.91 (t, J=5 Hz, 3H), 1.06–3.2 (m, 22H), 3.6–4.4 (m, 2H), 5.12–5.8 (m, 3H), 6.27 (bs, 3H).

Infrared: νmax (film): 3380, 2660, 2230, 1735, 1710, 1455, 1435, 1410, 1300, 1245, 1170, 1130, 1095, 1025, 970 cm⁻¹.

EXAMPLE 9

(3′S)-1β-Hydroxymethyl-7α-tetrahydropyran-2-yloxy-6β[3′-tetrahydropyran-2-yloxy-trans-1′-octenyl]bicyclo[3.3.0]octan-3-one A degassed solution of 4.0 g (9.2 mmol) of (3′S)-7α-tetrahydropyran-2-yloxy-6β[3′-tetrahydropyran-2-yloxy-trans-1′-octenyl]bicyclo[3.3.0]octen-3-one and 2.0 g of benzophenone in one liter of methanol is photolyzed (3500 Å lamp) for 3 hr while bubbling argon through the solution. The methanol is removed under reduced pressure and the residue chromatogrpahed on 600 g silica gel with a gradient elution of from 3:1 hexane-ethyl acetate to 100% ethyl acetate to give 3.45 g (80%) of title produce as a waxy solid. Crystallization from ether and hexane gives the title compound as a white solid, mp 65°–70° ($R_f$ 0.29 in 20% hexane in ethyl acetate).

NMR (CDCl₃; TMS): δ0.89 (t, J=5 Hz, 3H), 1.07–2.90 (m, 28H), 2.92–4.40 (m including a 2H singlet at 3.50δ, 9H), 4.69 (bs, 2H), 5.24–5.77 (m, 2H).

Infrared: νmax (mull): 3420, 1730, 1200, 1125, 1110, 1070, 1040, 1020, 970 cm⁻¹.

EXAMPLE 10

5(Z)-9β-Hydroxymethyl-6a-carba-prostaglandin I₂, methyl ester, 11,15 bis(tetrahydropyranyl ether) and 5(E)-9β-hydroxymethyl-6a-carba-prostaglandin I₂, methyl ester, 11,15 bis(tetrahyropyranyl ether)

A degassed suspension of 3.53 g (94 mmol) of a mineral oil dispersion of sodium hydride (which had been washed twice with hexane) in 225 ml of dry dimethyl sulfoxide is heated at 65° for one hr under a nitrogen atmosphere, cooled to 15°, and treated portionwise over 15 min with 18.67 g (42.2 mmol) of 4-carboxybutyltriphenylphosphonium bromide. The resulting red solution is treated with a solution of 2.05 g (4.41 mmol) of (3'S) -1β-hydroxymethyl-7α-tetrahydropyran-2-yloxy-6β[3'-tetrahydropyran-2-yloxy-trans-1'-octenyl]-bicyclo[3.3.0]octan-3-one in 50 ml of dry dimethyl sulfoxide and then heated at 35°-40° under a nitrogen atmosphere for 90 hr. The resulting dark colored solution is cooled, treated with 30 ml of water, stirred for 30 min at about 20°, added to 500 ml of a 1:1 solution of brine and ice water, acidified with 1N aqueous HCl, and extraced with three 500 ml portions of ether. The combined ether extracts are washed with five 200 ml portions of water and once with 200 ml brine and are dried over anhydrous magnesium sulfate. The solvents are removed under reduced pressure to give 5.8 g of a red-brown oil.

A degassed solution of the 5.8 g of above crude product in 150 ml of acetonitrile at 11° under a nitrogen atmosphere is treated with 56 ml (320 mmol) of diisopropyl ethyl amine followed by 20 ml (320 mmol ) of methyl iodide. The resulting solution is stirred at ambient temperature for 20 hr, treated with an additional 4 ml of methyl iodide and stirred for 2 more hr, added to 500 ml of brine, and extracted with two 500 ml portions of ethyl acetate. The combined ethyl acetate extracts are washed with 250 mlof 0.5M aqueous potassium bisulfate solution, 250 ml of saturated aqueous sodium bicarbonate solution, and 250 ml of brine, and are dried over anhydrous sodium sulfate. The solvents are removed under reduced pressure and the residue filtered through 200 g silica gel eluting with 55:45 ethyl acetate-hexane to give 2.4 g of the title compounds.

Chromatography on of silica gel eluting with 55:45 ethyl acetate-hexane affords 0.59 g (24%) of the (5E) isomer as a colorless oil, 0.97 g (39%) of about a 1:1 mixture of both isomers and 0.52 g (21%) of the (5Z) isomer as a colorless oil.

Physical properties for the (5Z) isomer: R$_f$ 0.25 on 60:40 ethyl acetate-hexane.

NMR (CDCl₃; TMS): δ 0.89 (t, J=5 Hz, 3H), 1.07-2.80 (m, 35H), 3.2-4.33 (m including 3H singlet at 3.66 δ and 2H singlet at 3.39 δ, 11H), 4.64 (bs, 2H), 5.0-5.8 (m, 3H).

Infrared: νmax (film): 3475 (broad), 1740, 1200, 1120, 1035, 1020, 980 cm⁻¹.

Physical properties for the (5E) isomer: R$_f$ 0.29 in 60.40 ethyl acetate-hexane.

NMR (CDCl₃; TMS): δ 0.89 (t, J=5 Hz, 3H), 1.07-2.85 (m, 35H), 3.2-4.35 (m including 3H singlet at 3.65 δ and 2H singlet at 3.36 δ, 11H), 4.71 (bs, 2H), 5.0-5.8 (m, 3H).

Infrared: νmax (film): 3475 (broad), 1740, 1200, 1120, 1035, 1020, 980 cm⁻¹.

EXAMPLE 11

5(Z)-9β-Hydroxymethyl-6a-carba-prostaglandin I₂, methyl ester

A solution of 206 mg (0.37 mmol) of 5(Z)-9β-hydroxymethyl-6a-carba-prostaglandin I₂, methyl ester, 11,15 bis(tetrahydropyranyl ether) in 11 ml of 6:3:2 acetic acid-water-tetrahydrofuran is heated at 45° for 3 hr under an inert atmosphere, cooled, diluted with 75 ml brine, and extracted with two 75 ml portions of ethyl acetate. The combined ethyl acetate extracts are washed with three 75 ml portions of saturated aqueous sodium bicarbonate solution, twice with 75 ml brine, and are dried over anhydrous sodium sulfate. The solvents are removed under reduced pressure to give 0.16 g of a yellow oil which was chromatographed on silica gel eluting with 25% acetone in ethyl acetate to give 0.11 g (76%) of the title compound as a colorless oil (R$_f$ 0.22 in 25% acetone in methylene chloride).

NMR (CDCl₃; TMS): δ 0.90 (t, J=5 Hz, 3H), 1.07-2.8 (m, 22H), 3.0-4.3 (m including 3H singlet at 3.66 δ and 2H singlet at 3.36 δ, 10H), 5.0-5.8 (m, 3H).

Infrared: νmax (film): 3360 (broad), 1740, 1445, 1440, 1250, 1200, 1170, 1035, 970 cm⁻¹.

EXAMPLE 12

5(E)-9β-Hydroxymethyl-6a-carba-prostaglandin I₂, methyl ester

A solution of 286 mg (0.508 mmol) of 5(E)-9β-hydroxymethyl-6a-carba-prostaglandin I₂, methyl ester, 11,15 bis(tetrahydropyranyl ether) in a solution of 2.7 ml of tetrahydrofuran, 4 ml of water, and 8 ml of acetic acid is heated at 45° under a nitrogen atmosphere for 3 hr, cooled, diluted with 75 ml of brine, and extracted with three 60 ml portions of ethyl acetate. The combined ethyl acetate extracts are washed three times with 75 ml portions of saturated aqueous sodium bicarbonate and twice with 75 ml portions of brine and are dried over anhydrous sodium sulfate. The solvents are removed under reduced pressure to give a yellow oil which is chromatographed on silica gel eluting with 25% acetone in ethyl acetate to give 0.17 g (85%) of the title compound as a colorless oil (R$_f$0.22 in 25% EtOAc in hexane).

NMR (CDCl₃; TMS): δ 0.90 (t, J=5 Hz, 3H), 1.08-2.8 (m, 22H), 3.0-4.4 (m including 3H singlet at 3.66 δ and 2H singlet at 3.34 δ, 10H), 5.0-5.8 (m, 3H).

Infrared: νmax (film): 3360 (broad), 1740, 1455, 1440, 1250, 1200, 1170, 1135, 1070, 1050, 970 cm⁻¹.

EXAMPLE 13

5(Z)-9β-Hydroxymethyl-6a-carba-prostaglandin I₂

A solution of 0.10 g (0.25 mmol) of 5(Z)-9β-hydroxymethyl-6a-carba-prostaglandin I₂, methyl ester in 2 ml of 9:1 methanol-water at 0° is treated with 2 ml of a 10% solution of potassium hydroxide in 9:1 methanol-water. The resulting solution is stirred at 0° for one hr and then at room temperature for 6 hr, and then is diluted with 70 ml of 1:1 ice water-brine, acidified with 1N aqueous hydrochloric acid solution, and extracted with three 100 ml of brine and dried over anhydrous sodium sulfate. The solvents are removed under reduced pressure to give an oil which is chromatographed on silica gel eluting with 1:7:92 acetic acid-methanol-ethyl acetate to give 76 mg (79%) of the title compound as a colorless oil.

NMR (CD$_3$COCD$_3$; TMS): δ 0.90 (t, J=5 Hz, 3H), 1.07–2.7 (m, 22H), 3.36 (s, 2H), 3.45–4.2 (m, 2H), 4.81 (s, 4H), 5.0–5.75 (m, 3H).

Infrared: νmax (film): 3350 (broad), 1710, 1030, 970 cm$^{-1}$.

EXAMPLE 14

5(E)-9β-Hydroxymethyl-6a-carba-prostaglandin I$_2$

A solution at 0° of 0.14 g (0.35 mmol) of 5(E)-9β-hydroxymethyl-6a-carba-prostaglandin I$_2$, methyl ester in 2.5 ml of 9:1 methanol-water and 2.5 ml 10% potassium hydroxide in 9:1 methanol-water is allowed to warm slowly to room temperature. After 18 hr the solution is added to 70 ml of an ice water-brine solution, acidified with 1N aqueous hydrochloric acid solution, and extracted with three 100 ml portions of ethyl acetate. The combined ethyl acetate extracts are washed with 100 ml of brine and dried over anhydrous sodium sulfate. The solvents are removed under reduced pressure to give 0.13 g of an oil which is chromatographed on acid-washed silica gel eluting with 5% methanol in ethyl acetate to give 10–16) 0.13 g (96%) of the title compound as a very viscous colorless oil.

NMR (CD$_3$COCD$_3$, TMS): δ 0.90 (t, J=5 Hz, 3H), 1.06–2.7 (m, 22H), 3.35 (s, 2H), 3.45–4.35 (m, 2H), 4.4–6.0 (m, 7H).

Infrared: νmax (film): 3340 (broad), 2660, 1710, 1240, 1030, 970 cm$^{-1}$.

EXAMPLE 15

(5Z)-9β-Hydroxymethyl-6a-carba-prostaglandin I$_2$, methyl ester, 11,15-bis(t-butyldimethylsilyl ether) and (5E)-9b-Hydroxymethyl-6a-carba-prostaglandin I$_2$, methyl ester, 11,15-bis(t-butyldimethylsilyl ether)

(a) A solution of 695 mg (1.23 mmol) of 9β-hydroxymethyl-6a-carba-prostaglandin I$_2$, methyl ester, 11,15-bis(tetrahydropyranyl ether) and 1 ml of acetic anhydride in 5 ml of pyridine is stirred at room temperature under argon for 23 hr. Most of the pyridine is removed under reduced pressure using a cyclohexane azeotrope to give a residue which is chromatographed on silica gel eluting with 3:1 hexane-ethyl acetate to give 686 mg (92%) of 9β-acetoxymethyl-6a-carba-prostaglandin I$_2$, methyl ester, 11,15-bis(tetrahydropyranyl ether).

Without further purification a total of 0.68 g (0.11 mmol) of thus obtained acetate bis ether is dissolved in 28 ml of 1:2:4 THF-water-acetic acid and heated at 45° under nitrogen for 2.5 hr, cooled, added to 150 ml of brine, and extracted with two 150 ml portions of ethyl acetate. The combined ethyl acetate extracts are washed with three 150 ml portions of bicarb and two 150 ml portions of brine and are dried over anhydrous sodium sulfate. The solvents are removed under reduced pressure and the residue chromatographed on silica gel eluting with 9:1 ethyl acetate-hexane to give 0.49 g (100%) of 9β-acetoxymethyl-6a-carba-prostaglandin I$_2$, methyl ester as a clear, colorless oil.

(b) A solution of 0.46 g (1.0 mmol) of the above-obtained 9β-acetoxymethyl derivative and 0.32 mmol (4.7 mmol) of imidazole in 6 ml of dimethylformamide at 0° is treated with 0.36 g (2.4 mmol) of t-butyldimethylsilyl ether, stirred at ambient temperature under argon for 70 hr, added to 40 ml of water, and extracted with three 40 ml portions of ether. The combined ether extracts are washed with 40 ml of 10% aqueous potassium bisulfate, 40 ml of bicarb, and 40 ml of brine and are dried over anhydrous sodium sulfate. The solvents are removed in vacuo to give 0.70 g (100%) of 9β-acetoxymethyl-6a-carba-prostaglandin I$_2$, methyl ester, 11,15-bis(t-butyldimethylsilyl ether) as a coloress oil.

Without further purification 0.66 g (1.0 mmol) of the bis ether is dissolved in 4 ml of methanol, treated with 0.3 ml (1.4 mmol) of 25% sodium methoxide in methanol, stirred at room temperature for 1¼ hr, added to 50 ml of bicarb and extracted with two 50 ml portions of ethyl acetate. The combined ethyl acetate extracts are washed with 30 ml of bicarb and 30 ml of brine and are dried over anhydrous sodium sulfate. The solvents are removed under reduced pressure and the residue then chromatographed on silica gel to give 0.36 g (51%) of the title (5Z) isomer and 0.22 g (31%) of the title (5E) isomer, both colorless oils.

For the (5E) isomer: R$_f$0.27 in 5:1 hexane-ethyl acetate.

NMR (CDCl$_3$; TMS): δ 0.01 (s, 12H), 0.86 and 0.89 (two singlets, 21H), 1.05–2.6 (m, 23H), 3.36 (s, 2H), 3.5–4.3 (m including 3H singlet at 3.66 δ, 5H), 5.0–5.67 (m, 3H).

Infrared: νmax (film): 3470, 1745, 1725, 1465, 1475, 1250, 1120, 1095, 1060, 1010, 970, 835 cm$^{-1}$.

For the (5Z) isomer: R$_f$0.23 in 5:1 hexane-ethyl acetate.

NMR (CDCl$_3$; TMS): δ 0.02 (s, 12H), 0.86 and 0.89 (two singlets, 21H), 1.05–2.8 (m, 23H), 3.35 (s, 2H), 3.5–4.3 (m including 3H singlet at 3.65δ, 5H), 5.0–5.67 (m, 3H).

Infrared: νmax (film): 3470, 1745, 1725, 1250, 1126, 1095, 1060, 970, 835, 775 cm$^{-1}$.

EXAMPLE 16

(5Z)-9β-Vinyl-6a-carba-prostaglandin I$_2$, 11,15-bis(t-butyldimethylsilyl ether)

A solution of 237 mg (0.38 mmol) of (5Z)-9β-hydroxymethyl-6a-carba-prostaglandin I$_2$, methyl ester, 11,15-bis(t-butyldimethylsilyl ether) in 4.4 ml of methylene chloride at ambient temperature under nitrogen is treated with one scoop of oven dried celite and then with 6.6 ml of Collins reagent (prepared from 1.54 g chromium trioxide in 50 ml of methylene chloride which is treated with 2.5 ml of pyridine and stirred at ambient temperature for 35 min), stirred at ambient temperature for 30 min, and filtered through 10 g of silica gel eluting with 100 ml of ethyl acetate. The solvents are removed under reduced pressure and the residue chromatographed on silica gel eluting with 14:1 hexane-ethyl acetate to give 185 mg (78%) of aldehyde, that is, (5Z)-9β-formyl-6a-carba-prostaglandin I₂, methyl ester, 11,15-bis-(t-butyldimethylsilyl ether) (R$_f$ 0.18 in 14:1 hexane-ethyl acetate).

Without further purification 184 mg (0.30 mmol) of the thus obtained aldehyde is dissolved in 3 ml of 9:1 methanol-water, cooled to 0°, treated with 3 ml of 10% potassium hydroxide in 9:1 methanol-water, stirred at 0° for one hr and room temperature for 4 hr, added to 50 ml 1:1 ice-brine, acidified with 5 ml 1N aqueous hydrochloric acid, and extracted with three 50 ml portions of ethyl acetate. The combined ethyl acetate extracts are washed with 50 ml of brine and dried over anhydrous sodium sulfate. The solvents are removed under reduced pressure and the residue chromatographed on 20 g of acid-washed silica gel eluting with 150 ml of 10% ethyl acetate in hexane and then with 20% ethyl acetate in hexane to give 171 mg (95%) of (5Z)-9β-formyl-6a-carba-prostaglandin I₂, 11,15-bis(t-butyldimethylsilylether) which is used without further purification.

A suspension of 100 mg (2.38 mmol) of sodium hydride (a 57% solution in mineral oil which is washed twice with hexane) in 25 ml of dry dimethylsulfoxide at room temperature under argon is treated with 0.85 g (2.38 mmol) of methyltriphenylphosphonium bromide, and stirred for one hr at room temperature. The resulting yellow solution is treated with 165 mg (0.272 mmol) of (5Z)-9β-formyl-6a-carba-prostaglandin I₂, 11,15-bis(t-butyldimethylsilylether) in 5 ml of dry dimethylsulfoxide (DMSO). The resulting suspension is stirred at room temperature under argon for 20 hr, quenched with 1 ml of water, added after 30 min to 50 ml of 1:1 water-brine containing 2 ml of 1M HCl, and extracted with three 50 ml portions of ether. The combined ether extracts are washed with five 50 ml portions of water and one 50 ml portion of brine and dried over anhydrous magnesium sulfate. The solvents are removed under reduced pressure and the residue chromatographed on acid-washed silica gel eluting with 10% ethyl acetate in hexane to give 164 mg (100%) of the title compound as a colorless oil (R$_f$ 0.38 in 84:15:1 hexane-ethyl acetate-acetic acid).

NMR (CDCl₃; TMS): δ 0.02 (s, 12H), 0.86 and 0.89 (two singlets, 21H), 1.0–2.7 (m, 22H), 3.67–4.2 (m, 2H), 4.78–6.13 (m, 6H), 10.7 (broad singlet, 1H).

Infrared: νmax (film): 2950 (broad), 1710, 1635, 1460, 1465, 1255, 1110, 970 cm⁻¹.

EXAMPLE 17

(5Z)-9β-Vinyl-6a-carba-prostaglandin I₂

A suspension of 160 mg (0.26 mmol) of (5Z)-9β-vinyl-6a-carba-prostaglandin I₂, 11,15-bis(t-butyldimethylsilyl ether) in 14 ml of 4:2:1 acetic acid-water-tetrahydrofuran is heated at 45° under nitrogen for 5 hr, cooled, diluted with 50 ml of brine, and extracted with two 50 ml portions of 3:2 ethyl acetate-hexane. The combined organic extracts are washed with four 50 ml portions of brine, and the combined brine washes are extracted with an additional 80 ml of 3:2 ethyl acetate-hexane. The combined organic extracts are dried over anhydrous sodium sulfate. The solvents are removed under reduced pressure and the residue chromatographed on 25 g of silica gel eluting with 100 ml of 1:1 ethyl acetate-hexane and then with 2:1 ethyl acetate-hexane to give 80 mg (80%) of the title compound (R$_f$ 0.35 in the organic phase of 9:2:5:10 ethyl acetate-acetic acid-cyclohexane-water).

EXAMPLE 18

9β-Formyl-6a-carba-prostaglandin I₂, methyl ester, 11,15-bis(tetrahydropyranyl ether)

A solution of 0.88 g (1.56 mmol) of 9β-hydroxymethyl-6a-carba-prostaglandin I₂, methyl ester, 11,15-bis(tetrahydropyranyl ether) in 18 ml of methylene chloride is treated with two scoops of over-dried celite, then treated with 27 ml of Collins reagent (prepared from 1.54 g of chromium trioxide in 50 ml of methylene chloride treated with 2.5 ml of pyridine), stirred for 30 min at ambient temperature, and filtered through 25 g of silica gel eluting with 130 ml of ethyl acetate. The solvents are removed udner reduced pressure and the residue chromatographed on silica gel eluting with 25% ethyl acetate in hexane to give 0.77 g (88%) of the title compound as a colorless oil (R$_f$ 0.22 in 25% ethyl acetate in hexane).

NMR (CDCl₃; TMS): δ 0.88 (t, J=5 Hz, 3H), 1.0–2.9 (m, 34H), 3.25–4.3 (m including 3H singlet at 3.66δ, 9H), 5.0–5.75 (m, 3H), 8.57 (s, 1H), 4.72 (bs, 2H).

Infrared: νmax (film): 2700, 1740, 1725, 1200, 1130, 1080, 1035, 1020, 975 cm⁻¹.

EXAMPLE 19

9β-Formyl-6a-carba-prostaglandin I₂, methyl ester

A solution of 278 mg (0.496 mmol) of 9β-formyl-6a-carba-prostaglandin I₂, methyl ester, 11,15-bis(tetrahydropyranyl ether) in 1.75 ml of tetrahydrofuran, 3.5 ml of water, and 7.0 ml of glacial acetic acid is heated at 45° under nitrogen for 3 hr, cooled, diluted with 75 ml of brine, and extracted with two 75 ml portions of ethyl acetate. The combined ethyl acetate extracts are washed with three 75 ml portions of bicarb and two 75 ml portions of brine and are dried over anhydrous sodium sulfate. The solvents are removed under reduced pressure and the residue chromatographed on silica gel eluting with 9:1 ethyl acetate-hexane to give 168 mg (86%) of the title compound as a colorless oil (R$_f$ 0.21 in 9:1 ethyl acetate-hexane).

NMR (CDCl₃; TMS): δ 0.89 (t, J=5 Hz, 3H), 1.05–3.3 (m, 24H), 3.3–4.5 (singlet including 3H singlet at 3.66δ, 5H), 5.0–5.8 (m, 3H), 8.56 (s, 1H).

Infrared: νmax (film): 1740, 1720, 1675, 1435, 1315, 1250, 1230, 1200, 1170, 1135, 1075, 1025, 1020, 970 cm⁻¹.

EXAMPLE 20

(5Z)-9β-Formyl-6a-prostaglandin I₂

A suspension of 150 mg (0.38 mmol) of 9β-formyl-6a-carba-prostaglandin I₂, methyl ester, 0.12 g (1.8 mmol) of imidazole, and 0.13 g (0.83 mmol) of t-butyldimethylsilyl chloride in 3 ml of dimethylformamide is combined at 0° and then stirred at ambient temperature for 65 hr, added to 40 ml of water, and extracted with three 40 ml portions of ether. The combined ether extracts are washed with 40 ml of 10% aqueous potassium bisulfate, 40 ml of bicarb, and 40 ml of brine, and are dried over anhydrous sodium sulfate. The solvents are removed under reduced pressure and the residue chromatographed on silica gel eluting with 20:1 hexane-ethyl acetate to give 190 mg (80%) of the corresponding 11,15-bis(t-butyldimethylsilyl ether) as a colorless oil ($R_f$ 0.16 in 20:1 hexane-ethyl acetate).

Without further purification the 0.19 g (0.306 mmol) of the thus obtained bis-ether is dissolved in 3 ml of 9:1 methanol-water, cooled to 0°, treated with 3 ml of 10% potassium hydroxide in 9:1 methanol-water, stirred for one hr at 0° and then at room temperature for 6 hr, added to 50 ml of 1:1 ice-brine, acidified with 5 ml of 1N aqueous HCl, and extracted with three 50 ml of 1N aqueous HCl, and extracted with three 50 ml portions of ethyl acetate. The combined ethyl acetate extracts are washed with 50 ml of brine and dried over anhydrous sodium sulfate. The solvents are removed under reduced pressure and the residue chromatographed on acid-washed silica gel eluting with 5% ethyl acetate in hexane to give 23 mg (12%) of (5E)-9β-formyl-6a-carba-prostaglandin $I_2$, 11,15-bis(t-butyldimethylsilyl ether) ($R_f$ 0.24 in 84:15:1 hexane-ethyl acetate-acetic acid), 85 mg (46% of (5Z)-9β-formyl-6a-carba-prostaglandin $I_2$, 11,15-bis(t-butyldimethylsilyl ether) ($R_f$ 0.20 in 84:15:1 hexane-ethyl acetate-acetic acid) and 54 mg (29%) of a mixture of said isomers.

Without further purification the 85 mg (0.14 mmol) of (5Z)-9β-formyl-6a-carba-prostaglandin $I_2$, 11,15-bis(t-butyldimethylsilyl ether) is dissolved in 5 ml of tetrahydrofuran, cooled to 0°, treated with 1.0 ml (0.75 mmol) of 0.75M tetra-n-butylammonium fluoride in tetrahydrofuran, stirred at ambient temperature for 40 hr, added to 50 ml of brine, and extracted with three 50 ml portions of ethyl acetate. The combined ethyl acetate extracts are washed with 50 ml of brine and dried over anhydrous sodium sulfate. The solvents are removed under reduced pressure and the residue chromatographed on 9 g of acid-washed silica gel eluting with 30 ml of 1:1 ethyl acetate-hexane, then with 30 ml of 70:30 ethyl acetate-hexane, then with ethyl acetate to give 21.4 mg (40%) of the title compound as a viscous colorless oil ($R_f$ 0.28 in the organic phase of 9:2:5:10 ethyl acetate-acetic acid-cyclohexane-water).

NMR (CDCl$_3$; TMS): δ 0.88 (t, J=5 Hz, 3H), 1.0–2.9 (m, 22H), 3.3–4.5 (m, 2H), 4.9–6.2 (m including 3H broad singlet at 5.53δ, 6H), 8.57 (s, 1H).

EXAMPLE 21

9β-Vinyl-6a-carba-prostaglandin $I_2$, methyl ester, 11,15-bis(tetrahydropyranyl ether)

A suspension of 0.69 g (1.9 mmol) of methyl triphenylphosphonium bromide in 15 ml of tetrahydrofuran at −70° under argon is treated with 1.1 ml (1.8 mmol) of 1.6M n-butyllithium in hexane, stirred for 2 hr at room temperature, cooled to −70°, treated dropwise with a solution of 0.54 g (0.96 mmol) of 9β-formyl-6a-carba-prostaglandin $I_2$, methyl ester, 11,15-bis(tetrahydropyranyl ether) in 5 ml of tetrahydrofuran, and warmed slowly to room temperature. After 16 hr the resulting suspension is quenched with 10 ml of bicarb, added to 250 ml ether, and washed with two 50 ml bicarb portions and one 50 ml brine portion. The combined aqueous washes are extracted with an additional 100 ml of ether, and the combined organic layers dried over anhydrous magnesium sulfate. The solvents are removed under reduced pressure and the residue chromatographed on silica gel eluting with 7:1 hexane-ethyl acetate to give 174 mg of the title compound as a colorless oil ($R_f$ 0.21 in 7:1 hexane-ethyl acetate).

NMR (CDCl$_3$; TMS): δ 0.88 (t, J=5 Hz, 3H), 1.0–2.7 (m, 34H), 3.0–4.25 (m, including 3H singlet at 3.66δ, 9H), 4.4–6.2 (m, including 2H broad singlet at 4.66δ, 8H).

Infrared: νmax (film): 1740, 1635, 1470, 1200, 1115, 1075, 1035, 1020, 975 cm$^{-1}$.

EXAMPLE 22

(5Z)-9β-Vinyl-6a-carba-prostaglandin $I_2$

A solution of 0.16 g (0.29 mmol) of 9β-vinyl-6a-carba-prostaglandin $I_2$, methyl ester, 11,15-bis(tetrahydropyranyl ether) and 3 ml of 10% potassium hydroxide (in 9:1 methanol-water) in 3 ml of 9:1 methanol-water is stirred at 0° for one hr and then for three hr at room temperature, added to 50 ml of 1:1 ice water-brine, acidified with 5 ml of 1n aqueous hydrochloric acid, and extracted with three 50 portions of ethyl acetate. The combined ethyl acetate extracts are washed with 50 ml of brine and dried over anhydrous sodium sulfate. The solvents are removed under reduced pressure and the residue chromatographed on 50 g of acid-washed silica gel eluting with 500 ml of 7.5% ethyl acetate in hexane, 500 ml of 10% ethyl acetate in hexane, 500 ml of 12.5% ethyl acetate in hexane and, 500 ml of 20% ethyl acetate in hexane to give 33 mg (21%) of (5E)-9β-vinyl-6a-carba-prostaglandin $I_2$, 11,15-bis-(tetrahydropyranyl ether) ($R_f$ 0.31 in 74:25:1 hexane-ethyl acetate-acetic acid), 80 mg (51%) of (5Z)-9β-vinyl-6a-carba-prostaglandin $I_2$, 11,15-bis(tetrahydropyranyl ether) ($R_f$ 0.28 in 74:25:1 hexane-ethyl acetate-acetic acid) and 40 mg (26%) of 1:1 mixture of said isomers.

Without further purification 74 mg (0.136 mmol) of (5Z)-9β-vinyl-6a-carba-prostagandin $I_2$, 11,15-bis(tetrahydropyranyl ether) is dissolved in 0.8 ml of tetrahydrofuran, 1.5 ml of water, and 3.0 ml of glacial acetic acid, and the resulting solution is stirred for 2.5 hr at 45° under nitrogen, cooled, added to 50 ml of brine, and extracted with two 50 ml portions of ethyl acetate. The combined ethyl acetate extracts are washed with 50 ml of brine and dried over anhydrous sodium sulfate. The solvents are removed under reduced pressure and the residue chromatographed on 25 g of acid-washed silica gel eluting with 100 ml of 1:1 hexane-ethyl acetate and then with 2:1 ethyl acetate-hexane to give 42 mg (82%) of the title compound as a colorless oil.

NMR (CDCl$_3$; TMSA): δ 0.88 (t, J=5 Hz, 3H), 1.0–2.7 (m, 22H), 3.3–4.2 (m, 2H), 4.6–6.3 (m including 3H broad singlet at 5.59δ, 9H).

Infrared: νmax (film): 3325, 1710, 1635, 1070, 975 cm$^{-1}$.

EXAMPLE 23

(5Z)-9-Chloromethyl-6a-carba-prostaglandin I$_2$, methyl ester, 11,15-bis(t-butyldimethylsilyl ether)

A degassed solution of 234 mg (0.38 mmol) of (5Z)-9β-hydroxymethyl-6a-carba-prostaglandin I$_2$, methyl ester, 11,15-bis(t-butyldimethylsilyl ether) and 0.50 g (1.9 mmol) of triphenylphosphine in 5 ml of carbon tetrachloride is refluxed for 15 hr under nitrogen, cooled, added to 50 ml of brine, and extracted with three 50 ml portions of ethyl acetate. The combined ethyl acetate extracts are washed with 50 ml of brine and dried over anhydrous magnesium sulfate. The solvents are removed under reduced pressure and the residue chromatographed on 60 g of silica gel eluting with 400 ml 5% ethyl acetate in hexane then with 3:1 hexane-ethyl acetate to give 60 mg (26%) of starting alcohol and 0.50 g of the title product contaminated with triphenylphosphine.

The 0.50 g of impure product is chromatographed on silica gel eluting with 700 ml of hexane and then 10% ethyl acetate in hexane to give 163 mg (68%) of the purified title compound as a colorless oil ($R_f$ 0.28 in 5% ethyl acetate in hexane).

NMR (CDCl$_3$; TMS): δ 0.02 (s, 12H), 0.85 and 0.89 (two singlets, 21H), 1.0–2.5 (m, 22H), 3.39 (s, 2H), 3.5–4.2 (m including 3H singlet at 3.66δ, 5H), 5.0–5.5 (s, 3H).

Infrared: νmax (film): 1745, 1250, 1120, 1010, 970 cm$^{-1}$.

EXAMPLE 24

(5Z)-9-Chloromethyl-6a-carba-prostaglandin I$_2$, methyl ester

A solution of 0.15 g (0.23 mmol) (5Z)-9-chloromethyl-6a-carba-prostaglandin I$_2$, methyl ester, 11,15-bis(t-butyldimethylsilyl ether) and 1.2 ml (0.90 mmol) 0.75M tetra-n-butylammonium fluoride (in tetrahydrofuran) in 5 ml of dry tetrahydrofuran is allowed to slowly warm from 0° to room temperature, and after 30 hr diluted with 75 ml of brine and extracted with two 75 ml portions of ethyl acetate. The combined ethyl acetate extracts are washed with 50 ml of 0.5M aqueous potassium bisulfate, 50 ml of bicarb, and 50 ml of brine, and are dried over anhydrous sodium sulfate. The solvents are removed under reduced pressure and the residue chromatographed on silica gel eluting with 20% hexane in ethyl acetate to give 90 mg (93%) of the title compound as a colorless oil ($R_f$ 0.28 in 20% hexane in ethyl acetate).

NMR (CDCl$_3$; TMS): δ 0.88 (t, J=5 Hz, 3H), 1.0–2.6 (m, 24H), 2.6–4.15 (m including 2H singlet at 3.42δ and 3H singlet at 3.67δ, 7H), 5.0–5.55 (m, 3H).

Infrared: νmax (film): 3365, 1740, 1670 (weak), 1455, 1435, 1375, 1280, 1250, 1225, 1200, 1170, 1070, 1020, 970.

EXAMPLE 25

(5Z)-9β-Chloromethyl-6a-carba-prostaglandin I$_2$

A solution of 68 mg (0.16 mmol) of (5Z)-9-chloromethyl-6a-carba-prostaglandin I$_2$, methyl ester and 2 ml of 10% potassium hydroxide (in 9:1 methanol-water) and 2 ml of 9:1 methanol-water is allowed to warm slowly from 0° to room temperature. After 14 hr the resulting solution is added to 50 ml of 1:1 ice-brine, acidified with 1N aqueous HCl and extracted with three 65 ml portions of ethyl acetate. The combined ethyl acetate extracts are washed with 50 ml of brine and dried over anhydrous sodium sulfate. The solvents are removed under reduced pressure and the residue chromatographed on 25 g of acid-washed silica gel eluting with 100 ml of 1:1 ethyl acetate-hexane and then with 2:1 ethyl acetate-hexane to give 64 mg (97%) of the title compound as a colorless oil ($R_f$ in the organic phase of 9:2:5:10 ethyl acetate-acetic acid-cyclohexane-water).

NMR (CDCl$_3$; TMS): δ 0.89 (t, J=5 Hz, 3H), 1.0–2.7 (m, 22H), 2.8–4.3 (m including 2H singlet at 3.41δ, 4H), 5.0–6.0 (m including 3H broad singlet at 5.71δ, 6H).

Infrared: νmax (film): 3350, 1705, 1435, 1280, 1240, 1070, 970 cm$^{-1}$.

EXAMPLE 26

(a)

(3'S)-1β-(1'-Pentynyl)-7α-tetrahydropyran-2-yloxy-6β-[3'-tetrahydropyran-2-yloxy-trans-1'-octenyl]-bicyclo[3.3.0]octan-3-one A solution of 1.96 g (28.8 mmol) of 1-pentyne in 50 ml of ether at −35° under N$_2$ is treated with 18 ml (28.8 mmol) of 1.6M n-butyllithium in hexane. The resulting white suspension is stirred for 10 min at −35°, then treated with 14 ml (29 mmol) of 25% diethylaluminum chloride in hexane, stirred at 0° for one hr, and cannulated into a −5° to −10° solution of 0.74 g (2.88 mmol) of nickel-2,4-pentanedionate and 2.6 ml (2.6 mmol) of 1.0M diisobutylaluminum hydride (in hexane) in 50 ml of ether. The resulting black suspension is treated with 5.65 g (13.1 mmol) of (3'S)-7α-tetrahydropyran-2-yloxy-6β-[3'-tetrahydropyran-2-yloxy-trans-1'-octenyl]-bicyclo-[3.3.0]octen-3-one in 30 ml of ether, stirred for 3 hr between −10° and 0°, and cannulated into an ice cold solution of saturated sodium hydrogen phosphate (200 ml). The layers are separated and the aqueous layer extracted with an additional two 200 ml portions of ether. The combined ether extracts are washed with three 100 ml portions of brine, dried over magnesium sulfate, and filtered through celite. The solvents are removed under reduced pressure and the residue chromatographed on silica gel eluting with 4:1 hexane-ethyl acetate to give 4.17 g (64%) of the above title compound (a) ($R_f$ 0.32 in 4:1 hexane-ethyl acetate).

NMR (CDCl$_3$, TMS): δ 0.94 (t, J=5 Hz, 6H), 1.07–3.22 (m, 32H), 3.22–4.4 (m, 6H), 4.64 (bs, 2H), 5.1–5.82 (m, 2H).

Infrared: νmax (film): 1745, 1455, 1340, 1200, 1155, 1130, 1115, 1075, 1035, 1020, 975, 870 cm$^{-1}$.

(b) 9β-(1'-Pentynyl)-6a-carba-prostaglandin I$_2$, 11,15-bis-(tetrahydropyranyl ether)

A twice hexane-washed mineral suspension of sodium hydride (3.62 g, 86 mmol) in 260 ml of dry dimethylsulfoxide is heated at 65° for one hr, cooled to 15°, treated over 10 min with 19.1 g (43 mmol) of (4-carboxybutyl)-triphenyl phosphonium bromide, stirred at 15° for 20 min, treated with 3.90 g (7.79 mmol) of (3'S)-1β-(1'-pentynyl)-7α-tetrahydropyran-2-yloxy-6β-[3'-tetrahydropyran-2-yloxy-trans-1'-octenyl]-bicyclo-[3.3.0]octan-3-one in 40 ml of dry DMSO, stirred at 40° under argon for 88 hr, cooled to 0°, treated with 30 ml of water, stirred at 0° for 2 hr, added to a solution of 5.5 ml of sulfuric acid in 200 ml of 7:3 water-brine, and extracted with three 200 ml portions of ether. The combined ether extracts are washed with five 200 ml portions of water and one 200 ml brine portion and are dried (MgSO$_4$). The solvents are removed under reduced pressure to give 6 g of a brown oil which is chromatographed (gradient elution) on acid-washed silica gel eluting from 10% ethyl acetate in hexane to 20% ethyl acetate in hexane to give 3.2 g (70%) of the above title compound (b) (R$_f$0.46 in 64:35:1 hexane-ethyl acetate-acetic acid).

NMR (CDCl$_3$, TMS): δ 0.94 (t, J=5 Hz, 6H), 1.07-2.95 (m, 38H), 3.2-4.3 (m, 6H), 4.63 (bs, 2H), 497-5.9 (m, 3H), 7.25 (s, 1H).

Infrared: νmax (film): 2238, 1740, 1710, 1455, 1440, 1200, 1185, 1160, 1130, 1075, 1035, 1020, 975, 870 cm$^{-1}$.

(c) (5E)-9β-(1'-Pentynyl)-6a-carba-prostaglandin I$_2$ and (5Z)-9β-(1'-Pentynyl)-6a-carba-prostaglandin I$_2$ A solution of 0.63 g (1.08 mmol) of 9β-(1'-pentynyl)-6a-carba-prostaglandin I$_2$, 11,15-bis-(tetrahydropyranyl ether) in 4 ml of tetrahydrofuran, 6 ml of water, and 12 ml of acetic acid is heated at 40°-45° for 3 hr, cooled, diluted with 50 ml of brine, and extracted with two 50 ml portions of 3:2 ethyl acetate-hexane. The combined organic extracts are washed with four 50 ml portions of brine. The combined brine washes are extracted with another 80 ml of 3:2 ethyl acetate-hexane. The organic fractions are dried (Na$_2$SO$_4$), the solvents removed under reduced pressure (toluene azeotrope). Chromatography on silica gel eluting with 1000:40:5 chloroform-methanol-acetic acid gave 0.13 g (29%) of the title (5E) isomer, 0.09 g (20%) of a mixture of the title isomers, and 0.21 g (47%) of the title (5Z) isomer.

The (5E) compound: R$_f$0.44 in the organic phase of 9:2:5:10 ethyl acetate-acetic acid-cyclohexane-water.

NMR (CDCl$_3$, TMS): δ 0.5-3.0 (m, 32H), 3.65-4.3 (m, 2H), 5.08-6.2 (m including 3H broad singlet at 5.8δ, 6H).

Infrared: νmax (film): 3340 (broad), 2235 (weak), 1710, 1455, 1430, 1340, 1330, 1250, 1240, 1085, 970 cm$^{-1}$.

The (5Z) compound: R$_f$0.43 in the organic phase of 9:2:5:10 ethyl acetate-acetic acid-cyclohexane-water.

NMR (CDCl$_3$, TMS): δ 0.95 (t, J=9 Hz, 6H), 1.1-3.0 (m, 26H), 3.7-4.3 (m, 2H), 4.98-5.68 (m, 3H), 5.99 (bs, 3H).

Infrared: νmax (film): 3340 (broad), 2235 (weak), 1710, 1455, 1430, 1340, 1330, 1250, 1240, 1085, 970 cm$^{-1}$.

EXAMPLE 27

(a)
(3'S)-1β-Trimethylsilylethynyl-7α-tetrahydropyran-2-yloxy-6β-[3'-tetrahydropyran-3-yloxy-trans-1'-octenyl]bicyclo[3.3.0]octan-3-one A solution of 1.5 ml (6.6 mmol) of bis(trimethylsilyl)acetylene (BTMSA) in 10 ml of dry tetrahydrofuran at room temperature under nitrogen is treated dropwise with 4.8 ml (6.7 mmol) of 1.4M methyllithium-lithium bromide complex in ether. After 3 hr the solution is cooled to 0° and most of the tetrahydrofuran removed under high vacuum. The oily residue at 0° is taken up in 10 ml of ether, and the resulting cloudy suspension is treated with 3.2 ml (6.6 mmol) of 25% diethylaluminum chloride in hexane. The resulting white suspension is stirred for one hr at 0° and cannulated into a −10° solution of 0.17 g (0.66 mmol) of nickel-2,4-pentanedionate and 0.6 ml (0.6 mmol) of 1M diisobutylaluminum hydride (in hexane) in 10 ml of ether. The resulting black solution is treated with 1.3 g (3.0 mmol) of (3'S)-7α-tetrahydropyran-2-yloxy-6β-[3'-tetrahydropyran-3-yloxy-trans-1'-octenyl]bicyclo[3.3.0]octen-3-one in 15 ml of ether, stirred for 3 hr at −10° to 0°, added to 100 ml cold saturated sodium hydrogen phosphate, and extracted with three 100 ml portions of ether. The combined ether extracts are washed with two 100 ml brine portions, dried over anhydrous magnesium sulfate, and filtered through celite. The solvents are removed under reduced pressure to give 1.8 g of a black oil which is chromatographed on silica gel eluting with 15% ethyl acetate in hexane to give 1.0 g (63%) of the title compound (a) (R$_f$0.38 in 4:1 hexane-ethyl acetate).

(b)
(3'S)-1β-Ethynyl-7α-tetrahydropyran-2-yloxy-6β-[3'-tetrahydropyran-2-yloxy-trans-1'-octenyl]bicyclo[3.3.0]octan-3-one A suspension of 1.0 g (1.88 mmol) of (3'S)-1β-trimethylsilylethynyl-7α-tetrahydropyran-2-yloxy-6β-[3'-tetrahydropyran-3-yloxy-trans-1'-octenyl]-bicyclo[3.3.0]octan-3-one and 0.35 g (3.72 mmol) of potassium fluoride dihydrate in 30 ml of dimethylformamide is stirred at 0° under nitrogen for 3¾ hr, diluted with 100 ml of brine, and extracted with three 100 ml portions of 1:1 hexane-ether. The combined organic extracts are washed with three 100 ml portions of water, one 100 ml brine portion, and dried (MgSO$_4$). The solvents are removed under reduced pressure and the residue chromatographed on silica gel eluting with 20% ethyl acetate in hexane to give 0.72 g (83%) of the compound (b) as a pale yellow oil (R$_f$ 0.27 in 20% ethyl acetate in hexane).

NMR (CDCl$_3$, TMS): δ 0.89 (t, J=5 Hz, 3H), 1.04-3.0 (m including 1H singlet at 2.25 δ, 29H), 3.26-4.42 (m, 6H), 4.67 (bs, 2H), 5.05-5.8 (m, 2H).

Infrared: νmax (film): 3285, 2110, 1750, 1200, 1155, 1130, 1075, 1035, 1020, 995, 975 cm$^{-1}$.

(c) 9β-Ethynyl-6a-carba-prostaglandin I$_2$, 11,15-bis(tetrahydropyranyl ether)

A twice hexane-washed mineral oil suspension of sodium hydride (0.72 g, 17 mmol) in 50 ml of dry DMSO is heated at 65° for 50 min, cooled to 15°, and treated over 5 min with (4-carboxybutyl)triphenylphosphonium bromide (3.82 g, 8.6 mmol), stirred at 15° for 15 min, treated with 0.69 g (1.50 mmol) of (3'S)-1β-ethynyl-7α-tetrahydropyran-2-yloxy-6β-[3'-tetrahydropyran-2-yloxy-trans-1'-octenyl]bicyclo[3.3.0]octan-3-one in 10 ml dry DMSO, heated at 40°-45° under nitrogen for 44 hr, cooled to 0°, treated with 5.5 ml water, stirred for 3 hr, added to 100 ml of 1:1 water-brine, acidified, and extracted with three 100 ml portions of ether. The combined ether extracts are washed with four 100 ml portions of water and one 100 ml portion of brine and dried (MgSO$_4$). The solvents are removed under reduced pressure and the residue chromatographed on 100 g of acid-washed silica gel eluting with 1600 ml 15% ethyl acetate in hexane, then with 30% ethyl acetate in hexane to give 0.64 g (78%) of title compound (c) as a colorless oil (R$_f$ 0.40 in 64:35:1 hexane-ethyl acetate-acetic acid).

NMR (CDCl$_3$, TMS): δ 0.89 (t, J=5 Hz, 3H), 1.06–3.0 (m, 35H), 3.3–4.5 (m, 6H), 4.7 (bs, 2H), 5.0–5.8 (m, 3H), 7.6 (vbs, 1H).

Infrared: νmax (film): 3310, 2110, 1735, 1710, 1285, 1275, 1260, 1200, 1185, 1160, 1135, 1075, 1035, 1020, 975 cm$^{-1}$.

(d) (5E)-9β-Ethynyl-6a-carba-prostaglandin I$_2$ and (5Z)-9β-Ethynyl-6a-carba-prostaglandin I$_2$ A solution of 0.58 g (1.09 mmol) of 9β-ethynyl-6a-carba-prostaglandin I$_2$, 11,15-bis-(tetrahydropyranyl ether) in 4 ml of tetrahydrofuran, 6 ml of water, and 12 ml of glacial acetic acid is heated at 45° for 3 hr, cooled, diluted with 50 ml brine, and extracted with two 50 ml portions of 3:2 ethyl acetate-Skellysolve B (EtOAc-SSB). The combined ethyl acetate extracts are washed with four 50 ml brine portions, and the combined brine washes are extracted with another 80 ml of 3.2 ethyl acetate-Skellysolve B. The combined organic extracts are dried (Na$_2$SO$_4$) and the solvents removed under reduced pressure (toluene azeotrope). The residue is chromatographed on silica gel eluting with 1000:40:5 chloroform-methanol-acetic acid to give 110 mg (27%) of the title compound (d)(5E) isomer, 15 mg (4%) of a 1:1 mixture of the title (d) isomers, and 155 mg (38%) of the title compound (d) (5Z) isomer as a colorless oil.

The (5E) isomer: R$_f$ 0.44 in the organic phase of 9:2:5:10 ethyl acetate-acetic acid-cyclohexane-water.

NMR (CDCl$_3$, TMS): δ 0.89 (t, J=5 Hz, 3H), 1.08–3.5 (m including 1H singlet at 2.19δ, 23H), 3.7–4.4 (m, 2H), 5.07–6.8 (m including 3H broad singlet at 5.90δ, 6H).

Infrared: νmax (film): 3300 (broad), 2110, 1710, 1455, 1430, 1410, 1300, 1245, 1095, 1075, 970 cm$^{-1}$.

The (5Z) isomer: R$_f$ 0.43 in the organic phase of 9:2:5:10 ethyl acetate-acetic acid-cyclohexane-water.

NMR (CDCl$_3$, TMS): δ 0.89 (t, J=5 Hz, 3H), 1.07–3.1 (m including 1H singlet at 2.21δ, 23H), 3.7–4.4 (m, 2H), 5.0–6.5 (m including 3H broad singlet at 5.83δ, 6H).

Infrared: νmax (film): 3300 (broad), 2110, 1710, 1455, 1430, 1410, 1300, 1245, 1095, 1075, 970 cm$^{-1}$.

EXAMPLE 28

6β-(t-Butyldimethylsilyloxymethyl)-7α-(tetrahydro pyran-2-yloxyl-1β-(trimethylsilylethynyl)-bicyclo-[3.3.0]-octan-3-one A solution of 1.6 ml (7.0 mmol) of bis(trimethylsilyl)acetylene in 11 ml of dry THF under a nitrogen atmosphere is treated with 5.7 ml (7.1 mmol) of 1.25M ethereal methyllithium, stirred for 3 hours at ambient temperature and then cooled to 0°. Most of the THF is removed under high vacuum, and then the residue is diluted with 11 ml of ether, treated with 3.4 ml (7.0 mmol) of diethylaluminum chloride (a 25% solution in hexane), stirred for one hour at 0°, and then cannulated into a −10° suspension of 0.18 g (0.7 mmol) nickel-1,4-pentanedionate and 0.64 ml (0.64 mmol) 1M diisobutylaluminum hydride in 11 ml of ether. The resulting black suspension is treated with 1.17 g (3.19 mmol) of 6β-(t-butyldimethylsilyoxymethyl)-7α-(tetrahydropyran-2-yloxy)bicyclo-[3.3.0]octen-3-one using 16 ml of ether for the transfer, stirred at −10° to 0° for 3 hours, added to 100 ml of a saturated aqueous solution of sodium dihydrogen phosphate, and extracted with three 100 ml portions of ether. The combined ether extracts are washed with three 100 ml brine portions and dried over anhydrous magnesium sulfate. The solvents are removed under reduced pressure to give 1.8 g of a brown oil which is chromatographed on 150 g of silica gel eluting with 2300 ml of 10% ethyl acetate in hexane and then with 1:1 ethyl acetate-hexane to give 0.60 g (52%) of the starting enone and 0.56 g (38%) of the title compound (R$_f$ 0.26 in 10% ethyl acetate in hexane).

NMR (CDCl$_3$, TMS): δ 0.11 (s, 15H), 0.90 (s, 9H), 1.1–3.0 (m, 14H), 3.0–4.35 (m, 5H), 4.64 (bs, 1H).

Infrared: γmax (film): 2165 (weak), 1750, 1250, 1120, 1105, 1080, 1035, 1025, 840, 775 cm$^{-1}$.

EXAMPLE 29

(a) 12β-(t-Butyldimethylsilyloxymethyl)-9β-ethynyl-13,14,15,16,17,18,19,20-octanor-6a-carba-prostaglandin I$_2$, 11-(tetrahydropyranyl ether) and (b) 9β-Ethynyl-12β-hydroxymethyl-13,14,15,16,17,18,19,20-octanor-6a-carba-prostaglandin I$_2$, 11-(tetrahydropyranyl ether)

A suspension of 1.8 g (38 mmol) of sodium hydride (50% in mineral oil) is washed twice with hexane, diluted with 130 ml dry dimethyl sulfoxide, heated at 65° for 50 minutes, cooled to 15°, treated over seven minutes with 9.15 g (21 mmol) of 4-carboxybutyltriphenylphosphonium bromide, stirred at 15°-20° for 15 minutes, treated with 1.49 g (3.2 mmol) of ketone of Example 28 (using 30 ml of dimethylsulfoxide for the transfer), heated at 40° under a nitrogen atmosphere for 65 hours, cooled to 0°, treated with 15 ml of water, stirred for 2½ hours, diluted with 200 ml of 1:1 brine-ice water, acidified with 30 ml of 1N aqueous hydrochloric acid, and extracted with three 200 ml portions of ether. The combined ether extracts are washed with two 200 ml portions and water and 200 ml of brine and are dried over anhydrous magnesium sulfate. The solvents are removed under reduced pressure and the residue chromatographed on 600 g of acid-washed silica gel eluting with two liters of 5% ethyl acetate in hexane, then 2 liters of 10% ethyl acetate in hexane, then 2 liters of 20% ethyl acetate in hexane, 1 liter of 30% ethyl acetate in hexane, 3 liters of 50% ethyl acetate in hexane, and then 80% ethyl acetate in hexane to give 0.30 g (20%) of starting ketone (Rf 0.73 in 64:35:1 hexane-EtOAc-HOAC), 0.17 g (14%) of corresponding desilylated ketone (Rf 0.64 in 64:35:1 hexane-EtOAc-HOAC), 0.31 g (27%) of totally desilylated product 29(b) (Rf 0.10 in 64:35:1 hexane-EtOAc-HOAC), and 0.31 g (20%) of product 29(a) characterized as follows ($R_f$ 0.44 in 64:35:1 hexane-ethyl acetate-acetic acid):

NMR: ($CDCl_3$, TMS): $\delta 0.05$ (s, 6H), 0.90 (s, 9H), 1.0–2.8 (m including 1H singlets at 2.14$\delta$ and 2.16$\delta$, 21H), 3.2–4.35 (m, 5H), 4.64 (bs, 1H), 5.1–5.4 (m, 1H).

Infrared: $\gamma$max (film): 3300, 2105 (weak), 1710, 1250, 1120, 1075, 1020, 835 $cm^{-1}$.

EXAMPLE 30

(a) (5Z)-9$\beta$-Ethynyl-12$\beta$-hydroxymethyl-13,14,15,16,17,18,19,20-octanor-6a-carba-prostaglandin - $I_2$, 11-(tetrahydropyranyl ether) and (b) (5E)-9$\beta$-Ethynyl-12$\beta$-hydroxymethyl-13,14,15,16,17,18,19,20-octanor-6a-carba-prostaglandin $I_2$, 11-(tetrahydropyranyl ether)

A degassed solution of 0.39 g (0.82 mmol) of the compound 29(a) from Example 29 from the previous experiment in 10 ml of dry THF at 0° under an argon atmosphere is treated with 3.0 ml (2.2 mmol) of 0.75M tetra-n-butylammonium fluoride in THF and allowed to warm to room temperature. After 18 hours the solution is added to 50 ml of brine and extracted with three 50 ml portions of ethyl acetate. The combined ethyl acetate extracts are washed with 50 ml of brine and dried over anhydrous sodium sulfate. The solvents are removed under reduced pressure and the residue filtered through 20 g of acid-washed silica gel eluting with 100 ml of 2:1 ethyl acetate-hexane. The resulting yellow oil (upon evaporation of solvents) is combined with compound 29(b) obtained from Example 29 and chromatographed on silica gel eluting with 50:50:0.25 ethyl acetate-hexane-acetic acid to give 0.27 g of 30(a) and 0.23 g of 30(b).

For Compound 30(a): $R_f$ 0.27 in 50:50:1 ethyl acetate-hexane-acetic acid.

NMR ($CDCl_3$, TMS): $\delta 1.2–3.34$ (m including 1H singlet at 2.22$\delta$, 21H), 3.34–4.44 (m, 5H), 4.5–4.9 (m, 1H), 5.15–5.5 (m, 1H), 6.38 (bs, 2H).

Infrared: $\gamma$max (film): 3275, 3205 (weak), 1710, 1245, 1200, 1125, 1075, 1025, 975 $cm^{-1}$.

For Compound 30(b): $R_f$ 0.22 in 50:50:1 ethyl acetate-hexane-acetic acid.

NMR ($CDCl_3$, TMS): $\delta 1.1–3.3$ (m including 1H singlet at 2.19$\delta$, 21H), 3.3–4.4 (m, 5H), 4.4–4.9 (m, 1H), 5.13–5.48 (m, 1H), 6.1 (bs, 2H).

Infrared: $\gamma$max (film): 3275, 2105 (weak), 1730, 1125, 1075, 1025 $cm^{-1}$.

EXAMPLE 31

(5Z)-9$\beta$-Ethynyl-12$\beta$-formyl-13,14,15,16,17,18,19,20-octanor-6a-carba-prostaglandin $I_2$, methyl ester, 11-(tetrahydropyranyl ether)

A solution of 0.30 g (0.83 mmol) of compound 30(a) from Example 30 in 4.3 ml of acetonitrile stirring at ambient temperature under nitrogen is treated with 0.43 ml (2.5 mmol) of diisopropyl ethyl amine and then with 0.26 ml (4.2 mmol) of methyl iodide, stirred in the dark under a nitrogen atmosphere for 25 hours, diluted with 200 ml of ether, and washed with 15 ml of 10% aqueous sodium thiosulfate solution and two 15 ml portions of brine, and dried over anhydrous sodium sulfate. The solvents are removed in vacuo to give 0.31 g of the methyl ester of compound 30(a) (Rf 0.38 in 50:50 ethyl acetate-hexane) as a yellow oil. Without further purification 287 mg (0.76 mmol) of the above obtained crude oil in 10 ml of methylene chloride at ambient temperature under a nitrogen atmosphere was treated with three spatulas of celite and then all at once with 15 ml of Collins reagent (prepared from 1.55 g of chromium trioxide in 50 ml of methylene chloride treated with 2.5 ml of pyridine and stirred at room temperature under nitrogen for 30 minutes), stirred at ambient temperature for 35 minutes, and filtered through 20 g of silica gel eluting with 100 ml of ethyl acetate. The solvents were removed under reduced pressure and the residue chromatographed on silica gel eluting with 20% ethyl acetate in hexane to give 251 mg (81% from 4) of the title compound ($R_f$0.28 in 20% ethyl acetate in hexane).

NMR ($CDCl_3$, TMS): $\delta 1.1–3.05$ (m including 1H singlet at 2.25$\delta$, 21H), 3.2–4.15 (m including 3H singlet at 3.66$\delta$, 5H), 4.39–4.8 (m, 2H), 5.3 (bt, J=7 Hz, 1H), 9.8 ($\alpha$, J=2 Hz, 1H).

Infrared: $\gamma$max (film): 3275, 1725, 1440, 1200, 1125, 1075, 1030, 975 $cm^{-1}$.

EXAMPLE 32

(5E)-9$\beta$-Ethynyl-12$\beta$-formyl-13,14,15,16,17,18,19,20-octanor-6a-carba-prostaglandin $I_2$, methyl ester, 11-(tetrahydropyranyl ether)

A solution of 247 mg (0.68 mmol) of compound 30(b) from Example 30 in 3.5 ml of acetonitrile is treated with 0.35 ml (2.0 mmol) of diisopropyl ethyl amine and 0.21 ml (3.37 mmol) of methyl iodide, stirred in the dark for 23 hours, diluted with 200 ml of ether, washed with 15 ml of 10% aqueous sodium thiosulfate solution and two 15 ml portions of brine, and dried over anhydrous sodium sulfate. The solvents were removed in vacuo and the residue chromatographed over 20 g silica gel eluting with 1:1 ethyl acetate-hexane to give 188 mg (73%) of the methyl ester of 30(b). Without further purification 187 mg of the above methyl ester of compound 30(b) is dissolved in 6.5 ml of methylene chloride, treated with 3 scoops of oven-dried celite and then with 10 ml of freshly prepared Collins reagent, stirred under a nitrogen atmosphere for 40 minutes, filtered through 20 g of silica gel eluted with 100 ml of ethyl acetate. The solvents are removed under reduced pressure and the residue chromatographed on silica gel eluting with 4:1 hexane:ethyl acetate to give 162 mg (63% from compound 30(b)) of the title compound ($R_f$0.24 in 4:1 hexane-ethyl acetate).

NMR: ($CDCl_3$, TMS): $\delta 1.0–3.0$ (m, including 1H singlet at 2.23$\delta$, 21H), 3.2–4.2 (m including 3H singlet at 3.67$\delta$, 5H), 4.4–4.8 (m, 2H), 5.34 (bt, J=7 Hz, 1H), 9.88 ($\delta$, J=3 Hz, 1H).

Infrared: $\gamma$max (film): 3275, 1725, 1435, 1200, 1125, 1075, 1025, 970 $cm^{-1}$.

EXAMPLE 33

(5Z)-9β-Ethynyl-15-deoxy-15-keto-16-methyl-18,19-tetradehydro-6a-carba-prostaglandin I₂, methyl ester, 11-(tetrahydropyranyl ester)

A mineral oil suspension of sodium hydride (32 mg, 0.7 mmol) in 3 ml of dry THF at 0° under an inert atmosphere is treated with 177 mg (0.76 mmol) of dimethyl 2-oxo-3-methyl-5-heptynyl phosphonate in 4 ml of THF, stirred at 0° for 5 minutes and at room temperature for one hour, cooled to 0° and treated with 239 mg (0.64 mmol) of the compound of Example 31 in 5 ml of THF, stirred at room temperature for 2.5 hours, then diluted with 70 ml of water containing 3 drops of acetic acid, and extracted with three 70 ml portions of ethyl acetate. The combined ethyl acetate extracts are washed with 50 ml of bicarb, 50 ml of brine, and then 25 ml of brine, and are dried over anhydrous sodium sulfate. The solvents are removed under pressure and the residue chromatographed on silica gel eluting with 5:1 hexane-ethyl acetate to give 100 mg of the title compound (R$_f$ 0.29 in 4:1 hexane-ethyl acetate).

NMR: (CDCl₃, TMS): δ1.2 (d, J=7 Hz, 3H) 1.25–3.3 (m including 3H triplet, J=2 Hz, at 1.76δ and 1H singlet at 2.25δ, 27H), 3.3–4.4 (m including 3H singlet at 3.68δ, 6H) 4.45–4.8 (m, 1H), 5.05–5.5 (m, 1H), 6.13–7.2 (m, 2H).

Infrared: δmax (film): 3270, 1730, 1675, 1620, 1435, 1200, 1170, 1120, 1075, 1035, 1020, 975 cm⁻¹.

EXAMPLE 34

(5E)-15-Deoxy-15-keto-9β-ethynyl-16-methyl-18,19-tetradehydro-6a-carba-prostaglandin I₂, methyl ester, 11-(tetrahydropyranyl ether)

A solution of 0.04 ml (0.56 mmol) of thallous ethoxide in 4 ml of dry toluene at 0° under an argon atmosphere is treated with 134 mg (0.58 mmol) of dimethyl-2-oxo-3-methyl-5-heptynylphosphonate in 2 ml of toluene, stirred at 0° for one hour, treated with 160 mg (0.43 mmol) of the compound of Example 32 in 4 ml of toluene, stirred at room temperature for 1½ hours, cooled to 0°, treated with 0.1 ml acetic acid and then with 20 ml of 30% aqueous potassium iodide, diluted with 50 ml of ether and filtered through celite. The filtrate is washed with 50 ml of ice water, 70 ml of bicarb, and 50 ml of brine. The combined aqueous washes are extracted with another 75 ml of ether, and the combined ether extracts are dried over anhydrous sodium sulfate. The solvents are removed under reduced pressure and the residue chromatographed on silica gel eluting with 4:1 hexane-ethyl acetate to give 141 mg of the title compound as a colorless oil.

NMR (CDCl₃, TMS): δ1.2 (d, J=7 Hz, 3H), 1.25–3.13 (m including 3H triplet, J=2 Hz, at 1.77δ and 1H singlet at 2.44δ, 27H), 3.13–4.37 (m including 3H singlet at 3.69δ, 6H), 4.37–4.73 (m, 1H), 5.32 (bt, J=7 Hz, 1H), 6.1–7.2 (m, 2H).

Infrared: γmax (film): 3270, 1735, 1696, 1670, 1620, 1435, 1200, 1120, 1075, 1025, 975 cm⁻¹.

EXAMPLE 35

(5Z)-9β-Ethynyl-16-methyl-18,19-tetradehydro-6a-carba-prostaglandin I₂, methyl ester A solution of 20.3 mg (0.54 mmol) sodium borohydride in 3 ml of methanol at −25° under an argon atmosphere is treated with 99 mg (0.21 mmol) of the compound of Example 33 and 0.2 ml methylene chloride dropwise using 2 ml of methanol for the transfer. The resulting solution is stirred one hour at −25° to −15°, quenched with 0.2 ml of acetic acid, added to 40 ml of brine, and extracted with three 50 ml portions of ethyl acetate. The combined ethyl acetate extracts are washed with 40 ml of bicarb and then 40 ml of brine and are dried over anhydrous sodium sulfate. The solvents are removed under reduced pressure and the residue chromatographed on silica gel eluting with 2:1 hexane-ethyl acetate to give 68 mg (68%) of an alcohol mixture (two spots in 3:1 hexane-ethyl acetate: Rf 0.22 (minor) and Rf 0.17 (major)).

Without further purification the 68 mg (0.14 mmol) of alcohol mixture is dissolved in 1.5 ml of THF, 2.3 ml of water, and 4.5 ml of glacial acetic acid, and heated at 40°–45° under a nitrogen atmosphere for three hours, cooled, diluted with 50 ml of brine, and extracted with two 50 ml portions of ethyl acetate. The combined ethyl acetate extracts are washed with 50 ml of brine, three 50 ml portions of bicarb, and 50 ml of brine, and dried over anhydrous sodium sulfate. The solvents are removed in vacuo and the residue chromatographed on 20 g of silica gel eluting with 80 ml 20% acetone in methylene chloride then with 30% acetone in methylene chloride to give 16 mg (28%) of the 15β-isomer (Rf 0.46 in 20% acetone in methylene chloride and 30 mg (53%) of the title compound (R$_f$ 0.26 in 20% acetone in methylene chloride).

NMR: (CDCl₃, TMS): δ0.98 (t (dd), J=6 Hz, 3H), 1.12–3.3 (m including 3H triplet, J=2 Hz, at 1.80δ and 1H singlet at 2.20δ, 23H), 3.4–4.2 (m including 3H singlet at 3.68δ, 5H), 5.1–5.72 (m, 3H).

EXAMPLE 36

(5E)-9β-Ethynyl-16-methyl-18,19-tetradehydro-6a-carba-prostaglandin I₂, methyl ester A solution of 29 mg (0.77 mmol) of sodium borohydride in 4 ml of methanol at −30° under argon is treated dropwise with a solution of 141 mg (0.29 mmol) of the compound of Example 34 and 0.3 ml of methylene chloride in 3 ml of methanol, stirred at −25° to −15° for 1½ hours, cooled to −30°, quenched dropwise with 0.3 ml of acetic acid, diluted with 50 ml of brine, and extracted with three 50 ml portions of ethyl acetate. The combined ethyl acetate extracts are washed with 50 ml of bicarb and 50 ml of brine and are dried over anhydrous sodium sulfate. The solvents are removed in vacuo and the residue chromatographed on silica gel eluting with 2:1 hexane-ethylacetate to give 122 mg (86%) of alcohol mixture (two spots in 2:1 hexane-ethyl acetate: Rf 0.39 (minor) and Rf 0.34 (major)).

Without further purification 119 mg (0.25 mmol) of the above alcohol mixture is dissolved in 1.5 ml of THF, 2.3 ml of water, and 4.5 ml of acetic acid, heated at 40°–45° under a nitrogen atmosphere for 3 hours, cooled, diluted with 50 ml of brine, and extracted with two 50 ml portions of ethyl acetate. The combined ethyl acetate extracts are washed with 50 ml of brine, three 50 ml portions of bicarb, and 50 ml of brine, and are dried over anhydrous sodium sulfate. The solvents are removed under reduced pressure and the residue chromatographed on silica gel eluting with 20% acetone in methylene chloride to give 29 mg (30%) of the 15β-isomer (Rf 0.45 in 20% acetone in methylene chloride) and 63 mg (64%) of the title compound (R$_f$ 0.27 in 20% acetone in methylene chloride).

NMR: (CDCl$_3$, TMS): δ0.98 (t(dd), J=6 Hz, 3H), 1.13–3.41 (m including 3H triplet, J=2 Hz, at 1.8δ and 1H singlet at 2.18δ, 23H), 3.48–4.2 (m including 3H singlet at 3.69δ, 5H), 5.0–5.7 (m, 3H).

Infrared: γmax (film): 3400, 3275, 2100 (weak), 1730, 1715, 1430, 1250, 1170, 1010, 970 cm$^{-1}$.

EXAMPLE 37

(5Z)-9β-Ethynyl-16-methyl-18,19-tetradehydro-6a-carba-prostaglandin I$_2$

A solution of 30 mg (0.075 mmol) of the compound of Example 35 in 2 ml of 9:1 methanol-water at 0° is treated with 2 ml of 10% potassium hydroxide in 9:1 methanol-water allowed to warm to room temperature. After 16 hours the solution is diluted with 50 ml of 1:1 brine-ice, acidified with 1N aqueous hydrochloric acid, and extracted with three 50 ml portions of ethyl acetate. The combined ethyl acetate extracts are washed with 50 ml of brine and dried over anhydrous sodium sulfate. The solvents are removed under reduced pressure and the residue chromatographed on 15 g of acid-washed silica gel eluting with 50 ml of 1:1 ethyl acetate-hexane then with 2:1 ethyl acetate-hexane to give 28 mg (97%) of the title compound as a colorless oil (R$_f$ 0.40 in 15:1:0.15 chloroform-methanol-acetic acid).

NMR (CDCl$_3$, TMS): δ0.99 (t(dd), J=6 Hz, 3H), 1.1–2.8 (m including 1H singlet at 2.22δ, 21H), 3.72–4.2 (m, 2H), 4.7–5.7 (m, 6H).

EXAMPLE 38

(5E)-9β-Ethynyl-16-methyl-18,19-tetradehydro-6a-carba-prostaglandin I$_2$

A solution of 61 mg (0.15 mmol) of the compound of Example 36 in 2 ml of 9:1 methanol-water at 0° is treated with 2 ml of 10% potassium hydroxide in 9:1 methanol-water and let warm slowly to room temperature. After 16 hours the solution is diluted with 50 ml of 1:1 brine-ice, acidified with 1N aqueous hydrochloric acid, and extracted with three 50 ml portions of ethyl acetate. The combined ethyl acetate extracts are washed with 50 ml of brine and dried over anhydrous sodium sulfate. The solvents are removed under reduced pressure and the residue chromatographed on 15 g of acid-washed silica gel eluting with 50 ml of 1:1 ethyl acetate-hexane and then with 2:1 ethyl acetate-hexane to give 57 mg (97%) of the title compound as a colorless oil (R$_f$ 0.42 in 15:1:0.15 chloroform-methanol-acetic acid).

NMR: (CDCl$_3$, TMS): δ0.98 (t(dd), J=6H$_2$, 3H), 1.15–3.3 (m including 1H singlet at 2.19δ, 21H), 3.78–4.3 (m, 2H), 5.07–6.3 (m, 6H).

Infrared: γmax (film): 3300 (broad), 3270, 1700, 1435, 1240, 1010, 970 cm$^{-1}$.

EXAMPLE 39

(a) When in the procedure of Example 1 (3′S)-7α-tetrahydropyran-2-xyloxy-6β-[3′-tetrahydro-2-yloxyoctanyl]bicyclo[3.3.0]octen-3-one or (3′S)-7α-tetrahydropyran-2-yloxy-6β-[3′-tetrahydro-3-yloxy-1′-octynyl]bicyclo[3.3.0]octan-3-one is substituted for (3′S)-7α-tetrahydropyran-2-yloxy-6β-[3′-tetrahydro-3-yloxy-trans-1′-octenyl]bicyclo[3.3.0]-octan-3-one and the general procedure of Example 1 is otherwise followed, one obtains respectively (3′S)-1β-cyano-7α-tetrahydropyran-2-yloxy-6β-[3′-tetrahydropyran-2-yloxyoctanyl]-bicyclo[3.3.0]octan-3-one and (3′S)-1β-cyano-7α-tetrahydropyran-2-yloxy-6β-[3′-tetrahydropyran-2-yloxy-1′-octynyl]bicyclo[3.3.0]octan-3-one.

(b) When each of the products obtained in 39(a) is substituted for (3′S)-1β-cyano-7α-tetrahydropyran-2-yloxy-6β-[3′-tetrahydro-2-yloxy-trans-1′-octenyl]bicyclo[3.3.0]octan-3-one in Example 3 and the procedures of Examples 3 to 6 are otherwise followed, one obtains respectively the 5E and 5Z individual isomers of 9β-cyano-13,14-dihydro-6a-carba-prostaglandin I$_2$ methyl ester and the 5E and 5Z individual isomers of 9β-cyano-13,14-didehydro-6a-carba-prostaglandin I$_2$ methyl ester.

(c) When the methyl esters obtained in 39(b) are substituted for (5Z)-9β-cyano-6a-carba-prostaglandin I$_2$ methyl ester in the procedure of Example 7 one obtains the corresponding free carboxylic acids of the compounds of 39(b).

EXAMPLE 40

When in the procedure of Example 9 (3′S)-7α-tetrahydropyran-2-yloxy-6β-[3′-tetrahydro-2-yloxyoctanyl]bicyclo[3.3.0]octen-3-one or (3′S)-7α-tetrahydropyran-2-yloxy-6β-[3′-tetrahydro-2-yloxy-1′-octynyl]bicyclo[3.3.0]octen-3-one is substituted for 3′S)-7α-tetrahydropyran-2-yloxy-6β-[3′-tetrahydropyran-2-yloxy-trans-1′-octenyl]bicyclo[3.3.0]octen-3-one and the general procedure of Example 9 is otherwise followed one obtains respectively (3′S)-1β-hydroxymethyl-7α-tetrahydropyran-2-yloxy-6β-[3′-tetrahydropyran-2-yloxyoctanyl]bicyclo[3.3.0]octan-3-one and (3′S)-1β-hydroxymethyl-7α-tetrahydropyran-2-yloxy-6β-[3′-tetrahydropyran-2-yloxy-1′-octynyl]bicyclo[3.3.0]octan-3-one and when each of these compounds so obtained is substituted for (3′S)-1β-hydroxymethyl-7α-tetrahydropyran-2-yloxy-6β-[3′-tetrahydropyran-2-yloxy-trans-1′-octenyl]bicyclo[3.3.0]octan-3-one in the procedure of Example 10 one obtains respectively the 5E and 5Z isomers of 9β-hydroxymethyl-13,14-dihydro-6a-carba-prostaglandin I$_2$ methyl ester, 11,15-bis(tetrahydropyranyl ether) and 9β-hydroxymethyl-13,14-didehydro-6a-carba-prostaglandin I$_2$ methyl ester, 11,15-bis(tetrahydropyranyl ether).

When the above-obtained 5E and 5Z isomers are each substituted for 9β-hydroxymethyl-6a-carba-prostaglandin I$_2$ methyl ester, 11,15-bis(tetrahydropyranyl ether)

in Example 18 and the general procedure of Example 18 is followed one obtains the 5E and 5Z individual isomers of 9β-formyl-13,14-dihydro-6a-carba-prostaglandin $I_2$ methyl ester, 11,15-bis(tetrahydropyranyl ether) and the 5E and 5Z individual isomers of 9β-formyl-13,14-didehydro-6a-carba-prostaglandin $I_2$ methyl ester which can be 11,15-deprotected by the general procedure of Example 19 then hydrolyzed to the corresponding free carboxylic acids by treatment with 10% potassium hydroxide (in 9:1 methanol-water) in a 9:1 methanol-water solution to give respectively the 5E and 5Z individual isomers of 9β-formyl-13,14-dihydro-6a-carba-prostaglandin $I_2$ and the 5E and 5Z individual isomers of 9β-formyl-13,14-didehydro-6a-carba-prostaglandin $I_2$.

EXAMPLE 41

When in the procedure of Example 21 the 5E and 5Z isomers of each of 9β-formyl-13,14-dihydro-6a-carba-prostaglandin $I_2$ methyl ester, 11,15-bis(tetrahydropyranyl ether) and 9β-formyl-13,14-didehydro-6a-carba-prostaglandin $I_2$ methyl ester, 11,15-bis(tetrahydropyranyl ether) is substituted for 9β-formyl-6a-carba-prostaglandin $I_2$ methyl ester, 11,15-bis(tetrahydropyranyl ether) and the procedure of Example 21 otherwise followed one obtains each of the corresponding 9β-vinyl substituted compounds which when substituted for 9β-vinyl-6a-carba-prostaglandin $I_2$ methyl ester, 11,15-bis(tetrahydropyranyl ether) in Example 22 and the procedure of Example 22, absent the isomer separation step, is followed one obtains the 5E and 5Z isomers of 9β-vinyl-13,14-dihydro-6a-carba-prostanglandin $I_2$ and the 5E and 5Z isomers of 9β-vinyl-13,14-didehydro-6a-carba-prostaglandin $I_2$.

EXAMPLE 42 when in the procedure of Example 27 (3'S)-7α-tetrahydropyran-2-xyloxy-6β-[3'-tetrahydro-2-yloxyoctanyl]bicyclo[3.3.0]octen-3-one or (3'S)-7α-tetrahydropyran-2-yloxy-6β-[3'-tetrahydro-3-yloxy-1'-octynyl]-bicyclo[3.3.0]octan-3-one is substituted for (3'S)-7α-tetrahydropyran-2-yloxy-6β-[3'-tetrahydropyran-2-yloxy-trans-1'-octenyl]bicyclo[3.3.0]octen-3-one and the procedure of example 27(a) through 27(d) is otherwise followed one obtains as products the 5E and 5Z individual isomers of 9β-ethynyl-13,14-dihydro-6a-carba-prostaglandin $I_2$ and the 5E and 5Z individual isomers of 9β-ethynyl-13,14-didehydro-6a-carba-prostaglandin $I_2$.

EXAMPLE 43

When in the procedure of Example 27 3-oxo-8a-tetrahydropyran-2-yloxy-7β-[3'S)-3'-tetrahydropyran-2-yloxy-trans-1'-octenyl]bicyclo[4.3.0]non-1-ene is substituted for (3'S)-7α-tetrahydropyran-2-yloxy-6β-[3'-tetrahydropyran-2-yloxy-trans-1'-octenyl]bicyclo[3.3.-0]octen-3-one and the procedure of 27(a) to 27(d) is otherwise followed one obtains the 5E and 5Z isomers of 9β-ethynyl-6a-carba-7a-homo-prostaglandin $I_2$.

EXAMPLE 44

When in the procedure of Example 26(a) trifluoromethylacetylene, methoxyacetylene, or 4-methylbutadiyne is substituted for 1-pentyne and the procedure of Example 26(a) to 26(c) is otherwise followed the 5E and 5Z individual isomers of the following products are obtained: 9β-trifluoromethylenthynyl-6a-carba-prostaglandin $I_2$, 9β-methoxyethynyl-6a-carba-prostaglandin $I_2$, and 9β-(4-methylbutadiyn-1-yl)-6*a-carba-prostaglandin $I_2$*.

EXAMPLE 45

When following the procedure set forth in Chart G (3'S)-1β-ethynyl-7α-tetrahydropyran-2-yloxy-6β-[3'-tetrahydropyran-2-yloxy-trans-1'-octenyl]bicyclo[3.3.-0]octan-3-one is utilized as the compound of Formula A-2 and a compound of Formula G-1 wherein $R_{21}$ is trimethylsilyl and $Z_1$ is $-(CH_2)_3-$, i.e., N-methyl-S-(w-hydroxypentyl)-S-phenylsulfoxime, trimethylsilyl ether, one obtains 9β-ethynyl-5-fluoro-6a-carba-prostaglandin $I_2$, 11,15-bis-(tetrahydropyranyl ether) which is treated in the same manner as 9β-ethynyl-6a-carba-prostaglandin $I_2$, 11,15-bis-(tetrahydropyranyl ether) in the procedure of Example 27(d) to give the 5E and 5Z isomers of 9β-ethynyl-5-fluoro-6a-carba-prostaglandin $I_2$.

EXAMPLE 46

When following the procedure set forth in Chart F (3'S)-1β-ethynyl-7α-tetrahydropyran-2-yloxy-6β-[3'-tetrahydropyran-2-yloxy-trans-1'-octenyl]bicyclo[3.3.-0]octan-3-one is utilized as the compound of Formula A-2 and 4-(trimethylsilyloxyethyl)benzaldehyde is utilized as the compound of Formula F-2 one obtains 9β-ethynyl-3,4-dinor-2,5-inter-m-phenylene-6a-carba-prostaglandin $I_2$, 11,15-bis-(tetrahydropyranyl ether) which is treated in the same manner as 9β-ethynyl-6a-carba-prostaglandin $I_2$, 11,15-bis-(tetrahydropyranyl ether) in the procedure of Example 27(d) to give the 5E and 5Z isomers of 9β-ethynyl-3,4-dinor-2,5-inter-m-phenylene-6a-carba-prostaglandin $I_2$.

EXAMPLE 47

When following the procedure set forth in chart E 9β-formyl-6a-carba-prostaglandin $I_2$, t-butyldimethylsilyl ether) is utilized as the compound of Formula D-2(a) and it treated with dibromodifluoromethane and triphenylphosphine; or with the anion of diethyldichloromethylphosphonate; or with carbontetrabromide-triphenylphosphine the following respective compounds are obtained:
9β-difluorovinyl-6a-carba-prostaglandin $I_2$,
9β-dichlorovinyl-6a-carba-prostaglandin $I_2$ and
9β-dibromovinyl-6a-carba-prostaglandin $I_2$
which are separated into the individual 5E and 5Z isomers by chromatography on silica gel eluting with ethyl acetate/hexane and subsequently hydrolyzed with tetra-n-butylammonium fluoride in tetrahydrofuran to give the corresponding 11,15-dihydroxy products.

EXAMPLE 48

When in the procedure of Example 33 each of the following phosphonates is substituted for dimethyl-2-oxo-3-methyl-5-heptynyl phosphonate and the procedures of Examples 33, 35 and 37 are followed one obtains the 9β-ethynyl products listed below:
dimethyl-2-oxo-3-phenylpropyl phosphonate;

dimethyl-2-oxo-4-phenylbutyl phosphonate;
dimethyl-2-oxo-3-phenoxypropyl phosphonate;
dimethyl-2-oxo-4-(3-thienyl)butyl phosphonate;
dimethyl-2-cyclohexyl-2-oxoethyl phosphonate;
dimethyl-2-oxo-3-(3-thienyloxy)propyl phosphonate; or
dimethyl-2-oxo-2-(3-ethylcyclobutyl)ethyl phosphonate;
(5Z)-9β-ethynyl-16-phenyl-17,18,19,20-tetranor-6a-carba-prostaglandin I$_2$;
(5Z)-9β-ethynyl-17-phenyl-18,19,20-trinor-6a-carba-prostaglandin I$_2$;
(5Z)-9β-ethynyl-16-phenoxy-17,18,19,20-tetranor-6a-carba-prostaglandin I$_2$;
(5Z)-9β-ethynyl-17-(3-thienyl)-18,19,20-trinor-6a-carba-prostaglandin I$_2$;
(5Z)-9β-ethynyl-15-cyclohexyl-16,17,18,19,20-pentanor-6a-carba-prostaglandin I$_2$;
(5Z)-9β-ethynyl-16-(3-thienyloxy)-17,18,19,20-tetranor-6a-carba-prostaglandin I$_2$; and
(5Z)-9β-ethynyl-15-(3-ethylcyclobutyl)-16,17,18,19,20-pentanor-6a-carba-prostaglandin I$_2$;

FORMULAS

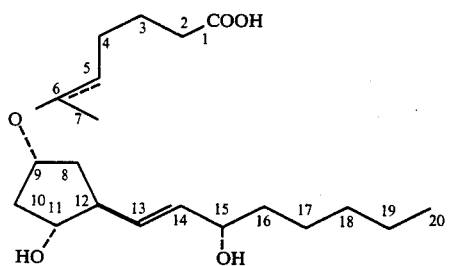

I

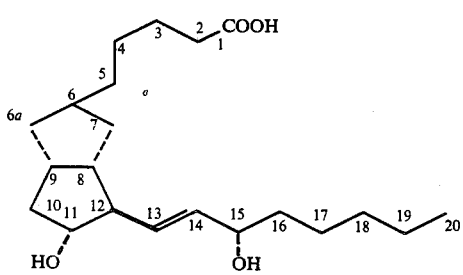

II

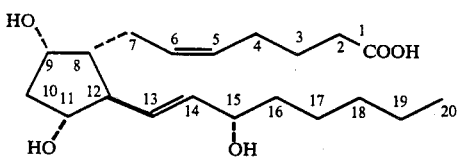

III

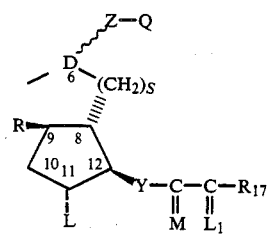

IV

-continued
FORMULAS

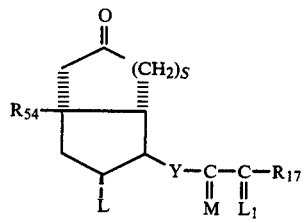

Formula V

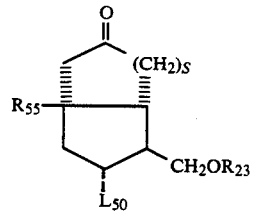

Formula VI

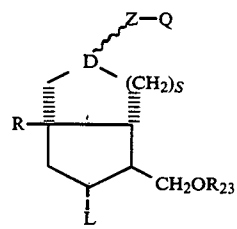

Formula VII

CHART A

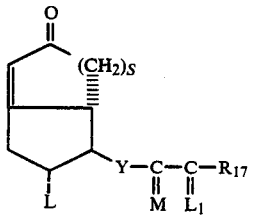

Formula A-1

Formula V

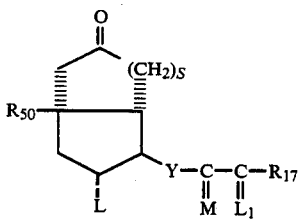

Formula A-3

CHART B
Formulas A-2, A-3
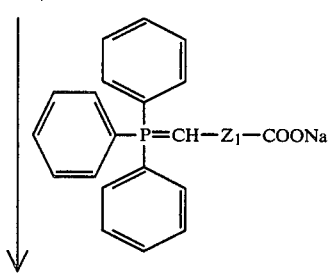
Formula B-1
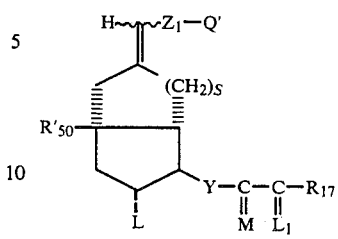
CHART C
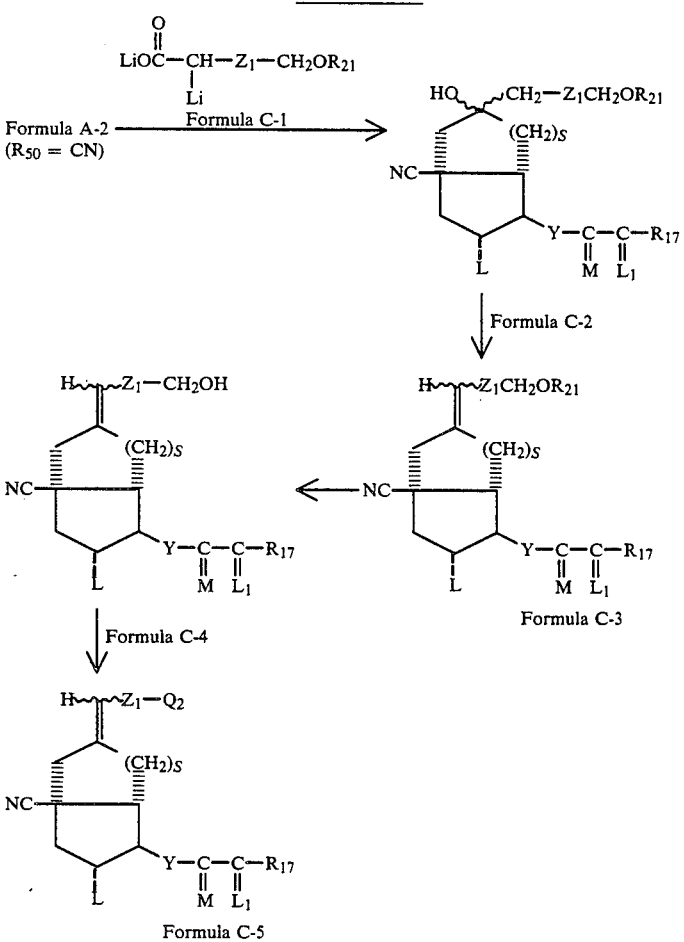
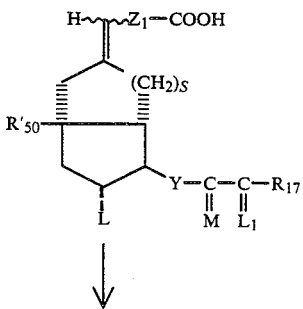
Formula B-2
CHART D -continued
CHART D
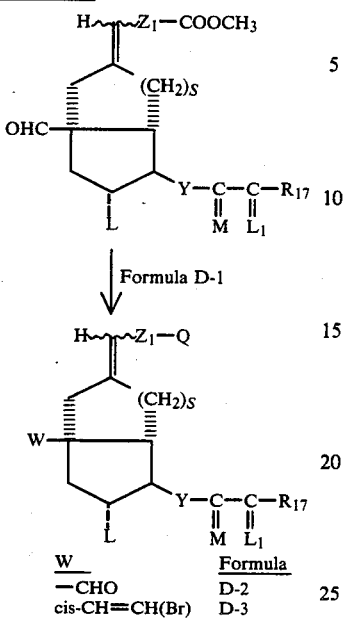
W | Formula
--- | ---
—CHO | D-2
cis-CH=CH(Br) | D-3
CHART E
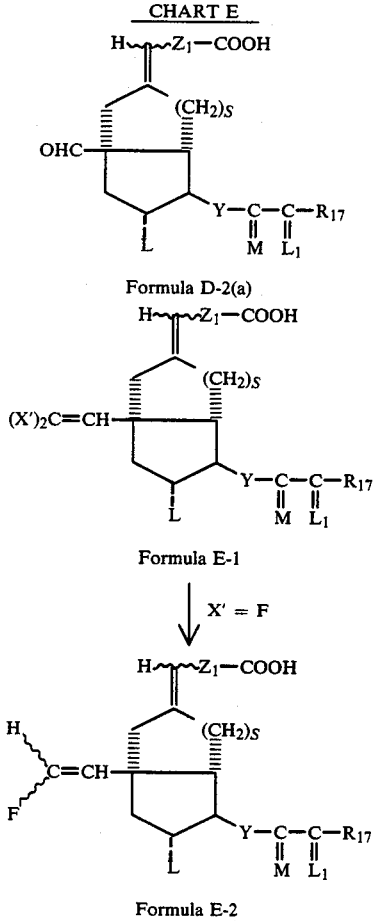
CHART F
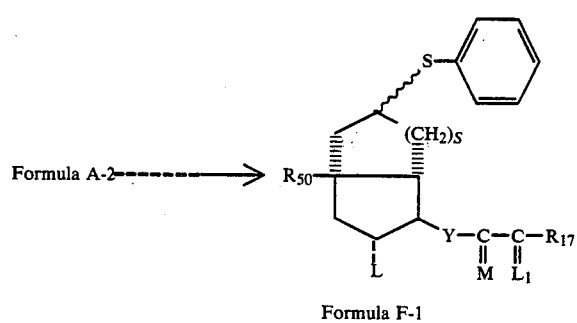
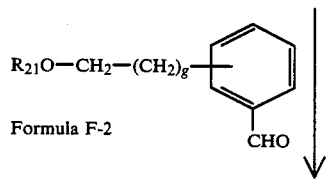
Formula F-2

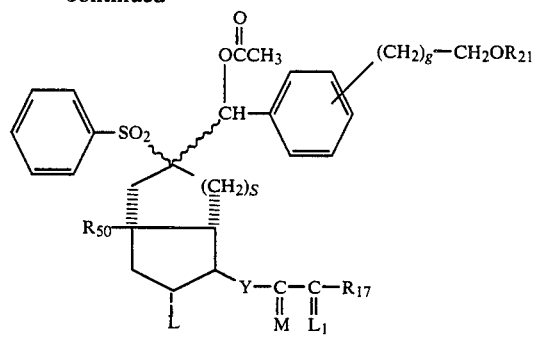
Formula F-3
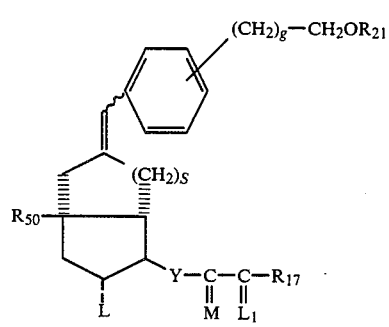
Formula F-4
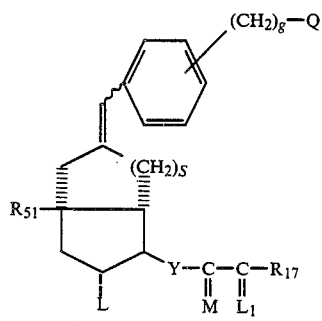
Formula F-5
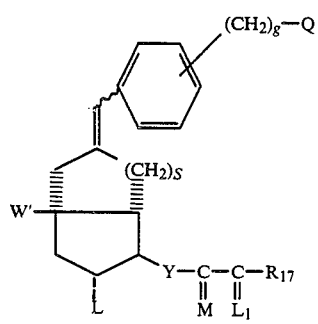
| W' | Formula |
|---|---|
| —CHO | F-6 |
| —CH=CH(X')$_2$ | F-7 |
| 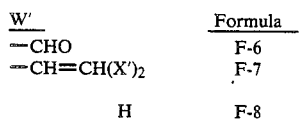 | F-8 |
| cis-CH=CH(Br) | F-9 |
CHART G
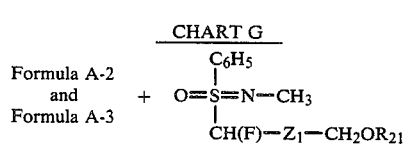
Formula G-1
↓
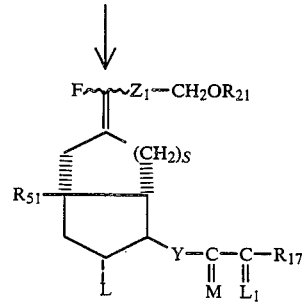
Formula G-2
↓
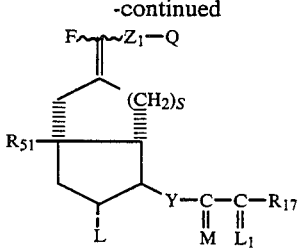
Formula G-3
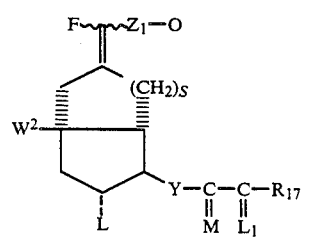
| W$^2$ | Formula |
|---|---|
| —CHO | G-4 |

-continued

—CH=C(X')₂      G-5

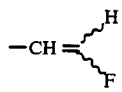      G-6 cis-CH=CH(Br)      G-7

I claim:

1. A compound of the formula

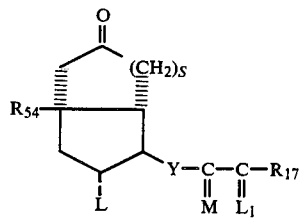

wherein s is the integer one or 2;
wherein L is H,H; $\alpha$-OR$_{12}$,$\beta$-H; $\alpha$-H,$\beta$-OR$_{12}$; $\alpha$-CH$_2$OR$_{12}$,$\beta$-H; $\alpha$-H,$\beta$-CH$_2$OR$_{12}$ wherein R$_{12}$ is hydrogen or a hydroxyl protective group;
wherein Y is trans —CH=CH—, cis-CH=CH—, —CH$_2$CH$_2$—, or —C≡C—;
wherein M is $\alpha$-OR$_{12}$,$\beta$-R$_{14}$; or $\alpha$-R$_{14}$,$\beta$-OR$_{12}$, wherein R$_{12}$ is as defined above, and R$_{14}$ is hydrogen or methyl; wherein L$_1$ is $\alpha$-R$_{15}$,$\beta$-R$_{16}$; $\alpha$-R$_{16}$,$\beta$-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;
wherein R$_{17}$ is (1) —C$_m$H$_{2m}$CH$_3$ wherein m is an integer of from one to 5,
(2) phenoxy optionally substituted by one, 2, or 3 chloro, fluoro, trifluoromethyl, (C$_1$-C$_3$)alkyl, or (C$_1$-C$_3$)alkoxy, with the proviso that not more than two substituents are other than alkyl and with the proviso that R$_{17}$ is phenoxy or substituted phenoxy, only when R$_{15}$ and R$_{16}$ are hydrogen or methyl, being the same or different;
(3) phenyl, benzyl, phenylethyl, or phenylpropyl optionally substituted on the aromatic ring by one, 2, or 3 chloro, fluoro, trifluoromethyl (C$_1$-C$_3$)alkyl, or (C$_1$-C$_3$)alkoxy, with the proviso that not more than two substituents are other than alkyl,
(4) cis-CH=CH—CH$_2$CH$_3$,
(5) —(CH$_2$)$_2$—CH(OH)—CH$_3$,
(6) —(CH$_2$)$_3$—CH=C(CH$_3$)$_2$,

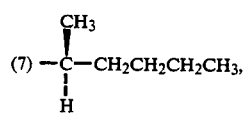

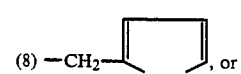

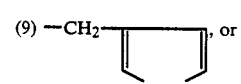

wherein

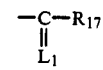

taken together is
(1) (C$_4$-C$_7$)cycloalkyl optionally substituted by one to 3 (C$_1$-C$_5$)alkyl, (2) 3-thienyloxymethyl,

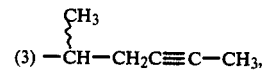

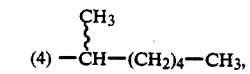

(5) —C≡C—C$_q$H$_{2q}$CH$_3$ wherein q is an integer of from 2 to 6, or
(6) —C$_p$H$_{2p}$CH=CH$_2$ wherein p is an integer of from 3 to 7; and individual optical isomers thereof;
and wherein R$_{54}$ is —CN; —CH=CH$_2$; —CH$_2$OH; —C≡CH; —C≡CCF$_3$; —C≡CC$_n$H$_{2n}$CH$_3$ wherein n is zero, one, 2 or 3; cis-CH=CHC$_n$H$_{2n}$CH$_3$, trans-CH=CHC$_n$H$_{2n}$CH$_3$ wherein n is zero, one, 2 or 3; —C≡C—C≡C—R$_1$ wherein R$_1$ is hydrogen, methyl or ethyl; —C≡C—OR$_2$ wherein R$_2$ is methyl or ethyl; or CH$_2$X wherein X is bromo or chloro.

2. A compound of the formula

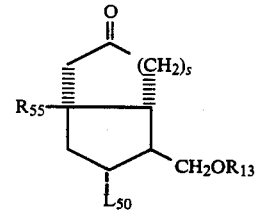

wherein s is one or two; R$_{13}$ is a hydroxyl protecting group; L$_{50}$ is H,H, $\alpha$-OR$_{23}$,$\beta$H; $\alpha$-H,$\beta$-OR$_{23}$; $\alpha$-CH$_2$OR$_{23}$, $\beta$-H; $\alpha$-H,$\beta$-CH$_2$OR$_{23}$ wherein R$_{23}$ is a protecting group; and R$_{55}$ is —CN; —CH=CH$_2$; —CH$_2$OH; —C≡CH; —C≡CCF$_3$; —C≡CC$_n$H$_{2n}$CH$_3$ wherein n is zero, one, 2 or 3; cis-CH=CHC$_n$H$_{2n}$CH$_3$, trans-CH=CHC$_n$H$_{2n}$CH$_3$ wherein n is zero, one, 2 or 3; —C≡C—C≡C—R$_1$ wherein R$_1$ is hydrogen, methyl or ethyl; —C≡C—OR$_2$ wherein R$_2$ is methyl or ethyl; or CH$_2$X wherein X is bromo or chloro; cis-CH=CHX' or trans-CH=CHX' wherein X' is chloro, bromo, or fluoro.

3. A compound of the formula

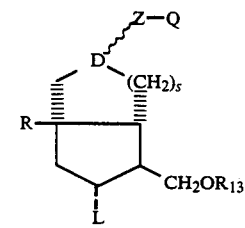

wherein R is —CN; —CH$_2$X wherein X is chloro or bromo; —CH=CH$_2$; —CHO; —CH$_2$OH; —C≡CH; —C≡C—CF$_3$; —C≡C—C$_n$H$_{2n}$CH$_3$ wherein n is zero, one, 2 or 3; cis-CH=CHC$_n$H$_{2n}$CH$_3$ or trans —CH=CHC$_n$H$_{2n}$CH$_3$ wherein n is zero, one, 2 or 3; —CH=C(X')$_2$ wherein X' is fluoro, chloro, or bromo; cis-CH=CHX' or trans-CH=CHX' wherein X' is fluoro, chloro, or bromo; —C≡C—C≡CR$_1$ wherein R$_1$ is hydrogen, methyl, or ethyl; —C≡COR$_2$ wherein R$_2$ is methyl or ethyl;

wherein D is cis-C=C(R$_3$)—, trans-C=C(R$_3$)— or —CH$_2$CH$_2$, wherein R$_3$ is hydrogen or fluoro;

wherein Z is:
(1) —CH$_2$—(CH$_2$)$_f$—C(R$_4$)$_2$— wherein each R$_4$ is the same and is hydrogen or fluoro, and f is zero, one, 2 or 3;
(2) trans-CH$_2$—CH=CH—; or
(3) —(Ph)—(CH$_2$)$_g$— wherein Ph is 1,2-, 1,3-, or 1,4-phenylene and g is zero, one, 2 or 3; with the provisio that when Z is —(Ph)—(CH$_2$)$_g$—, R$_3$ is hydrogen;

wherein Q is
(1) —COOR$_5$, wherein R$_5$ is
(a) hydrogen,
(b) (C$_1$-C$_{12}$)alkyl,
(c) (C$_3$-C$_{10}$)cycloalkyl,
(d) (C$_7$-C$_{12}$)aralkyl,
(e) phenyl optionally substituted with one, 2 or 3 chloro or (C$_1$-C$_4$)alkyl,
(f) phenyl substituted in the para-position with —NHCOR$_6$, —COR$_7$, —OC(O)R$_8$ or —CH=N—NHCONH$_2$, wherein R$_6$ is methyl, phenyl acetamidophenyl, benzamidophenyl or —NH$_2$; R$_7$ is methyl, phenyl, —NH$_2$, or methoxy; and R$_8$ is phenyl or acetamidophenyl;
(g) phthalidyl,
(h) 3-(5,5-dimethyl-1,3,2-dioxaphosphorinan-2-yl)-2-oxopropan-1-yl P-oxide,
(i) 3-(5,5-di(hydroxymethyl)-1,3,2-dioxaphosphorinan-2-yl)-2-oxopropan-1-yl P-oxide, or
(j) a pharmacologically acceptable cation;
(2) —CH$_2$OH;
(3) —COL$_2$, wherein L$_2$ is
(a) an amino group of the formula —NR$_9$R$_{10}$ wherein R$_9$ is
(i) hydrogen
(ii) (C$_1$-C$_{12}$)alkyl
(iii) (C$_3$-C$_{10}$)cycloalkyl,
(iv) (C$_7$-C$_{12}$)aralkyl
(v) phenyl optionally substituted with one, 2 or 3 chloro, (C$_1$-C$_3$)alkyl, hydroxy, carboxy, (C$_2$-C$_5$)alkoxycarbonyl, or nitro,
(vi) (C$_2$-C$_5$)carboxyalkyl,
(vii) (C$_2$-C$_5$)carbamoylalkyl,
(viii) (C$_2$-C$_5$)cyanoalkyl,
(ix) (C$_3$-C$_6$)acetylalkyl,
(x) (C$_7$-C$_{12}$)benzoalkyl, optionally substituted by one, 2, or 3 chloro, (C$_1$-C$_3$)alkyl, hydroxy, (C$_1$-C$_3$)alkoxy, carboxy, (C$_2$-C$_5$)-alkoxycarbonyl, or nitro,
(ix) pyridyl, optionally substituted by one, 2, or 3 chloro, (C$_1$-C$_3$)alkyl, or (C$_1$-C$_3$)alkoxy,
(xii) (C$_6$-C$_9$)pyridylalkyl optionally substituted by one, 2, or 3 chloro, (C$_1$-C$_3$)alkyl, hydroxy, or (C$_1$-C$_3$)alkyl,
(xiii) (C$_1$-C$_4$)hydroxyalkyl,
(xiv) (C$_1$-C$_4$)dihydroxyalkyl,
(xv) (C$_1$-C$_4$)trihydroxyalkyl;
(b) cycloamine selected from the group consisting of pyrolidino, piperidino, morpholino, piperazino, hexamethyleneimino, pyrroline, or 3,4-didehydropiperidinyl optionally substituted by one or 2 (C$_1$-C$_{12}$)alkyl;
(c) carbonylamino of the formula —NR$_{11}$COR$_{10}$, wherein R$_{11}$ is hydrogen or (C$_1$-C$_4$)alkyl and R$_{10}$ is other than hydrogen, but otherwise defined as above;
(d) sulfonylamino of the formula —NR$_{11}$SO$_2$R$_{10}$, wherein R$_{11}$ and R$_{10}$ are defined in (c);
(4) —CH$_2$NL$_3$L$_4$, wherein L$_3$ and L$_4$ are hydrogen or (C$_1$-C$_4$)alkyl, being the same or different, or the pharmacologically acceptable acid addition salts thereof when Q is —CH$_2$NL$_3$L$_4$; or
(5) —CN;

wherein s is the integer one or 2;

wherein L is H,H; $\alpha$-OR$_{12}$,$\beta$-H; $\alpha$-H,$\beta$-OR$_{12}$; $\alpha$-CH$_2$OR$_{12}$, $\beta$-H; $\alpha$-H,$\beta$-CH$_2$OR$_{12}$ wherein R$_{12}$ is hydrogen or a hydorxyl protective group;

and wherein R$_{13}$ is a hydroxyl protecting group.

* * * * *

UNITED STATES PATENT OFFICE
CERTIFICATE OF CORRECTION

Patent No. 4,588,823                     Dated   May 13, 1986

Inventor(s)   Paul A. Aristoff

It is certified that error appears in the above-identified patent and that said Letters Patent are hereby corrected as shown below:

Column 79, lines 45-46, "-$NR_9R_{10}$ wherein $R_9$ is" should read -- -$NR_9R_{10}$ wherein $R_9$ is hydrogen or $(C_1-C_{12})$alkyl and $R_{10}$ is --.

Signed and Sealed this

Sixth Day of September, 1988

Attest:

DONALD J. QUIGG

Attesting Officer     Commissioner of Patents and Trademarks